(12) United States Patent
Johs et al.

(10) Patent No.: US 6,822,738 B1
(45) Date of Patent: *Nov. 23, 2004

(54) SPECTROSCOPIC ROTATING COMPENSATOR ELLIPSOMETER SYSTEM WITH PSEUDO-ACHROMATIC RETARDER SYSTEM

(75) Inventors: Blaine D. Johs, Lincoln, NE (US); Craig M. Herzinger, Lincoln, NE (US)

(73) Assignee: J.A. Woollam Co. Inc., Lincoln, NE (US)

( * ) Notice: Subject to any disclaimer, the term of this patent is extended or adjusted under 35 U.S.C. 154(b) by 371 days.

This patent is subject to a terminal disclaimer.

(21) Appl. No.: 10/034,800

(22) Filed: Dec. 28, 2001

Related U.S. Application Data

(63) Continuation-in-part of application No. 09/945,962, filed on Sep. 4, 2001, and a continuation-in-part of application No. 09/496,011, filed on Feb. 1, 2000, now Pat. No. 6,353,477, which is a continuation-in-part of application No. 09/246,888, filed on Feb. 8, 1999, now Pat. No. 6,084,675, which is a continuation-in-part of application No. 08/912,211, filed on Aug. 15, 1997, now Pat. No. 5,872,630, which is a continuation-in-part of application No. 08/530,892, filed on Sep. 20, 1995, now Pat. No. 5,666,201, and a continuation-in-part of application No. 08/618,820, filed on Mar. 20, 1996, now Pat. No. 5,706,212.

(51) Int. Cl.$^7$ ............................................. G01N 21/00
(52) U.S. Cl. ....................................................... 356/369
(58) Field of Search ................................ 356/364–369; 250/225

(56) References Cited

U.S. PATENT DOCUMENTS

| | | | |
|---|---|---|---|
| 548,495 A | 10/1895 | Abbe | |
| 2,447,828 A | 8/1948 | West | |
| 3,817,624 A | 6/1974 | Master | 350/286 |
| 4,176,951 A | 12/1979 | Robert et al. | 356/33 |
| 4,556,292 A | 12/1985 | Mathyssek et al. | 350/394 |
| 4,772,104 A | 9/1988 | Buhrer | 350/403 |
| 4,961,634 A | 10/1990 | Chipman et al. | 350/403 |
| 5,329,357 A | 7/1994 | Bernoux et al. | 356/369 |
| 5,373,359 A | 12/1994 | Woollam et al. | 356/328 |

(List continued on next page.)

OTHER PUBLICATIONS

WO 01/90687 A2 (Therma Wave).

"Regression Calibration Method For Rotating Element Ellipsometers", which appeared in Thin Film Solids, vol. 234 in 1993.

"Data Analysis for Spectroscopic Ellipsometry", Jellison Jr., Thin Film Solids, 234, (1993).

(List continued on next page.)

*Primary Examiner*—Hoa Q. Pham
(74) *Attorney, Agent, or Firm*—James D. Welch

(57) ABSTRACT

Disclosed is a spectroscopic Ellipsometer having pseudo-achromatic compensator(s) having fast axes which vary with wavelength and which provide, a range of retardations, (that is, maximum retardance minus minimum retardance), of less than 90 degrees over a range of wavelengths, said range of retardations being bounded by a minimum of preferably at least 30 degrees, to a maximum of less than 135 degrees. Calibration is achieved by a Mathematical Regression based technique involving, where desirable, Parameterization of Calibration Parameters. Various Dimensional Data Set(s) obtained with the Spectroscopic Ellipsometer configured in a Sample, present" or in a Straight-through" configuration, are variously normalized to D.C., A.C. or combination D.C. and A.C. components. Sample analysis using a detector provided intensity signal simultaneously comprising 2ω and 4ω signals simultaneously, and use of un-normalized A.C. and/or D.C. signals in reflectance monitoring are also disclosed.

44 Claims, 15 Drawing Sheets

U.S. PATENT DOCUMENTS

| | | | | |
|---|---|---|---|---|
| 5,504,582 A | | 4/1996 | Johs et al. | 356/369 |
| 5,521,706 A | | 5/1996 | Green et al. | 356/369 |
| 5,581,350 A | | 12/1996 | Chen et al. | 356/369 |
| 5,666,201 A | | 9/1997 | Johs et al. | 356/369 |
| 5,706,212 A | | 1/1998 | Thompson et al. | 364/525 |
| 5,872,630 A | | 2/1999 | Johs et al. | 356/369 |
| 5,877,859 A | | 3/1999 | Aspnes et al. | 356/364 |
| 5,946,098 A | | 8/1999 | Johs et al. | 356/364 |
| 5,963,325 A | | 10/1999 | Johs et al. | 356/364 |
| 5,973,787 A | | 10/1999 | Aspnes et al. | 356/369 |
| 6,084,674 A | | 7/2000 | Johs et al. | 356/364 |
| 6,084,675 A | | 7/2000 | Herzinger et al. | 356/369 |
| 6,100,981 A | | 8/2000 | Johs et al. | 356/364 |
| 6,118,537 A | | 9/2000 | Johs et al. | 356/369 |
| 6,134,012 A | | 10/2000 | Aspnes et al. | 356/369 |
| 6,141,102 A | | 10/2000 | Johs et al. | 356/364 |
| 6,320,657 B1 | | 11/2001 | Aspnes et al. | 356/369 |
| 6,353,477 B1 | * | 3/2002 | Johs et al. | 356/369 |
| 6,499,043 B1 | * | 12/2002 | Forcier | 715/541 |
| 6,583,875 B1 | * | 6/2003 | Wei et al. | 356/369 |
| 6,650,415 B2 | * | 11/2003 | Aspnes et al. | 356/369 |
| 2002/0018205 A1 | * | 2/2002 | Aspnes et al. | 356/369 |

OTHER PUBLICATIONS

"Automated Rotating Element Ellipsometers: Calibration, Operation, and Real–Time Applications", Collins, Rev. Sci. Instrum. 61(8), Aug. 1990.

"Systematic Errors in Rotating–Compensator Ellipsometry" Kleim et al., J. Opt. Soc. Am./vol. 11, No. 9, Sep. 1994.

"A New Calculus For The Treatment of Optical Systems", Jones, J.O.S.O., vol. 31, (Jul. 1941).

"Mueller Matrix Ellipsometry With Imperfect Compensators", Hauge, J. Opt. Soc. Am., vol. 68, No. 11, (Nov. 1978).

Papers by Schubert and Schubert et al.: which describe "Generalized Ellipsometry" are disclosed as they provide insight as how to Mathematically treat depolarizing Elements are.

"Polarization Dependent Parameters of Arbitrary Anisotropic Homogeneous Epitaxial Systems", Phys. Rev. B 53, (1996).

"Generalized Transmission Ellipsometry For Twisted Biaxial Dieletric Media: Application to Chiral Liquid Crystals", J. Opt. Soc. Am A, vol. 13, No. 9 (1996); and.

"Extension of Rotating–Analyzer Ellipsometry to Generalized Ellipsometry: Determination of the Dielectric Function Tensor From Uniaxial TiO2", J. Opt. Soc. Am. A. 13, (1996).

"Analysis of Specular and Textured SnO2:F Films by High Speed Four–Parameter stokes Vector Spectroscopy", Rovira & Collins, J. App. Phys., vol. 85, No. 4, (1999).

* cited by examiner

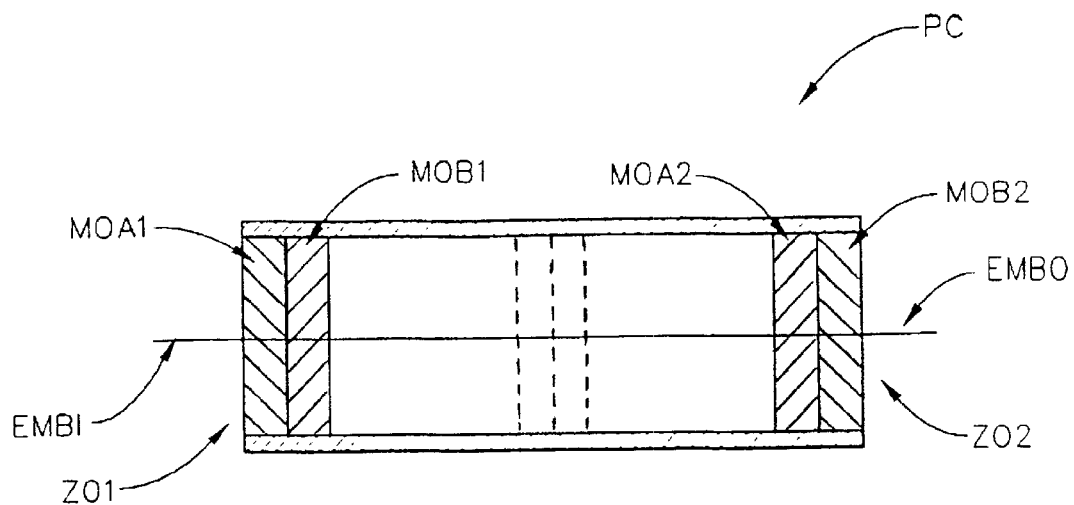
FIG. 9g₁
FIG. 9g₂
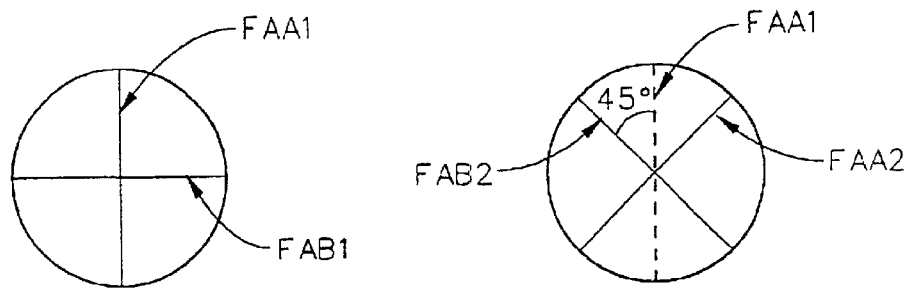
FIG. 9h
FIG. 9i
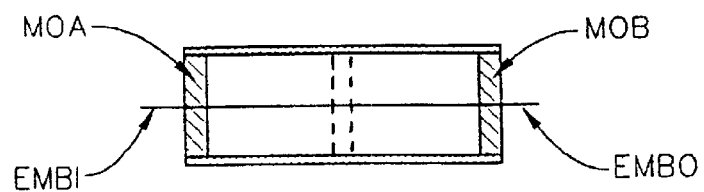
FIG. 9j

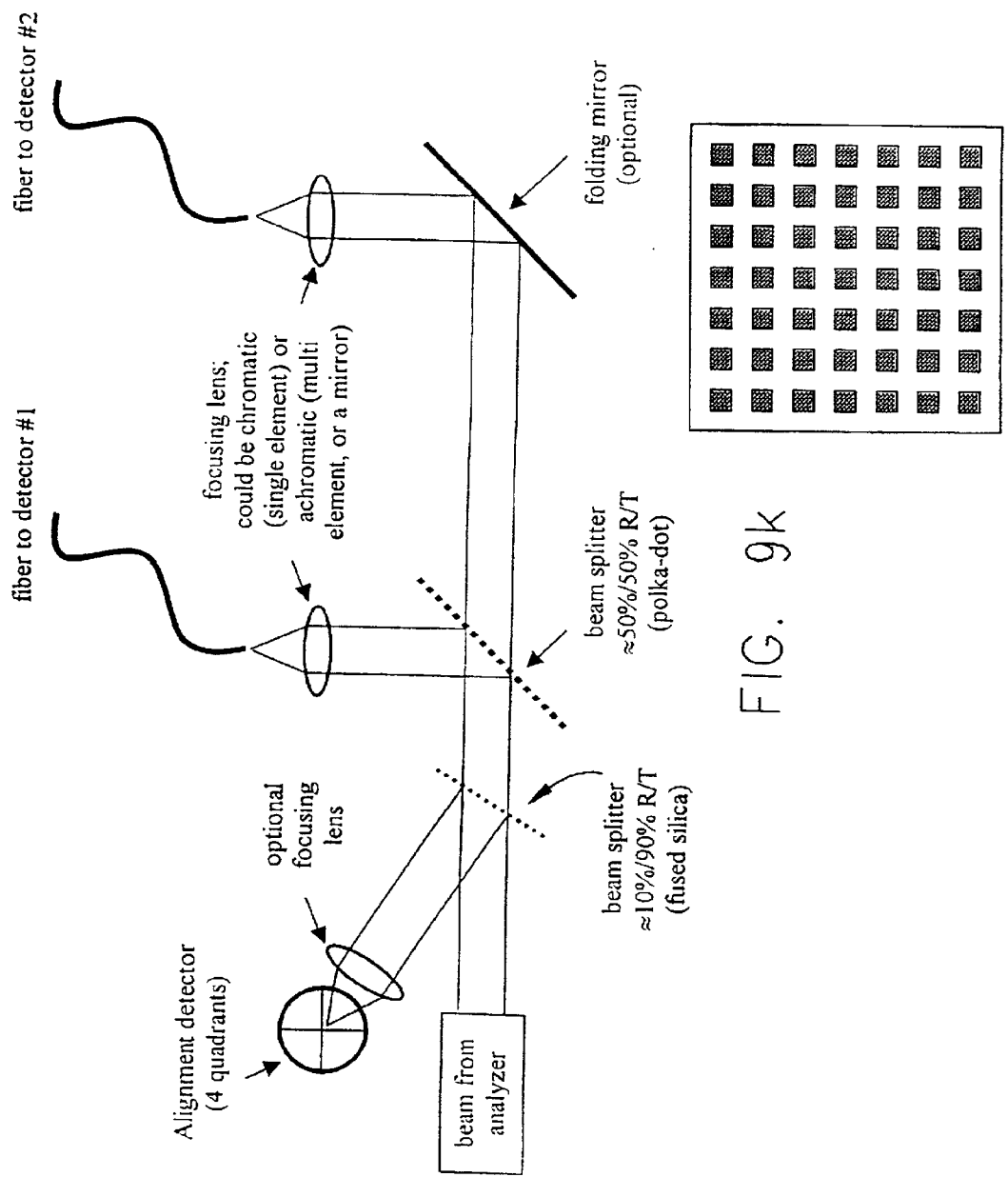

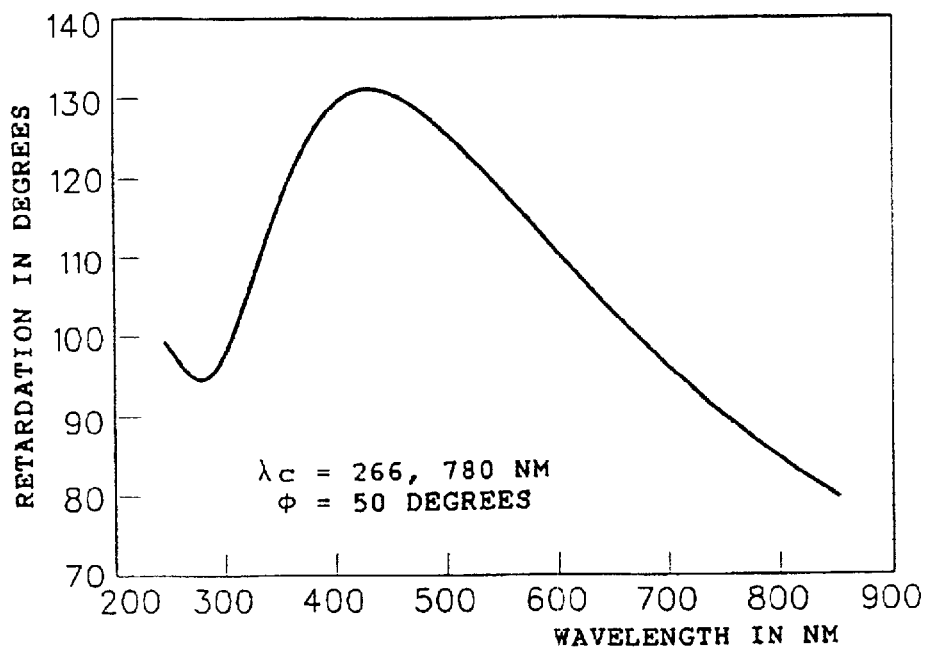
FIG. 10f
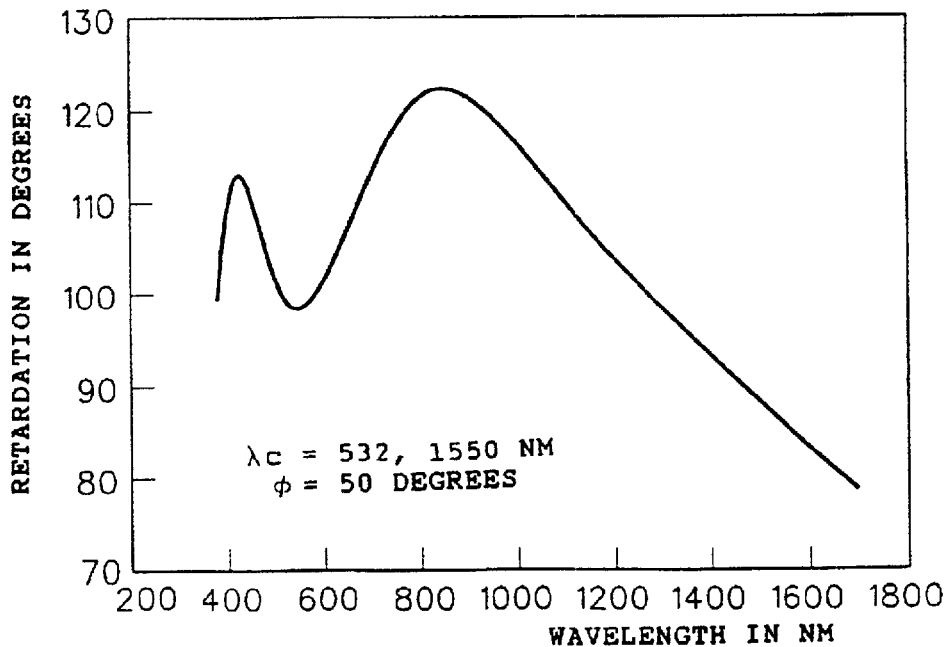
FIG. 10g₁

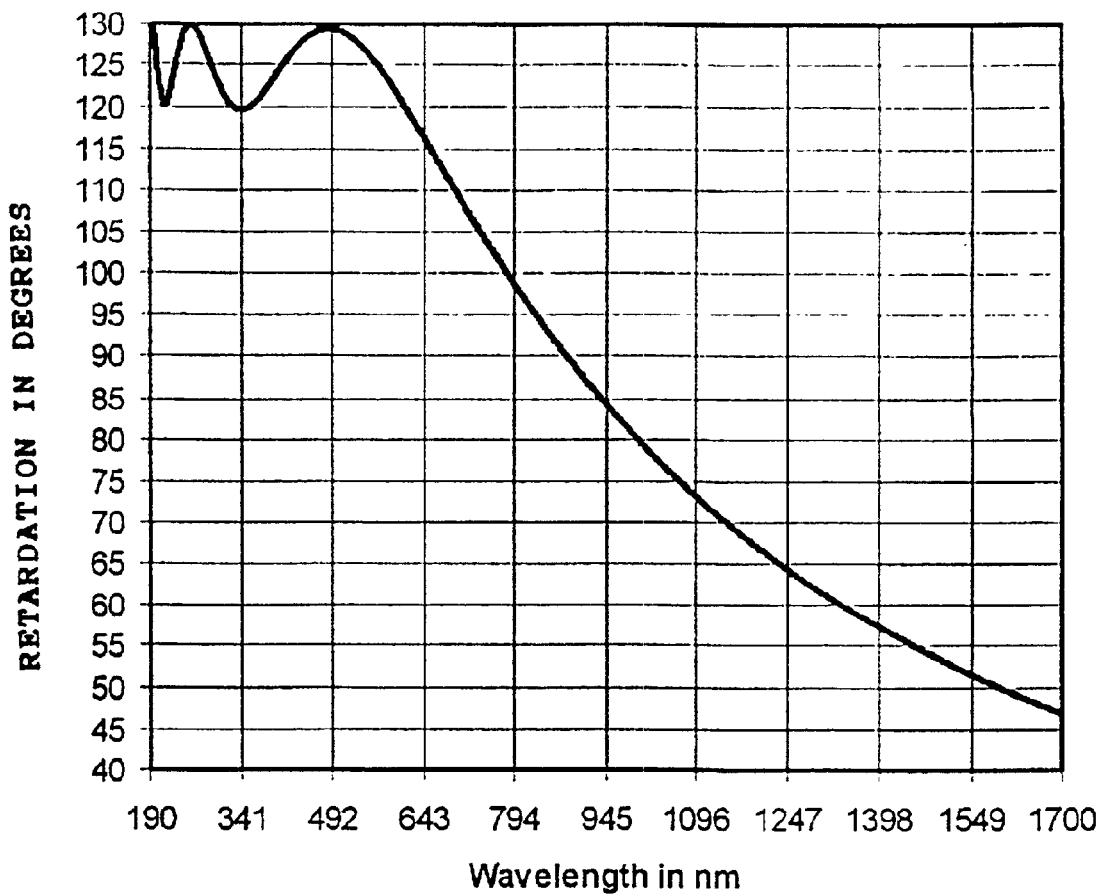
FIG. 10g2

US 6,822,738 B1

SPECTROSCOPIC ROTATING COMPENSATOR ELLIPSOMETER SYSTEM WITH PSEUDO-ACHROMATIC RETARDER SYSTEM

This Application is a Continuation-In-Part of:
Co-pending application Ser. No. 09/945,962 filed Sep. 4, 2001; and
application Ser. No. 09/496,011 filed Feb. 1, 2000 now U.S. Pat. No. 6,353,477;
which is a CIP from application Ser. No. 09/246,888 filed Feb. 8, 1999, (now U.S. Pat. No. (6,084,675);
which is a CIP from application Ser. No. 08/912,211 filed Aug. 15, 1997, (now U.S. Pat. No. 5,872,630);
which is a CIP from application Ser. No. 08/530,892 filed Sep. 20, 1995, (now U.S. Pat. No. 5,666,201);
and is a CIP of application Ser. No. 08/618,820 filed Mar. 20, 1996, (now U.S. Pat. No. 5,706,212);
This Application is, via the Co-Pending application Ser. No. 09/496,011 and application Ser. No. 09/246,888 further a Continuation-In-Part of applications Ser. No. 09/225,118 (now U.S. Pat. No. 6,084,674); Ser. No. 09/223,822 (now U.S. Pat. No. 6,118,537); Ser. No. 09/232,257 (now U.S. Pat. No. 6,141,102); Ser. No. 09/225,371 (now U.S. Pat. No. 6,100,981); Ser. No. 09/225,076 (now U.S. Pat. No. 5,963,325); which Applications depend from application Ser. No. 08/997,311 filed Dec. 23, 1997, now U.S. Pat. No. 5,946,098.

TECHNICAL FIELD

This invention relates to ellipsometers and polarimeters and the like, and more particularly is a Spectroscopic Rotating Compensator Ellipsometer System including a Pseudo-Achromatic Compensator providing, over a range of wavelengths, a range of retardations, (ie. maximum retardance minus minimum retardance), of less than 90 degrees, said range of retardations being bounded by a minimum of preferably at least 30 degrees, to a maximum of less than 135 degrees. Said System also comprises a detector means for simultaneously detecting a Multiplicity of Wavelengths, which Spectroscopic Rotating Compensator Ellipsometer System is calibrated by a Mathematical Regression based technique involving, where beneficial and desired, Parameterization of Calibration Parameters. Prefered embodiments provide a preferred fast axes offset, dual or triple zero-order, or dual or triple effective zero-order, or combination zero-order and effective zero-order waveplate compensator means system; alternative use of D.C. or A.C, and combination A.C. and D.C. data normalizing bases in various calibration steps and use of un-normalized signals to determine reflectance, as well as use of various samples during calibration data acquisition. Said invention system can be realized utilizing off-the-shelf, non-ideal, waveplates combined to provide a compensator which presents a fast axis azimuth which varies with wavelength.

BACKGROUND

Ellipsometry is a well known means by which to monitor material systems, (samples). In brief, a polarized beam of electromagnetic radiation of one or more wavelengths is caused to impinge upon a material system, (sample), along one or more angles of incidence and then interact with a material system, (sample). Beams of electromagnetic radiation can be considered as comprised of two orthogonal components, (ie. "P" and "S"), where "P" identifies a plane which contains both an incident beam of electromagnetic radiation, and a normal to an investigated surface of a material system, (sample), being investigated, and where "S" identifies a plane perpendicular to the "P" plane and parallel to said surface of said material system, (sample). A change in polarization state in a polarized beam of electromagnetic radiation caused by said interaction with a material system, (sample), is representative of properties of said material system, (sample). (Note Polarization State basically refers to a magnitude of a ratio of orthogonal component magnitudes in a polarized beam of electromagnetic radiation, and a phase angle therebetween.) Generally two well known angles, (PSI and DELTA), which characterize a material system, (sample), at a given Angle-of-Incidence, are determined by analysis of data which represents change in polarization state. Additional sample identifying information is often also obtained by application of ellipsometry, including layer thicknesses, (including thicknesses for multilayers), optical thicknesses, sample temperature, refractive indicies and extinction coefficients, index grading, sample composition, surface roughness, alloy and/or void fraction, parameter dispersal and spectral dependencies on wavelength, vertical and lateral inhomogenieties etc.

Continuing, Ellipsometer Systems generally include a source of a beam of electromagnetic radiation, a Polarizer means, which serves to impose a linear state of polarization on a beam of electromagnetic radiation, a Stage for supporting a material system, (sample), and an Analyzer means which serves to select a polarization state in a beam of electromagnetic radiation after it has interacted with a material system, (sample), and pass it to a Detector System for analysis therein. As well, one or more Compensator(s) can be present and serve to affect a phase angle change between orthogonal components of a polarized beam of electromagnetic radiation.

It is noted that Spectroscopic Ellipsometer Systems utilize a Source which simultaneously provides a plurality of Wavelengths, which Source can be termed a "Broadband" Source of Electromagnetic radiation.

A number of types of ellipsometer systems exist, such as those which include rotating elements and those which include modulation elements. Those including rotating elements include Rotating Polarizer (RP), Rotating Analyzer (RA) and Rotating Compensator (RC). The presently disclosed invention comprises a Rotating Compensator Ellipsometer System. It is noted that Rotating Compensator Ellipsometer Systems do not demonstrate "Dead-Spots" where obtaining data is difficult. They can read PSI and DELTA of a Material System, (Sample), over a full Range of Degrees with the only limitation being that if PSI becomes essentially zero (0.0), one can't then determine DELTA as there is not sufficient PSI Polar Vector Length to form the angle between the PSI Vector and an "X" axis. In comparison, Rotating Analyzer and Rotating Polarizer Ellipsometers have "Dead Spots" at DELTA's near 0.0 or 180 Degrees and Modulation Element Ellipsometers also have "Dead Spots" at PSI near 45 Degrees. The utility of Rotating Compensator Ellipsometer Systems should then be apparent. Another benefit provided by fixed Polarizer (P) and Analyzer (A) positions is that polarization state sensitivity to input and output optics during data acquisition is essentially non-existent. This enables relatively easy use of optic fibers, mirrors, lenses etc. for input/output.

A Search for relevant Patents has Identified very little. Most important is a Patent to Johs et al., U.S. Pat. No. 5,872,630, from which the present Application is derived as a CIP. Said 630 Patent describes:

A spectroscopic rotating compensator material system investigation system comprising a source of a polychromatic beam of electromagnetic radiation, a polarizer, a stage for supporting a material system, an analyzer, a dispersive optics and at least one detector system which contains a multiplicity of detector elements, said spectroscopic rotating compensator material system investigation system further comprising at least one compensator(s) positioned at a location selected from the group consisting of:

before said stage for supporting a material system;
after said stage for supporting a material system; and
both before and after said stage for supporting a material system;

such that when said spectroscopic rotating compensator material system investigation system is used to investigate a material system present on said stage for supporting a material system, said analyzer and polarizer are maintained essentially fixed in position and at least one of said at least one compensator(s) is caused to continuously rotate while a polychromatic beam of electromagnetic radiation produced by said source of a polychromatic beam of electromagnetic radiation is caused to pass through said polarizer and said compensators, said polychromatic beam of electromagnetic radiation being also caused to interact with said material system, pass through said analyzer and interact with said dispersive optics such that a multiplicity of essentially single wavelengths are caused to simultaneously enter a corresponding multiplicity of detector elements in said at least one detector system.

Said 630 Patent also, amongst other disclosure, describes a Mathematical Regression based Calibration procedure which makes possible the use of essentially any compensator regardless of non-achromatic characteristics.

Another Patent to Johs, from which the 630 Patent was Continued-in Part, is U.S. Pat. No. 5,666,201, filed Sep. 20, 1995. The focus in said 201 Patent comprises a detector arrangement in which multiple orders of a dispersed beam of electromagnetic radiation are intercepted by multiple detector systems. However, Claim 8 in the 201 Patent, in combination with a viewing the Drawings therein, provide conception of the Spectroscopic Rotating Compensator Ellipsometer, as Claimed in Claim 1 of the JAW 630 Patent and, in fact, the the 630 Patent issued in view of a Terminal Disclaimer based upon the 201 Patent.

Also disclosed is U.S. Pat. No. 5,706,212, Issued Jan. 6, 1998, and Filed Mar. 20, 1996 for an Infrared Ellipsometer System Regression based Calibration Procedure. Said 212 Patent describes use of an Substantially Achromatic Rotating Compensator and application of Mathematical Regression in a Calibration procedure which evaluates calibration parameters in both rotating and stationary components. The 212 Patent describes that 2 OMEGA and 4 OMEGA associated terms are generated by a detector of a signal which passes through a compensator caused to rotate at a rate of OMEGA. Said 630 Patent was Continued-in-Part therefrom, as is the present Application via an intervening Patent Application. It is noted that the 212 Patent Application was filed four months prior to the earliest priority Patent Application, of Aspnes et al. Patents, (ie. U.S. Pat. Nos. 6,320,657 B1, 6,134,012, 5,973,787 and 5,877,859), the later of which was Filed on Jul. 24, 1996.

Relevant Patents to Aspnes et al. are U.S. Pat. Nos. 6,320,657 B1, 6,134,012, 5,973,787 and 5,877,859. These Patents describe a Broadband Spectroscopic Rotating Compensator Ellipsometer System wherein the Utility is found in the use of a "substantially Non-Achromatic" compensator, (see Claim 1 in the 657 Patent), and selecting a Wavelength Range and Compensator so that "an effective phase retardation value is induced covering at least from 90 degrees to 180 degrees", (012 Patent), over a range of wavelengths of at least 200–800 nm. The 787 and 859 recite that at least one wavelength in said wavelength Range has a retardation imposed of between 135 and 225 Degrees, and another wavelength in the wavelength Range has a retardation imposed which is outside that retardation Range. The Utility of the Therma-wave Patents derives from the identified conditions being met so that at least one of a 2 OMEGA and a 4 OMEGA coefficient provided by a detector provides usable information at a wavelength, even when said coefficient does not provide usable information at other wavelengths. Again, the identified Aspnes et al. Patents recite directly, or describe the presence of a "substantially-non-Achromatic" compensator, while, it is noted at this point, the invention disclosed in this Application utlizes what are properly termed substantially-achromatic or Psuedo-Achromatic compensators. It is further noted that the U.S. Pat. No. 5,716,212 Patent Application, from which this Application Continues-in-Part, was filed prior to Jul. 24, 1976 filing date of the 859 Aspnes et al. priority Patent Application. The disclosed invention then has Priority to simultaneous use of 2 OMEGA and 4 OMEGA signals provided from a detector in a spectroscopic rotating compensator ellipsometer system which utilizes "Other-Than-Substantially Non-Achromatic" Compensators, namely "Substantially-Achromatic" or "Pseudo-Achromatic" Compensators, to characterize samples, emphasis added.

A recently published PCT Application is No. WO 01/90687 A2, which is based on U.S. application Ser. No. 09/575,295 filed May 3, 2001. This Application was filed by Thermavave Inc. and specifically describes separate use of a 2ω and a 4ω term to provide insight to sample thickness and temperature.

Another Patent, U.S. Pat. No. 4,053,232 to Dill et al. describes a Rotating-Compensator Ellipsometer System, which operates utilizes monochromatic light.

Two Patents which identify systems which utilize Polychromatic light in investigation of material systems, U.S. Pat. Nos. 5,596,406 and 4,668,086 to Rosencwaig et al. and Redner, respectively, were also identified.

Also identified is a Patent to Woollam et al, U.S. Pat. No. 5,373,359 as it describes a Rotating Analyzer Ellipsometer System which utilizes white light. Patents continued from the 359 Woollam et al. Patent are, U.S. Pat. No. 5,504,582 to Johs et al. and U.S. Pat. No. 5,521,706 to Green et al. Said 582 Johs et al. and 706 Green et al. Patents describe use of polychromatic light in a Rotating Analyzer Ellipsometer System.

A Patent to Bernoux et al., U.S. Pat. No. 5,329,357 is identified as it describes the use of optical fibers as input and output means in an ellipsometer system.

A Patent to Chen et al., U.S. Pat. No. 5,581,350 is identified as it describes the application of regression in calibration of ellipsometer systems.

Additionally, Patents pertaining to optical elements, and particularly to compensators/retarders per se are:

U.S. Pat. No. 4,917,461 to Goldstein, describes an achromatic infrared retarder comprised of two identical prisms in combination with a rflective surface;

U.S. Pat. No. 4,772,104 to Buhrer which describes an achromatic optical filter comprised of two birefringent disks;

U.S. Pat. No. 4,961,634 to Chipman describes an infrared achromatic retarder comprised of Cds and CdSe plates aligned with the fast axes thereof perpendicular to one another;

U.S. Pat. No. 5,946,098 to Johs, Herzinger and Green, which describes numerous optical elements. In addition Patents to Johs et al. U.S. Pat. Nos. 6,084,674; 6,118,537; 6,100,981; 6,141,102; 6,100,981; 5,963,325; 6,084,674 and to Herzinger et al. U.S. Pat. No. 6,084,675, which Applications depend from application Ser. No. 08/997,311 filed Dec. 23, 1997, now said U.S. Pat. No. 5,946,098;

Additional Patents which describe Compensators are U.S. Pat. No. 548,495 to Abbe; U.S. Pat. No. 4,556,292 to Mathyssek et al.; U.S. Pat. No. 5,475,525 Tournois et al.; U.S. Pat. No. 5,016,980 Waldron; and U.S. Pat. No. 3,817,624 to Martin and U.S. Pat. No. 2,447,828 to West;

And, Patents to Robert et al., U.S. Pat. Nos. 4,176,951 and 4,179,217 are also disclosed as they describe rotating Birefringent elements in Ellipsometers which produce 2ω and 4ω components.

Regarding Articles, an article by Johs, titled "Regression a Calibration Method For Rotating Element Ellipsometers", which appeared in Thin Film Solids, Vol. 234 in 1993 is also identified as it predates the Chen et al. Patent and describes an essentially similar approach to ellipsometer calibration.

An article by Jellison Jr. titled "Data Analysis for Spectroscopic Ellipsometry", Thin Film Solids, 234, (1993) is identified as it describes a method for determining the accuracy with which certain data points can be measured, which information allows adding a weighting factor to a curve fitting regression procedure as applied to a multiplicity of data points, said weighting factor serving to emphasize the effect of more accurate and precise data.

An article by Collins titled "Automated Rotating Element Ellipsometers: Calibration, Operation, and Real-Time Applications", Rev. Sci. Instrum. 61(8), August 1990 is identified as it provides insight into rotating element ellipsometers.

An article by Kleim et al. titled "Systematic Errors in Rotating-Compensator Ellipsometry" published in J. Opt. Soc. Am./Vol. 11, No. 9, September 1994 is identified as it describes calibration of rotating compensator ellipsometers.

An Article by An and Collins titled "Waveform Analysis With Optical Multichannel Detectors: Applications for Rapid-Scan Spectroscopic Ellipsometer", Rev. Sci. Instrum., 62 (8), August 1991 is also identified as it discusses effects such as Detection System Error Characterization, Stray Light, Image Persistence etc., and calibration thereof.

Further identified as authority for Matrix Mathematics is a paper by Jones titled "A New Calculus For The Treatment Of Optical Systems", J.O.S.O., Vol. 31, (July 1941).

Identified as describing application of Mueller Matricies in Rotating Compensator Ellispometers which utilize imperfect compensators, is a paper by Hauge titled "Mueller Matrix Ellipsometry With Imperfect Compensators", J. Opt. Soc. Am., Vol. 68, No. 11, (November 1978).

A paper titled "Analysis of Specular and Textured $SnO_2$:F Films by High Speed Four-Parameter Stokes Vector Spectroscopy", Rovira & Collins, J. App. Phys., Vol. 85, No. 4, (1999).

Papers by Schubert and Schubert et al. which describe "Generalized Ellipsometry" are disclosed as they provide insight as how to Mathematically treat depolarizing Elements. Said Articles are: "Polarization Dependent Parametes of Arbitrary Anisotropic Homogeneous Epitaxial Systems", Phys. Rev. B 53, (1996); "Generalized Transmission Ellipsometry For Twisted Biaxial Dielectric Media: Application to Chiral Liquid Crystals", J. Opt. Soc. Am A, Vol 13, No. 9 (1996); and "Extrension of Rotating-Analyzer Ellipsometry to Generalized Ellipsometry: Determination of the Dielectric Function Tensor From Uniaxial $TiO2$", J. Opt. Soc. Am. A. 13, (1996).

A book by Azzam and Bashara titled "Ellipsometry and Polarized light" North-Holland, 1977 is disclosed and incorporated herein by reference for general theory.

As well, identified for authority regarding regression, is a book titled Numerical Recipes in "C", 1988, Cambridge University Press.

Even in view of the foregoing, a need remains for improved Spectroscopic Rotating Compensator Ellipsometer Systems, including a Photo Array, for simultaneously detecting a Multiplicity of Wavelengths, and which can be realized utilizing off-the-shelf, non-ideal, compensators and diode array spectrometers. As will be better disclosed in the Disclosure of the invention Section of this Specification, the invention provides a Spectroscopic Rotating Compensator Ellipsometer System which comprises a Psuedo-Achromatic Compensator, and discloses alternative use of D.C. and A.C data normalization in various calibration steps, as well as use of un-normalized signals in determining Reflectance.

DISCLOSURE OF THE INVENTION

First, it should be appreciated that the purpose of this Application is to achieve a Patent which clarifies the boundaries of what the Patents to Aspnes et al., U.S. Pat. Nos. 6,320,657 B1, 6,134,012, 5,973,787 and 5,877,859, (all assigned to Thermawave Inc.), cover as constrasted to what U.S. Pat. Nos. 5,706,212 and 5,872,630, and a Patent to Issue based on application Ser. No. 09/496,011 filed Feb. 1, 2000; (all assigned to J.A. Woollam Co. Inc.), cover. It is directly stated that it is believed that Thermawave has rights for application of "Substantially- Non-Achromatic" Compensators in Spectroscopic Rotating Compensator Ellipsometers, while the J.A. Woollam Co. Inc. has rights for application of "Substantially-Achromatic/Psuedo-Achromatic" Compensators in Spectroscopic Rotating Compensator Ellipsometers. This is partially based in that the priority of the Thermawave 859 Patent, (which discloses a Substantially-Non-Achromatic Retarder which provides a retardation range that passes through 180 degrees), is approximately 4 months later than the priority of the J.A. Woollam Co. 212 Patent, (which discloses a Substantially-Achromatic/Psuedo-Achromatic Retarder). The distinction between Achromatic and Substantially-Achromatic/Psuedo-Achromatic is that an Achromatic Retarder ideally provides the same retardation in all wavelengths over a range of wavelengths, while a Substantially Achromatic/Psuedo-Achromatic Retarder provides retardance over a range of wavelengths, which varies. The distinction between "Substantially-Non-Achromatic" and "Substantially-Achromatic/Psuedo-Achromatic" Retarders is that the former provide a retardation range which is, over a range of wavelengths, more than that provided by the later. It is believed that a good delineation line between Substantially-Non-Achromatic and Substantially-Achromatic/Psuedo-Achromatic Retarders is provided by the recitation in the Thermawave 012 Patent wherein it is stated that "an effective phase retardation value is induced covering at least from 90 decrees to 180 degrees", over a range of wavelengths. In the present Specification the terminology Substantially-Achromatic/Psuedo-Achromatic is used to identify a Compensator that provides a range of retardations, over a range of wavelengths, which range of retardations, (ie. maximum retardation minus minimum retardation), is less than 90 degrees. And the distinction between Substantially-Achromatic and Psuedo-Achromatic, for the purposes of this Specification is considered to be that the former provides a range of retardation values, over a range of wavelengths, greater than 0.0 degrees and merging into the range of a Psuedo-Achromatic Compensator which, for the purposes of this Specification can be considered as providing a magnitude of retardations less than the magnitude of "at least from 90 to 180 degrees", (eg. the retardation provided by a J.A. Woollam Co. Psuedo-Achromatic Compensator varies with wavelength over a range, (that is, maximum–minimum retardation), of less than 90 degrees, with a preferred lower boundary value retardation being at least 30 degrees, and an upper boundary value of retardation being less than 135 degrees). It is believed that the Thermawave Patents do not provide priority support for Claiming, in the context of a Rotating Compensator Spectroscope Ellipsometer, a retarder with other than Substantially-Non-Achromatic characteristics, while the J.A. Woollam Co. has priority support for Claiming Substantially-Achromatic/Psuedo-Achromatic Compensators applied in the context of a Rotating Compensator Spectroscopic Ellipsometer from the 212 and 630 Patents, with refined definition for Psuedo-Achromatic being provided by, for instance, the Allotted but still Co-pending application Ser. No. 09/496,011, which was filed Feb. 1, 2000.

Moving along, as described in the 630 Patent, prior thereto it was generally considered that while Rotating Compensator Ellipsometers Systems provide many benefits, (eg. Material System, (Sample), PSI and DELTA investigation limiting "dead-spots" are not present), that in the absence of essentially Achromatic "ideal" Compensators it would be prohibitively difficult and expensive to build, calibrate and utilize a "Spectroscopic" Rotating Compensator Ellipsometer Material System Investigating System. This is to be understood in light of the fact that Compensator Means which are essentially Achromatic, (ie. provide essentially constant retardation, (ie. very small retardation range), over a large range of Wavelengths, such as from, less than or equal to 190, to 1000 or higher (eg. 1800 nm), nanometers), are not generally and economically available as off-the-shelf items, (this being particulalry true where a Compensator is rotated during use).

In the terminology of the 630 Patent, the disclosed invention system is, however, an affordable, easy to calibrate and utilize Spectroscopic Rotating Compensator Material System Investigation System comprising a Source of a Polychromatic Beam of Electromagnetic Radiation, a Polarizer, a Stage for Supporting a Material System, (Sample), an Analyzer, a Dispersive Optics and at least one Photo Array Detector Element System which contains a multiplicity of Detector Elements, which Spectroscopic Rotating Compensator Material System Investigation System further comprises at least one Compensator(s) positioned at a location selected from the group consisting of: (before said stage for supporting a Material System, (Sample), and after said stage for supporting a Material System, (Sample), and both before and after said stage for supporting a Material System (Sample).

While the preferred embodiment of the disclosed invention utilizes Psuedo-Achromatic Compensators, technically of interest is the fact that said at least one Compensator(s) utilized in the disclosed invention can technically be essentially any available, reasonably priced, off-the-shelf Retardation providing system, including non-Achromatic Berek-type, Zero-Order Waveplate, Multiple-Order Waveplate, Zero-Order Waveplate constructed from Multiple Multiple-Order Waveplates, Sequential Systems of Multiple Zero-Order Waveplates, each of which can be constructed from Multiple Multiple-Order Waveplates, Polymer Retarder, Mica Waveplate, Freshnel Rhomb, Achromatic, and Pseudo-Achromatic, etc. For general information, it is noted that a Berek-type Compensator is a uniaxially anisotropic plate of material in which the Optical Axis is oriented perpendicularly to a plate surface thereof. When a Polarized Beam of Electromagnetic Radiation is caused to be incident other than along the Optical Axis, orthogonal components thereof encounter different effective Indicies of Refraction, thereby effecting retardation therebetween. Polymer Compensators are made of a polymer material and can provide true Zero-Order retardance which, as do many Compensators, provides an inverse wavelength functional Retardance Characteristic. Essentially Achromatic (Pseudo-Achromatic) Compensators can be constructed by stacking appropriately chosen Polymer and Crystal waveplates.

Sequential Systems of Multiple Zero-Order Waveplates allow achieving flattened Retardance vs. wavelength characteristics, (ie. smaller retardation range), and it is noted, are the preferred disclosed invention Compensator type. To ellaborate, the preferred Compensator system comprises a system of at least two (eg. First and Second), Zero-Order Waveplates, each of which Zero-Order Waveplates can be a single plate, (eg. mica or polymer), or constructed from an effective combination of Multiple-Order Waveplates, (eg. two quartz plates or bicrystaline waveplates such as Cadmium Sulfide or Cadmium Selenide). As further insight, an effective Zero-Order Waveplate can be functionally constructed by combining two Multi-Order (eg. Quartz) Waveplates which have Optical Axes oriented at a nominal ninety (90) degrees with respect to one another. That is, two Multi-Order waveplates are selected and combined so that the difference in retardation entered by each gives rise to an overall Zero-Order Waveplate retardance characteristic. In particular, the prefered invention Compensator embodiment provides that each of said First and Second effectively Zero Order Waveplates be formed by physically optically combining two Multiple Order Waveplates, such that the net result of passing a beam of electromagnetic radiation therethrough is essentially equivalent to the result which would achieved by passing said electromagnetic beam through a single plate Zero-Order Waveplate. The reason that such effective Zero-Order Waveplates, which are formed by physically combining two Multiple Order Waveplates are preferred, is that such effectively Zero-Order Waveplates are readily and economically available in the marketplace, and that true single plate Zero-Order Waveplates are typically physically delicate and difficult to utilize. Continuing, the preferred invention Compensator provides that two of said per se., or effective Zero-Order Waveplate Compensators, be oriented with respect to one another such that the fast axes of the First per se. or effectively Zero-Order Compensator are rotated with respect to the Second per se. or effectively Zero-Order Compensator, away from zero or ninety degrees, and typically within some range around a nominal forty-five (45) degrees. In use, a beam of electromagnetic radiation utilized to investigate a material system, is caused to pass through both of said First and Second Compensators with the result achieved being that a disclosed invention preferred Compensator configuration provides a pseudo-achromatic retardation range, (ie. max–min), of less than 90 degrees within a range of retardations bounded by a lower bound of at least thirty (30) and an upper bound of less one-hundred-thirty-five (135) degrees, over relatively large wavelength ranges within, for instance, one-hundred-ninety (190 NM) to eighteen-hundred (1800 NM). That is, preferred invention Compensators are specifically designed to provide retardation values which never equal or exceed one-hundred-eighty (180) degrees, or even one-hundred-thirty-five (135) degrees at any utilized wavelength. It is noted that this is in direct contrast to the practice of Therma-wave rotating compensator systems as described in U.S. Pat. Nos. 6,320,657 B1, 6,134,012, 5,973,787 and 5,877,859 to Aspnes, wherein large chromaticities, (eg. at least 90–180 degrees retardation range over a range of wavelengths), in compensator systems utilized cover a range of retardations which the Specifications indicate can include 180 degrees therewithin, emphasis added.

In terminology similar to that used in the Aspnes et al. Patents, which describe spectroscopic ellipsometer systems comprising substantially non-achromatic compensators, the presently disclosed invention can be described as:

A spectroscopic ellipsometer for evaluating a sample comprising:

a broadband light source generating a beam having wavelengths extending over a range of at least 200 to 800 nm;

a polarizer disposed in the path of the light beam;

a compensator disposed in the path of the light beam, said compensator for inducing phase retardations in the polarization state of the light beam, said compensator having characteristics selected from the group consisting of:

being substantially achromatic;

being pseudo-achromatic; and being other than substantially non-achromatic;

so that the amount of phase retardation varies with wavelength, over a range of wavelengths, less than is the case were a substantially-non-achromatic compensator utilized, said compensator means being rotated at an angular frequency of $\omega$;

an analyzer that interacts with the light beam after the beam interacts with the sample and with the compensator;

a detector means that measure the intensity of the light beam after the interaction with the analyzer at a plurality of wavelengths across the wavelength range of at least 200 to 800 nm;

said detector means generating a time varying intensity output signal simultaneously comprising $2\omega$ and $4\omega$ component signals; and optionally a processor for evaluating the sample based on simultaneous use of the intensity output signal $2\omega$ and $4\omega$ components.

(It is to be noted that the present Application is a CIP from application Ser. No. 08/618,820 filed Mar. 20, 1996, (now U.S. Pat. No. 5,706,212), which disclosed a spectroscopic ellipsometer sytem which was disclosed as preferably comprising a substantially achromatic compensator).

Another recitation of the presently disclosed invention, which focuses on the presence of a Psuedo-Achromatic Compensator, is:

A spectroscopic ellipsometer for evaluating a sample comprising:

polychromatic electromagnetic radiation source means generating a beam having wavelengths extending over a range of at least 200 to 800 nm;

polarizer means disposed in the path of said beam;

compensator(s) means disposed in the path of the beam, said compensator for inducing phase retardations in the polarization state of the light beam, said compensator(s) means being:

pseudo-achromatic;

in that the amount of phase retardation varies more with wavelength than is the case if a substantially achromatic compensator is utilized but in that the amount of phase retardation varies less than is the case if a substantially non-achromatic compensator is utilized, said compensator means being rotated at an angular frequency of $\omega$;

analyzer means that interacts with the beam after the beam interacts with the sample and the compensator means;

detector means that measure the intensity of the beam after the interaction with the analyzer at a plurality of wavelengths across the wavelength range of at least 200 to 800 nm;

said detector means generating a time varying intensity output signal simultaneously comprising $2\omega$ and $4\omega$ component signals, said $2\omega$ and $4\omega$ signals being simultaneously present at all wavelengths measured unless the $2\omega$ signal is forced to 0.0 by a sample presenting with an ellipsometric DELTA of 0.0, as opposed to being caused to be 0.0 by said compensator means; and optionally a processor for evaluating the sample based on simultaneous use of the intensity output signal $2\omega$ and $4\omega$ components.

Further, for the purposes of this Specification, the definition of "other than substantially non-achromatic" includes the requirement that the range of retardations entered to wavelengths over a range of wavelengths does not include one-hundred-eights (180) degrees.

(Note in both the foregoing recitations, in contrast to the teachings of the Aspnes et al. U.S. Pat. Nos. 6,320,657 B1, 6,134,012, 5,973,787 and 5,877,859, the compensator means in a disclosed invention system can not force the $2\omega$ signal to (0.0), as it is selected to provide, at any wavelength, far less than 180 degrees retardation, (eg, greater than 30 up to 120 degrees; or 35 to less than 125; or 45 degrees to less than 135 degrees etc.), regardless of which wavelength in the polychromatic range of wavelengths of at least 200 to 800 nm, (eg. 190–1800 nm), is investigated. Note, in any case the range of retardation values entered to wavelengths over a range thereof is less than ninety (90) degrees and does not include 180 degrees. Further, it is to be understood the terminology "Compensator" means include the case of a disclosed invention system being comprised of a Single Compensator or Multiple Compensator Elements).

Continuing, the disclosed invention system preferably utilizes at least one compensator means which is described as a selection from the group consisting of:

being comprised of at least two zero-order waveplates, said zero-order waveplates having their respective fast axes rotated to a position offset from zero or ninety degrees with respect to one another;

being comprised of a combination of at least a first and a second effective zero-order wave plate, said first effective zero-order wave plate being comprised of two multiple order waveplates which are combined with the fast axes thereof oriented at a nominal ninety degrees to one another, and said second effective zero-order wave plate being comprised of two multiple order waveplates which are combined with the fast axes thereof oriented at a nominal ninety degrees to one another; the fast axes of the multiple order waveplates in said second effective zero-order wave plate being rotated to a position at a nominal forty-five degrees to the fast axes of the multiple order waveplates in said first effective zero-order waveplate;

being comprised of a combination of at least a first and a second effective zero-order wave plate, said first effective zero-order wave plate being comprised of two multiple order waveplates which are combined with the fast axes thereof oriented at a nominal ninety degrees to one another, and said second effective zero-order wave plate being comprised of two multiple order waveplates which are combined with the fast axes thereof oriented at a nominal ninety degrees to one another; the fast axes of the multiple order waveplates in said second effective zero-order wave plate being rotated to a position away from zero or ninety degrees with respect to the fast axes of the multiple order waveplates and in said first effective zero-order waveplate;

being comprised of at least one zero-order waveplate and one effective zero-order waveplate, said effective zero-order wave plate being comprised of two multiple order waveplates which are combined with the fast axes thereof oriented at a nominal ninety degrees to one another, the fast axes of the multiple order waveplates in said effective zero-order wave plate being rotated to a position away from zero or ninety degrees with respect to the fast axis of the zero-order waveplate.

(Note, zero-order and effective zero-order waveplates are of, for instance, single plate and multiple waveplate construction respectively).

(It is also noted that generally the more elements combined to form a compensator, the smaller can be made the range over which retardation values vary with wavelength, over a range of wavelengths. For instance three (3) elements are utilized in some J.A. Woollam CO. Psuedo-Achromatic Compensators which operate over a major part of the range of 190–1700 nm).

Continuing, because the preferred disclosed invention Compensators do not provide an exact Ninety (90) Degrees of Retardation at all wavelengths over a relatively large range of Wavelengths, the presently disclosed invention, as described herein, utilizes a Regression based Calibration procedure which compensates for said non-ideal Compensator Retardation characteristics. And while it is true that the sensitivity and accuracy of a Rotating Compensator Material System investigation System degrades as the Retardance provided by a utilized Compensator approaches zero (0.0) or one-hundred-eighty (180) degrees, again, it has been found that Compensators which demonstrate a Retardation range of less than Ninety (90) degrees (max–min) over a range of utilized Wavelengths, within in a range bounded by at least Thirty (30) and less than one-hundred-thirty-five (135) degrees, (thereby avoiding the U.S. Pat. Nos. 6,320,657 B1, 6,134,012, 5,973,787 and 5,877,859 to Aspnes et al.), are available, or can be constructed from readily available components, which are very acceptable for use in the disclosed invention Rotating Compensator Ellipsometer System, and said Compensators enable achieving very impressive results over a demonstrated relatively large range of wavelengths, (eg. at least two-hundred-fifty (250) to one-thousand (1000) or more nanometers). One embodiment of the spectroscopic rotating compensator material system investigation system typically comprises at least one compensator(s) which produces a retardance of, preferably, between seventy-five (75) and one-hundred-thirty (130) degrees over a range of wavelengths defined by a selection from the group consisting of:

a. between one-hundred-ninety (190) and seven-hundred-fifty (750) nanometers;
b. between two-hundred-forty-five (245) and nine-hundred (900) nanometers;
c. between three-hundred-eighty (380) and seventeen-hundred (1700) nanometers;
d. within a range of wavelengths defined by a maximum wavelength (MAXW) and a minimum wavelength (MINW) wherein the ratio of (MAXW)/(MINW) is at least one-and-eight-tenths (1.8).

Acceptable practice however, provides for the case wherein at least one of said at least one compensator(s) provides range of Retardation of less than Ninety (90) degrees (max–min) over a range of utilized Wavelengths between MINW and MAXW, within in a range bounded by at least Thirty (30) and less than one-hundred-thirty-five (135) degrees, said wavelength range being specified by a selection from the group consisting of:

a. MINW less than/equal to one-hundred-ninety (190) and MAXW greater than/equal to seventeen-hundred (1700) nanometers;
b. MINW less than/equal to two-hundred-twenty (220) and MAXW greater than/equal to one-thousand (1000) nanometers;
c. within a range of wavelengths defined by a maximum wavelength (MAXW) and a minimum wavelength (MINW) range where (MAXW)/(MINW) is at least four-and-one-half (4.5).

(NOTE, the specified values and ranges can not be achieved by At single plates with Substantially Non-Achromatic, (eg. 1/wavelength), retardation characteristics, but can be achieved by two (2) and three (3) plate Compensator designs).

Continuing, when the disclosed invention Spectroscopic Rotating Compensator Material System Investigation System, (ie. Spectroscopic Ellipsometer), is used to investigate a Material System, (ie. Sample), present on said Stage for Supporting a Material System, (Sample), said Analyzer Means and Polarizer Means are maintained essentially fixed in position and at least one of said at least one Compensator (s) Means is/are caused to continuously rotate while a Polychromatic, (Broadband), Beam of Electromagnetic Radiation produced by said Source of a Polychromatic Beam of Electromagnetic Radiation is caused to pass through said Polarizer and said Compensator Means. Said Polychromatic Beam of Electromagnetic Radiation is also caused to interact with said Material System, (Sample), pass through said Analyzer Means and interact with said Dispersive Optics such that a Multiplicity of Essentially Single Wavelengths are caused to simultaneously enter a corresponding multiplicity of Detector Elements in said Detector System Photo Array.

In language again similar to that in the Aspnes et al. Patents, a method of calibrating a Spectroscopic Ellipsometer System can comprise the steps of:

a. providing a spectroscopic ellipsometer for evaluating a sample comprising:

broadband electromagnetic radiation source means generating a beam having wavelengths extending over a range of at least 200 to 800 nm;

polarizer means disposed in the path of said beam;

compensator means disposed in the path of the beam, said compensator for inducing phase retardations in the polarization state of the light beam, said compensator means having characteristics other than substantially non-achromatic, said compensator means being rotated at an angular frequency of ω;

analyzer means that interact with the beam after the beam interacts with the sample and the compensator means;

detector means that measure the intensity of the beam after the interaction with the analyzer means at a plurality of wavelengths across the wavelength range of at least 200 to 800 nm;

said detector means generating a time varying intensity signal simultaneously comprising 2ω and 4ω component signals, said 2ω and 4ω signals being simultaneously present at all wavelengths measured unless the 2ω signal is forced to 0.0 by a sample presenting with an ellipsometric DELTA of 0.0 as opposed to being caused to be 0.0 by said compensator means;

b. developing a mathematical model of said spectroscopic ellipsometer system which comprises as calibration parameter(s) at least one selection from the group consisting of:

effective polarizer means azimuthal angle orientation;

present sample PSI ($\Psi$), as a function of angle of incidence and a thickness;

present sample DELTA ($\Delta$), as a function of angle of incidence and a thickness;

retardations of said compensator means as a function of wavelength;

compensator means azimuthal angle orientation;

matrix components of said compensator means; and analyzer means azimuthal angle orientation;

which mathematical model is effectively a transfer function which enables calculation of electromagnetic beam magnitude detected by a detector element, given magnitude provided by said broadband electromagnetic radiation source means generating a beam having wavelengths extending over a range of at least 200 to 800 nm;

c. causing a polychromatic beam of electromagnetic radiation produced by said broadband electromagnetic radiation source means, to pass through said polarizer means, interact with a sample caused to be in the path thereof, pass through said analyzer means, and enter detector elements in said detector means, with said polychromatic beam of electromagnetic radiation also being caused to pass through said compensator means;

d. obtaining data as described by a selection from the group consisting of:

at least one multi-dimensional data set(s); and least two, at least one-dimensional data sets;

said data set(s) being magnitude values vs. parameter(s) selected from the group consisting of:

wavelength;

angle-of-incidence of said polychromatic beam of electromagnetic radiation with respect to a present material system;

effective or actual azimuthal angle orientation of one element selected from the group consisting of:

said polarizer; and said analyzer;

obtained over time, while at least one of said at least one compensator is caused to continuously rotate;

said at least at least one, multi-dimensional data set(s) being obtained utilizing a selection from the group consisting of:

all of said at least one multi-dimensional data set(s), being obtained utilizing a single sample;

at least one of said at least one multi-dimensional data sets being obtained utilizing one sample, with another of said at least one multi-dimensional data sets being obtained utilizing another sample; and at least one of said at least one multi-dimensional data set(s) being obtained with the spectroscopic ellipsometer oriented in a "straight-through" configuration wherein a polychromatic beam of electromagnetic radiation produced by said broadband electromagnetic radiation source means, generating a beam having wavelengths extending over a range of at least 200 to 800 nm, is caused to pass through said polarizer means, pass through said analyzer means and enter detector elements in said at least one detector system, with said polychromatic beam of electromagnetic radiation also being caused to pass through said compensator means but without being caused to interact with any sample other than open ambient atmosphere;

e. normalizing data in each said at least one, multi-dimensional, data set(s) with respect to a selection from the group consisting of:

a data set D.C. component;

a data set A.C. component;

a parameter derived from a combinations of a data set D.C. component and a data set A.C. component;

f. performing a mathematical regression of said mathematical model onto said normalized at least one, multi-dimensional, data set(s), thereby evaluating calibration parameters in said mathematical model;

said regression based calibration procedure serving to evaluate parameters in said said mathematical model for non-achromatic characteristics and/or non-idealities and/or positions of at least one selection from the group consisting of:

effective azimuthal angle of said polarizer means;

azimuthal angle of said compensator means, retardation of said compensator means;

matrix components of said compensator means;

depolarization/Mueller Matrix components; and azimuthal angle of said analyzer means.

g. optionally repeating steps e. and f. utilizing a different selection in step e. in normalizing data.

Continuing, the 630 Patent Method of Calibrating a Spectroscopic Rotating Compensator Material System Investigation System describes, in the step of calculating values of Coefficients of a Transfer Function from said Data Set, the calculation of values of Coefficients of a Fourier Series, (eg. $\alpha_1$, $\alpha_4$, $\beta_2$, $\beta_4$, in Eqs. 11–14 supra).

Additionally, said 630 Patent Method of Calibrating a Spectroscopic Rotating Compensator Material System Investigation system can further comprise the step of Parameterizing Calibration Parameters by representing variation as a function of Wavelength, (or perhaps Angle-of-Incidence of said Polychromatic Beam of Electromagnetic Radiation with respect to a Surface of an Investigated Material System, (Sample), or Other Variable), by a Calibration Parameter containing Mathematical Equation, Calibration Parameter(s) in said Calibration Parameter containing Mathematical Equation being evaluated during said Mathematical Regression. (See Eqs. 50 & 51 below). When this is done the Calibration Parameter containing Mathematical Equation provides a functional relationship, and, it is noted, can even be a constant value over a range of, for instance, Wavelengths and/or Polarizer Azimuthal Angle settings). (Note, said parameterized approach to mathematical regression based calibration parameter evaluation is better described supra herein under the Headings GLOBAL REGRESSION MODES 1, 2 and 3).

It is further noted that the at least Two Dimensional Data Set can be obtained with the Spectroscopic Rotating Compensator Material System Investigation System oriented in a "Straight-Through" or "Material-System-(Sample)-Present" configuration. In the first configuration open atmosphere essentially constitutes a material system, and a Polarized Electromagnetic Beam passes directly through the Polarizer, Compensator(s) and Analyzer into the Detector System. In the second configuration a Material System, (Sample), is present which presents PSI and DELTA values other than those of the open atmosphere so that a Polychromatic Electromagnetic Beam passes through the Polarizer, possibly a Compensator, and then interacts with a Material System, (Sample), before passing through, possibly a Compensator, an Analyzer and into the Detector System. Compensator(s), it should be understood, can be present before and/or after the Material System, (Sample).

With the above general description of the disclosed invention System and Calibration Method in mind, attention is directed to providing a detailed demonstration of the Calibration Procedure of the disclosed invention as applied to a Spectroscopic Rotating Compensator Ellipsometer System sequentially comprised of:

Polychromatic Light Source
Fixed Polarizer Means
Material Sample, (Sample)
Continuously Rotating Compensator Means
Fixed Analyzer Means, and
Detector Element containing Photo Array.

(Note: the Reflection mode side of FIG. 1 of this Disclosure shows this basic configuration where Compensator Means (C) is considered as removed and only Compensator Means (C') remains present).

It is to be appreciated, however, that the basic approach to calibration described directly, is adaptable for use in systems in which the Continuously Rotating Compensator is placed ahead of a Material System, (Sample), and in systems in which two Compensators are present, one ahead of, and one after a Material System (Sample), wherein one or both are caused to Continuously Rotate in use. For instance, in the case where a Rotating Compensator is placed ahead of the Material System, (Sample), rather than thereafter, simply exchanging references to Polarizer and Analyzer in equations derived for the case where the Rotating Compensator is placed after the Material System, (Sample), provides the applicable equations.

Transfer function equations for the Rotating Compensator system configured as recited above can be obtained from multiplication of Matrix Representations of the various components, in an appropriate order, in conjunction with Trig function containing Rotation Matrices, which serve to align coordinate systems between components. Eq. 1 shows said Matrix representation:

$$E(P, \Psi, \Delta, C, r1, r2, r3, r4, A)^m \begin{pmatrix} 1 & 0 \\ 0 & 0 \end{pmatrix}. \tag{1}$$

$$\begin{pmatrix} \cos(A) & \sin(A) \\ -\sin(A) & \cos(A) \end{pmatrix} \cdot \begin{pmatrix} \cos(C) & -\sin(C) \\ \sin(C) & \cos(C) \end{pmatrix} \cdot \begin{pmatrix} r1 & r3 \\ r2 & r4 \end{pmatrix} \cdot$$

$$\begin{pmatrix} \cos(C) & \sin(C) \\ -\sin(C) & \cos(C) \end{pmatrix} \cdot \begin{pmatrix} \sin\Psi \cdot e^{ti\cdot\Delta} & 0 \\ 0 & \cos\Psi \end{pmatrix} \cdot \begin{pmatrix} \cos(P) \\ \sin(P) \end{pmatrix}$$

where: $\Psi$ and $\Delta$ are the traditional ellipsometric parameters which describe the Material System, (Sample);

P is the azimuthal orientation of the Polarizer;
C is the azimuthal orientation of the Rotating Compensator;
r1, r2, r3 & r4 are the Jones Matrix elements which describe the Compensator, (Note that a Jones Matrix is utilized, however, a Mueller Matrix or other Matrix could also be utilized);
A is the azimuthal orientation of the Analyzer.

The Light Intensity which is measured by a Detector is provided by multiplying through the Matrices in Eq. 1 to provide a Complex Result, then multiplying said Complex Result by its Complex Conjugate. Eq. 2 indicates this:

$$I(P,\Psi,\Delta,C,r1,r2,r3,r4,A)=E(P,\Psi,\Delta,C,r1,r2,r3,r4,A)\cdot E^*(P,\Psi,\Delta,C,r1,$$

$$r2,r3,r4,A) \tag{2}$$

The Intensity Equation I(t), (Eq. 8):

$$I(t)=I_0(DC+\alpha_2 \cos 2C+\beta_2 \sin 2C+\alpha_4 \cos 4C+\beta_4 \sin 4C) \tag{8}$$

which results from said multiplication is very involved, but can be expressed in terms of intermediate results as provided in Eq. 3–7, via Eqs. 9.

$$p1=\sin \Psi \cdot (\cos \Delta + i \sin \Delta) \cdot \cos P$$

$$p2=\cos \Psi \cdot \sin P \tag{3}$$

$$K1=(p1 \cdot r3+p2 \cdot r1)$$

$$K2=(p1 \cdot r1+p2 \cdot r3)$$

$$K3=(p1 \cdot r4+p2 \cdot r2)$$

$$K4=(p1 \cdot r2+p2 \cdot r4) \tag{4}$$

$$U1=(\cos(A) \cdot K2+\sin(A) \cdot K4)$$

$$U2=(K3+K2) \cdot \sin(A)+(K1-K4) \cdot \cos(A)$$

$$U3=(\cos(A) \cdot K3+\sin(A) \cdot K1) \tag{5}$$

$$V1=U1 \cdot \overline{U1} \quad V2=U2 \cdot \overline{U2} \quad V3=U3 \cdot \overline{U3}$$

$$V1=2 \cdot Re(U1 \cdot \overline{U2})V5=2 \cdot Re(U1 \cdot \overline{U3})V6=2 \cdot Re(U2 \cdot \overline{U3}) \tag{6}$$

$$T1=V1+V3 \quad T2=V2+V5 \quad T3=V1-V3$$

$$T4=V4+V6 \quad T5=V4-V6 \tag{7}$$

where Eqs. 9 provide that:

$$DC=3/8T1+1/8T2$$

$$\alpha_2=1/2T3 \quad \beta_2=1/4T4$$

$$\alpha_4=1/8(T1\ T2)\beta_4=1/8T5 \tag{9}$$

and C=ω·t, where 'ω' is the angular frequency of the continuously rotating Compensator and I0 is an arbitrary constant.

(It is further noted that Eq. 8 is a truncated Fourier Series, and could include additional, higher harmonic terms).

Equations 1–9 are appropriate for a Material System, (Sample), which does not depolarize an Electromagnetic Beam used to investigate a Material System, (Sample), such that Jones Matrix formalism is appropriate. If a Material System, (Sample), is investigated which does depolarize an investigation electromagnetic beam, then Mueller Matrix formalism can be substituted. As well, the "Isotropic" Material System, (Sample), Matrix in Eq. 1 could be replaced by a General Material System, (Sample), Matrix. This is described by M. Schubert in the context of "Generalized Ellipsometry", (see Background Section for citations to relevant articles which treat the topic of Generalized ellipsometry by Schubert).

If an ideal Compensator is assumed, where the Jones Matrix components are:

r1=1;
r2=0;
r3=0; and
r4=$e^{i\cdot\delta}$;

then the Eqs. 9 become Eqs.10–14:

$$DC=(1/2)(1+\cos \delta)[\cos 2A(\cos 2P-\cos 2\Psi)+\sin 2A \sin 2P \sin 2\Psi$$

$$\cos \Delta]-\cos 2P \cos 2\Psi+1 \tag{10}$$

$$\alpha_2=-\sin 2A \sin 2P \sin \delta \sin 2\Psi \sin \Delta \tag{11}$$

$$\beta_2 = -\cos 2A \sin 2P \sin \delta \sin 2\Psi \sin \Delta \tag{12}$$

$$\alpha_4 = (1/2)(1-\cos \delta)[\cos 2A(\cos 2P - \cos 2\Psi) - \sin 2A \sin 2P \sin 2\Psi \cos \Delta] \tag{13}$$

$$\beta_4 = (1/2)(1-\cos \delta)[\sin 2A(\cos 2P - \cos 2\Psi) + \cos 2A \sin 2P \sin 2\Psi \cos \Delta] \tag{14}$$

It is noted that said Eqs. 10–14 are found in Kleim et al. as referenced in the Background Section of this Specification, with "A" and "P" interchanged. (The Kleim et al. work assumed a Rotating Compensator present prior to a Material System, (Sample)).

Continuing, Eqs. 10–14 are valid for an ideal Rotating Compensator System wherein the Azimuthal angles of the optics are perfectly aligned with the Material System, (Sample), frame of reference. In practice this is never true, and offset terms "A'", "P'" and "C'" must be entered to provide Eqs. 15a and 15b:

$$A = A' - A_s, \quad P = P' - P_s \tag{15a}$$

$$C = C' - C_s \tag{15b}$$

where the A', C' and P' indicate dial readings and the As, Cs and Ps indicate Offset Angles to be determined by a Calibration Procedure.

Substituting Eq. 15b into Eq. 8 provides Eqs. 16a and 16b, and 17a and 17b for Fourier Coefficients, (note that the DC term is unchanged):

$$m\alpha_2 = \alpha_2 \cos 2C_s - \beta_2 \sin 2C_s \tag{16a}$$

$$m\beta_2 = \alpha_2 \sin 2C_s + \beta_2 \cos 2C_s \tag{16b}$$

$$m\alpha_4 = \alpha_4 \cos 4C_s - \beta_4 \sin 4C_s \tag{16c}$$

$$m\beta_4 = \alpha_4 \sin 4C_s + \beta_4 \cos 4C_s \tag{16d}$$

Continuing, the disclosed invention simultaneously measures the Intensity, (any functionally similar magnitude to be considered equivalent for the purposes of this disclosure), vs. time or compensator rotation angle of a multiplicity of essentially single wavelengths with a Photo Array, to determine Fourier Coefficients. And as the Diode Elements in the Photo Array are operated in a Charge Integration Mode, it is necessary to utilize a Hadamard analysis of the signal. In the embodiment of the invention disclosed in the Parent U.S. Pat. No. 5,872,630, the Diode Array was disclosed as synchronously read-out exactly sixteen (16) times during each rotation of the Rotating Compensator. (See supra herein wherein it is reported that presently preferred practice is to read-out a photo-array an odd number, (eg. thirteen (13) times), during each rotation of the Rotating Compensator). The time varying signal, which results from modulation imposed by the Rotating Compensator, is given by Eq. 18. Eq. 19 represents a measured value at a given channel in a Photo Array for the i'th scan measured during the rotation.

$$s(t) = I_0 \cdot (DC + \alpha_2 \cos 2t + \beta_2 \sin 2t + \alpha_4 \cos 4t + \beta_4 \sin 4t) \tag{18}$$

$$h_i = \int_{(i-1) \cdot \frac{\pi}{8}}^{i \cdot \frac{\pi}{8}} s(t) dt \tag{19}$$

Substituting Eq. 18 into Eq. 19 and rearranging terms provides the following expressions, (Eqs. 20–24), for the Fourier Coefficients:

$$DC = \frac{h_1 + h_2 + h_3 + h_4 + h_5 + h_6 + h_7 + h_8 + h_9 + h_{10} + h_{11} + h_{12} + h_{13} + h_{14} + h_{15} + h_{16}}{4 \cdot \pi \cdot I_0} \tag{20}$$

$$\alpha_2 = \frac{h_1 + h_2\ h_3 - h_4 - h_5 - h_6 + h_7 + h_8 + h_9 + h_{10} - h_{11} - h_{12} - h_{13} - h_{14} + h_{15} + h_{16}}{8 \cdot I_0} \tag{21}$$

$$\beta_2 = \frac{h_1 + h_2 + h_3 + h_4 - h_5 - h_6 - h_7 - h_8 + h_9 + h_{10} + h_{11} + h_{12} - h_{13} - h_{14} - h_{15} - h_{16}}{8 \cdot I_0} \tag{22}$$

$$\alpha_4 = \frac{h_1 - h_2 - h_3 + h_4 + h_5 - h_6 - h_7 + h_8 + h_9 - h_{10} - h_{11} + h_{12} + h_{13} - h_{14} - h_{15} + h_{16}}{8 \cdot I_0} \tag{23}$$

$$\beta_4 = \frac{h_1 + h_2\ h_3\ h_4 + h_5 + h_6 - h_7 - h_8 + h_9 + h_{10} - h_{11} - h_{12} + h_{13} + h_{14} - h_{15} - h_{16}}{8 \cdot I_0} \tag{24}$$

Equations 20–24 provide means for extracting the Fourier Coefficients for the Rotating Compensator modulated signal from the $(h_i)$ values which are measured by the Photo Array Diode Elements during continuous rotation of the Rotating Compensator.

The foregoing Eqns. 18–24, and associated text, provides disclosure regarding application of Hadamard Analysis in Parent U.S. Pat. No. 5,872,630. At this point, regarding Hadamard Analysis, it is disclosed that since said 630 Patent disclosure was formulated, additional work has provided insight to a method for determining Hadamard Coefficients for an arbitrary "n"-point Hadamard Transform. It is noted that current practice is to select "n" to be an odd number of at least nine (9), (rather than the previously recited value of sixteen (16)), and preferably thirteen (13). This allows acounting for not only D.C. and even harmonics, (eg. second (2nd) and forth (4th) which appear in invention output signals), but also for odd harmonics (eg. fifth (5th) and seventh (7th)), and the results of electronics non-linearities. In any case, it is emphasized that prefered practice teaches that "n" should be selected to be an odd number.

Continuing, disclosed invention practice provides that that for a given sampling period, application of the Hadamard analysis leads to calculation of the D.C. Signal Intensity, plus Sin and Cos Terms at (n−1)/2 harmonic frequencies. Consider that all measured points are indexed by a variable "1", while "ic" and "is" index the Cos and Sin components, respectively, and "j" indexes harmonic frequency components.

Consider, for (n=9):

$$i = 0 \ldots n-1;$$

$$ic = 1, 3 \ldots n-1$$

$$is = 2, 4 \ldots n-1;$$

$$j = 0 \ldots \frac{(n-1)}{2}.$$

Sin and Cos Basis Functions are piecewise integrated using Hadamard Formalism. The resulting Coefficients are then packed into a Square Matrix denoted "M", as indicated in Eqs. 19':

$$hc(i, j) := \int_{\frac{2\pi}{n} \cdot i}^{\frac{2\pi}{n} \cdot (i+1)} \cos(j \cdot t) dt \qquad (19')$$

$$hs(i, j) := \int_{\frac{2\pi}{n} \cdot i}^{\frac{2\pi}{n} \cdot (i+1)} \sin(j \cdot t) dt$$

$$M_{t,0} := hc(i, 0) \quad M_{t,tc} := hc\left(i, \text{floor:} \frac{ic}{2}\right) + 1$$

$$M_{t,ts} := hs(i, \text{floor})\frac{is}{2}.$$

The "M" Matrix is then inverted, yielding $$H := M^{-1}$$

a Matix of Coefficients "H" which can be applied to a general n-point data system stream to evaluate the "n" frequency components, ((D.C.+Sin+Cos terms at (n−1)/2 frequencies).

To extract the Eq. 18 frequency components of s(t), the signal is piecewise integrated, the resulting coefficients stored in "h", and multiplied times the Hadamard Ceofficient Matrix "H", as indicated in Eqs. labeled 20'–24' below:

As an example, consider the signal 's(t)' below which contains a DC value of 2.5, a 2nd harmonic 'cos' term of −6.1, and a 4th harmonic 'sin' term of 1 4.

$$s(t) := 2.5 + -6.1 \cdot \cos(2 \cdot t) + 1.4 \cdot \sin(4\ t)$$

To extract the frequency components of s(t), the signal is piecewise integrated (the resultin coefficients are stored in 'h'), and multiplied times the Hadamard coefficient matrix 'H'.

$$h_i = \int_{\frac{2\pi}{n} \cdot 1}^{\frac{2\pi}{n} \cdot (i+1)} s(t) dt \qquad 20'-24'$$

$$11h = \begin{bmatrix} 2.5 \\ 0 \\ 0 \\ -6.1 \\ 0 \\ 0 \\ 0 \\ 0 \\ 14 \end{bmatrix} \begin{array}{l} \text{DC component} \\ \text{1st harmonic, 'cos' component} \\ \text{1st harmonic, 'sin' component} \\ \text{2nd harmonic, 'cos' component} \\ \text{2nd harmonic, 'sin' component} \\ \text{3rd harmonic, 'cos' component} \\ \text{3rd harmonic, 'sin' component} \\ \text{4th harmonic, 'cos' component} \\ \text{4th harmonic, 'sin' component} \end{array}$$

As in the 630 Parent Patent, it is generally emphasized that good quality electronics which employ the Video Integration Read-Out technique have been found to be very conducive to accurately measuring Fourier Coefficients using Photo Array Diode Elements. It is to be understood that said good quality electronics interface output signals from Photo Array Diode Elements to a computer system which collects and analyzes data. Preferred "Off-The-Shelf-Systems" which include good quality electronics, suitable for use in the disclosed invention Rotating Compensator Material System Investigation System, are Zeiss, (Trademaark), Diode Array Spectrometer systems identified by manufacturer numbers selected from the group: MMS1 (300–1150 nm); UV/VIS MMS (190–730 nm); UV MMS (190–400 nm); AND IR MMS (900–2400 nm). Said Zeiss systems also include Dispersive Optics and Diode Element containing Photo Arrays. The Zeiss systems include fourteen (14) bit dynamic range readout electronics, which provides a voltage pulse output. The disclosed invention system provides additional good-quality electronics in the form of an integrator and Analog to Digital Converter. In use, the scanning rate of Diode Elements in a Zeiss system Photo Array is synchronized with the rotation of the Rotating Compensator of the disclosed invention Rotating Compensator Material System Investigation System. Said synchronization is accomplished utilizing standard digital logic, and Diode Elements in the Photo Array are scanned sixteen (16) times under previous practice, and thirteen (13) times under present practice, during each rotation of the Rotating Compensator. It is further noted that the disclosed invention preferably effects rotation of the Rotating Compensator with a hollow shaft Stepper Motor. While it is possible to sense pulses from a sensor attached to a rotating compensator, and use said pulses to synchronize detector output, a preferred approach provides that a sequence of reference pulses is simultaneously provided to the Stepper Motor and to Photo Array Diode Elements. Said reference pulses allow correlation of the angular position of the Rotating Compensator with data provided by the Scanned Photo Array Diode Elements. Further, a phase sensor operates like a traditional encoder, but it is not necessary to trigger off its digital output. Instead the phase sensor output and detector array data are stored and subsequent processing used to determine the phase of the stepper motor, which directly relates to the azimuthal orientation of the rotating compensator.

Regarding Photo Array data, it is further noted that authors, An and Collins, describe some of the non-idealities which can be present when using a Photo Array Detector in a Spectroscopic Rotating Compensator Material System Investigation System. With the exception of the An and Collins correction for "Stray Light" (see An and Collins Eq. 13), however, none of the Photo Array non-ideality corrections which were presented in their paper were found necessary in implementing the preferred embodiment of the disclosed invention. However, to allow a non-ideal Photo Array to be used in the disclosed invention, the relevant corrections for a Image Persistence, and for Read Time in a Spectroscopic Rotating Compensator Material System Investigation System in which sixteen (16) Diode Element Scans are acquired for each Rotating Compensator revolution were derived, and are provided in Eqs. 25–34.

Image Persistence correction, where 'x' is the magnitude of the non-ideality:

$$ip\alpha_2 = \alpha_2 - 0.5 \cdot x \cdot [(2 - \sqrt{2}) \cdot \alpha_2 + \sqrt{2} \cdot \beta_2] \qquad (25)$$

$$ip\beta_2 = \beta_2 - 0.5 \cdot x \cdot [(2 - \sqrt{2}) \cdot \beta_2 - \sqrt{2} \cdot \alpha_2] \qquad (26)$$

$$ip\alpha_4 = \alpha_4 - x \cdot (\alpha_4 + \beta_4) \qquad (27)$$

$$ip\beta_4 = \beta_4 - x \cdot (\beta_4 + \alpha_4) \qquad (28)$$

$$ipDC = DC \qquad (29)$$

Read time correction, where 'ρ' is the channel read time of the diode array:

$$c\alpha_2 = ip\alpha_2\ 0.5 \cdot \rho \cdot [(1 + \sqrt{2}) \cdot ip\alpha_2 + ip\beta_2] \qquad (30)$$

$$c\beta_2 = ip\beta_2 - 0.5 \cdot \rho \cdot [(1 + \sqrt{2}) \cdot ip\beta_2 - ip\alpha_2] \qquad (31)$$

$$c\alpha_4 = ip\alpha_4 - \rho \cdot (ip\alpha_4 + ip\beta_4) \qquad (32)$$

$$c\beta_4 = ip\beta_4 + \rho \cdot (ip\alpha_4 - ip\beta_4) \qquad (33)$$

$$cDC = \left(1 - \frac{4 \cdot \rho}{x}\right) \cdot ipDC \qquad (34)$$

Eqs. 25–34 can be applied after Eqs. 10–17 to account for non-idealities in the Photo Array Diode Element readout. The Image Persistence and Read-Out non-ideality factors 'x' and 'ρ' can also be determined by defining them as Fit Parameters in a Calibration Regression procedure presented in the following section of this Specification.

For demonstration purposes, considering now the disclosed invention Spectroscopic Rotating Compensator Material System Investigation System to be a Rotating Compensator Ellipsometer System with Diode Element Array read-out, it must be understood that to acquire usable data, Calibration must be performed. Said calibration provides numerical values for Azimuthal Orientation Off-set Angles of Polarizer, Analyzer and Compensator with respect to a Material System, (Sample), Frame of Reference, along with the Retardance of the Rotating Compensator as a function of Wavelength. In addition, Calibration Parameters to compensate non-idealities in Diode Elements in a Photo Array are calibrated.

The foundation of the Calibration Procedure was first announced in the 1993 paper by Johs, published in Thin Film Solids, cited in the Background Section herein. The same basic Calibration Procedure technique is further developed in U.S. Pat. No. 5,706,212 which describes calibration of a Rotating Compensator Ellipsometer System utilized in the Infra-red (IR) band of wavelengths. Both identified references, however, describe typical application of the Regression based Calibration technique to one (1) wavelength at a time. While this method does work, it can require two-hundred-fifty-six (256) sets of Calibration Parameters where a two-hundred-fifty-six (256) Diode Element Photo Array is utilized, with each Diode Element serving to monitor an essentially single wavelength. (Note, as the electromagnetic spectrum is continuous, an essentially single wavelength is to be understood to be a small range of wavelengths centered around some wavelength, which essentially single wavelength is intercepted by a Diode Element in a Photo Array).

In practice of the disclosed invention a "Global" regression procedure is typically performed on a Two (2) Dimensional Data Set. Typically Polarizer Azimuthal Angle and Wavelength are selected as Data Set Independent variables, although electromagnetic beam Angle-of-Incidence with respect to a Material system, (Sample), surface could be selected as an Independent variable instead of, for instance, Wavelength or Polarizer Azimuthal Angle. It is also noted that the Regression based Calibration described in U.S. Pat. No. 5,706,212 required that two (2), at least two (2) Dimensional Data Sets be provided in each Regression procedure. The two Data Sets are obtained with different investigated Material System, (Sample), configurations being employed. For instance, Data Sets utilizing two different Material Systems, (Samples), or one Material System, (Sample), present and a "Straight-through" configuration might be utilized. (Note, a "Straight-through" configuration results when no Material System, (Sample), is present, and an electromagnetic beam is caused to pass sequentially through a Polarizer, Compensator and Analyzer then enter a Photo Array Detector System, without interacting with a Material System, (Sample)). The disclosed invention, in its most basic embodiment, requires that only one Data Set be present. Said Data Set can be obtained with the Ellipsometer in Material System, (Sample), present or Straight-through configuration, although some benefits are realized when a Material System, (Sample), is utilized, (discussed supra herein). Of course, the disclosed invention can be practiced utilizing Multiple-Data Sets.

As mentioned, the Regression based Calibration procedure of the disclosed invention requires that an at least Two (2) Dimensional Data Set be experimentally obtained. Typically said Two (2) Dimensional Data Set has as Independent Variables, Polarizer, (where the Rotating Compensator is placed after a Material System, (Sample)), Azimuthal Angle, and Wavelength. Where a Rotating Compensator is placed before a Material System, (Sample), an Analyzer Azimuthal Angle is typically utilized. As mentioned, Angle-of-Incidence of an investigation Electromagnetic Beam with respect to an investigated Material System, (Sample), surface can be substituted for an Analyzer or Polarizer Azimuthal Angle settings, but this is not preferred as Material System, (Sample), PSI and DELTA values vary therewith. Also, it is generally simpler to vary a Polarizer or Analyzer Azimuthal Angle in most Ellipsometer systems in practice. Continuing, data is simultaneously obtained from many Diode Elements, (which correspond to different Wavelengths), and subjected to the Hadamard analysis inherent in Eqs. 20–24, infra, (and see also Eqs. 20'–24' supra herein), to provide Fourier Coefficients present in Eq. 18. (It is noted that a Photo Array can contain 256, 1024 or 2048 Diode Elements, and some thereof might provide a signal which of too small an intensity to be utilized. The disclosed invention allows for utilizing only a user selected group of signals for this and other reasons).

It will be noted that Eqs. 8 and 18 contain a D.C. term "$I_0$". This can be selected as a Fit Parameter in a Regression Procedure or a Normalization procedure can be implemented. Said Normalization can be with respect to the D.C. term, or a Normalizing Parameter can be included. The following Eqs 35a, 35b and 35c provide possible Normalizing Parameters:

$$\text{Norm} = DC \qquad (35a)$$

$$\text{Norm} = \sqrt{(\alpha_2)^2 + (\beta_2)^2 + (\alpha_4)^2 + (\beta_4)^2 + (DC)^2} \qquad (35b)$$

$$\text{Norm} = \sqrt{(\alpha_2)^2 + (\beta_2)^2 + (\alpha_4)^2 + (\beta_4)^2} \qquad (35c)$$

Eq. 35a provides for Normalizing with respect to the D.C. term, Eq. 35b provides for Normalizing to a Parameter which depends on the D.C. Term and the Fourier Coefficients, while Eq. 35c provides for Normalizing to a Parameter which depends on Fourier Coefficients but not the D.C. Term. If Fourier Coefficients are not Normalized, (ie. the D.C. Term "$I_0$" is not included as a Fit Parameter in a Calibration Parameter evaluating Regression Procedure, or Normalization is not performed), it should be appreciated that a "Floating" value result will be obtained for Calibration Parameters provided by application of the Calibration Parameter evaluating Regression onto said Fourier Series Coefficient values. As mentioned infra herein, the D.C. Component "$I_0$" can be difficult to evaluate, often requiring a "Shutter" to block background light, dark current, readout electronics voltage offsets etc. As well, the D.C. component is more susceptible to instrumentation drift. As a result, use of Eq. 35c can be preferrable in the disclosed invention Calibration Procedure to use of Eqs. 35a and 35b and to including "I0" in a Regression Procedure for evaluating Calibration Parameters. (Note that calibration data is taken with the Rotating Compensator Sample System Investigating System in a "Sample Present", rather than a "Straight Through" configuration, where such Eq. 35c normalization is practiced). (Note, Eqs. 67, and accompanying discussion, provide additional insight to Calibration Normalization).

It is further noted that recent practice has adopted use of multiple data sets, similar to that described in U.S. Pat. No. 5,706,212 in disclosed invention procedures to calibrate a Rotating Compensator System, where it is desired to evaluate not only Ellipsometric Parameters, but Depolarization/Mueller Matrix values as well. Said multiple data sets can be obtained with different samples in place and/or with the ellipsometer system in a "straight-through" configuration. It is disclosed that it has been found desirable to normalize data to D.C. in some portions of calibration, and to an A.C. derived term in other portions thereof. An equation, such as presented in EQ. 35c, (which is derived from Fourier Coefficients), is an example of an A.C. data normalization parameter.

To shed light as to why various use of D.C. and A.C. based data normalization Parameters is beneficial, the following parameters are defined:

$N = COS(2*PSI)$;
$C = SIN(2*PSI)COS(DELTA)$; and
$S = SIN(2*PSI)SIN(DELTA)$.

Further:

$C = (fc(ALPHA\ 2, BETA2, ALPHA4, BETA4))/D.C.$;
$S = (fs(ALPHA\ 2, BETA2, ALPHA4, BETA4))/D.C.$;
$N = (fn(ALPHA\ 2, BETA2, ALPHA4, BETA4))/D.C.$;

(where fc, fs and fn are functions to extract N, C and S from ALPHA2, BETA2, ALPHA4, BETA 4 AND D.C.); and $TAN(DELTA) = S/C$, (note the D.C. term cancels);
$TAN(PSI) = ((C^2+S^2)^{(1/2)})/N$, (note the D.C. term cancels);
$\%DEPOL = 100\%(1-N^2-C^2-S^2)$.

Thus it is demonstrated that PSI and DELTA can be calculated without the requirement of a D.C. term, but that calculation of Depolarization require knowledge of the D.C. term.

Preferred calibration procedure practice provides that data be normalized to an A.C. derived basis, (eg. EQ. 35c), when determining such as compensator retardation (R), polarizer azimuth (P) and compensator fast axis azimuth (C), and that data be normalized to D.C., (eg. EQ. 35a or 35b), where optical element Depolarization/Meuller Matrix values are fit. Thus a calibration procedure as recited infra herein can be modified to include a step in which an appropriate normalization basis is determined at various steps therein. (Note, in Eqs. 67, a different approach to defining Depolarization is presented. Nonideality Depolarization terms identified as 'b' and 'c' appear only in a D.C. term.)

Where data normalization by D.C., or A.C, or a combination of D.C. and A.C. normalization data bases is practiced, the method of calibrating the spectroscopic rotating compensator material system investigation system can, in terminology similar to that in the 630 Patent, be recited as comprising, in any functional order, the steps of:

STEP A.

Providing a spectroscopic rotating compensator material system (sample) investigation system comprising a source of a polychromatic beam of electromagnetic radiation, a polarizer means, a stage for supporting a material system (sample), an analyzer means, a dispersive optics and at least one detector system which contains a multiplicity of detector elements, said spectroscopic rotating compensator material system investigation system further comprising at least one compensator(s) means positioned at a location selected from the group consisting of: (before said stage for supporting a material system, and after said stage for supporting a material system, and both before and after said stage for supporting a material system (sample)); such that when said spectroscopic rotating compensator material system investigation system is used to investigate a material system (sample) present on said stage for supporting a material system, said analyzer means and polarizer means are maintained essentially fixed in position and at least one of said at least one compensator(s) means is/are caused to continuously rotate while a polychromatic beam of electromagnetic radiation produced by said source of a polychromatic beam of electromagnetic radiation is caused to pass through said polarizer means and said compensator(s) means, said polychromatic beam of electromagnetic radiation being also caused to interact with said material system (sample), pass through said analyzer means and interact with said dispersive optics such that a multiplicity of essentially single wavelengths are caused to simultaneously enter a corresponding multiplicity of detector elements in said at least one detector system;

at least one of said at least one compensator(s) means preferably being a selection from the group consisting of:

comprised of a combination of at least two zero-order waveplates, said zero-order waveplates having their respective fast axes rotated to a position offset from zero or ninety degrees with respect to one another;

comprised of a combination of at least a first and a second effective zero-order wave plate, said first effective zero-order wave plate being comprised of two multiple order waveplates which are combined with the fast axes thereof oriented at a nominal ninety degrees to one another, and said second effective zero-order wave plate being comprised of two multiple order waveplates which are combined with the fast axes thereof oriented at a nominal ninety degrees to one another; the fast axes of the multiple order waveplates in said second effective zero-order wave plate being rotated to a position at a nominal forty-five degrees to the fast axes, respectively, of the multiple order waveplates in said first effective zero-order waveplate; comprised of a combination of at least a first and a second effective zero-order wave plate, said first effective zero-order wave plate being comprised of two multiple order waveplates which are combined with the fast axes thereof oriented at a nominal ninety degrees to one another, and said second effective zero-order wave plate being comprised of two multiple order waveplates which are combined with the fast axes thereof oriented at a nominal ninety degrees to one another; the fast axes of the multiple order waveplates in said second effective zero-order wave plate being rotated to a position away from zero or ninety degrees with respect to the fast axes, respectively, of the multiple order waveplates in said first effective zero-order waveplate;

comprised a combination of at least one zero-order waveplate and at least one effective zero-order waveplate, said effective zero-order wave plate being comprised of two multiple order waveplates which are combined with the fast axes thereof oriented at a nominal ninety degrees to one another, the fast axes of the multiple order waveplates in said effective zero-order wave plate being rotated to a position away from zero or ninety degrees with respect to the fast axis of the zero-order waveplate;

STEP B.

developing a mathematical model which comprises as calibration parameter variables such as polarizer means azimuthal angle orientation, present material system (sample) PSI, present material system (sample) DELTA, compensator means azimuthal angle orientation(s), matrix components of said compensator(s) means, and analyzer means azimuthal angle orientation, which mathematical model is effectively a transfer function which enables calculation of electromagnetic beam magnitude as a function of wavelength detected by a detector element, given magnitude as a function of wavelength provided by said source of a polychromatic beam of electromagnetic radiation;

STEP C.

causing a polychromatic beam of electromagnetic radiation produced by said broadband electromagnetic radiation source means of a polychromatic beam of electromagnetic radiation, to pass through said polarizer means, interact with a material system (sample) caused to be in the path thereof, pass through said analyzer means, and interact with said dispersive optics such that a multiplicity of essentially single wavelengths are caused to simultaneously enter a corresponding multiplicity of detector elements in said at least one detector system, with said polychromatic beam of electromagnetic radiation also being caused to pass through said compensator(s) means positioned at a location selected from the group consisting of: (before said stage for supporting a material system, and after said stage for supporting a material system, and both before and after said stage for supporting a material system);

STEP D.

obtaining at least one, multi-dimensional, data set of magnitude values vs. wavelength and at least one parameter selected from the group consisting of:

angle-of-incidence of said polychromatic beam of electromagnetic radiation with respect to a present material system; and azimuthal angle rotation of one element selected from the group consisting of:
said polarizer means;
said analyzer means;

OR obtaining at least one multi-dimensional data set or at least two, at least one-dimensional, data sets of magnitude values vs. parameterts) selected from the group consisting of:

wavelength;

angle-of-incidence of said polychromatic beam of electromagnetic radiation with respect to a present material system; and azimuthal angle rotation of one element selected from the group consisting of:
said polarizer means; and
said analyzer means;

over time, while at least one of said at least one compensator (s) is caused to continuously rotate;

(It is noted here that a Reference Material System, (Sample), Thickness, or the Thickness of a Surface Layer thereupon, as well as DELTA Offset resulting from electromagnetic beam passage through birefringent window(s) and/or lens(es), or wavelength shifts can be utilized as additional parameterization independent variables)

said data set(s) being obtained utilizing a selection from the group consiting of:

all of said data set(s), being obtained with a single material system placed on said stage for supporting a material system, with which material system said beam of electromagnetic radiation is caused to interact;

at least one of said data set(s), being obtained utilizing one material system placed on said stage for supporting a material system, with another of said data set(s), being obtained utilizing another material system (sample) placed on said stage for supporting a material system (sample), with which material system (sample) said beam of electromagnetic radiation is caused to interact; and at least one of said data set(s) being obtained with the spectroscopic rotating compensator material system (sample) investigation system oriented in a "straight-through" configuration wherein a polychromatic beam of electromagnetic radiation produced by said source of a polychromatic beam of electromagnetic radiation, is caused to pass through said polarizer means, pass through said analyzer means and interact with said dispersive optics such that a multiplicity of essentially single wavelengths are caused to simultaneously enter a corresponding multiplicity of detector elements in said at least one detector system, with said polychromatic beam of electromagnetic radiation also being caused to pass through at least one compensator(s) means but without being caused to interact with any material system (sample) placed on said stage for supporting a material system (sample) other than open ambient atmosphere;

STEP S.

normalizing data in said data set(s) with respect to a selection from the group consisting of:

a data set D.C. component;

a data set A.C. component;

a parameter derived from a combinations of a data set D.C. component and a data set A.C. component;

STEP F.

performing a mathematical regression of said mathematical model onto said normalized data set(s) thereby evaluating calibration parameters in said mathematical model;

said regression based calibration procedure serving to evaluate parameters in said said mathematical model for non-achromatic characteristics and/or non-idealities and/or positions of at least one selection from the group consisting of:

azimuthal angle of said polarizer means;

retardation of said compensator(s) means ;

azimuthal angle(s) of said compensator(s) means, and depolarization/Mueller Matrix components.

azimuthal angle of said analyzer means.

STEP G.

optionally repeating STEPS E. and F. utilizing a different selection in STEP E. in normalizing data.

(Note that optionally un-normalized D.C. and/or A.C. data can be utilized to determine Reflectance and said information utilized in determining parameter values in the Step F. Regression. Further, once Calibration is completed, parameter values other than Sample characterizing parameters can be fixed, and additional Samples investigated with only Sample Characterizing Parameters being left for evaluation).

Continuing, normalized Fourier Coefficients can be represented by Eqs 36–39:

$$n\alpha_2 = \frac{\alpha_2}{Norm} \qquad (36)$$

$$n\beta_2 = \frac{\beta_2}{Norm} \qquad (37)$$

-continued $$n\alpha_4 = \frac{\alpha_4}{Norm} \quad (38)$$

$$n\beta_4 = \frac{\beta_4}{Norm} \quad (39)$$

A Global Calibration Data Set can be represented by Eq. 40:

$$MFD_{P,n} = \{(n\alpha_2)_{P,n}, (n\beta_2)_{P,n}, (n\alpha_4)_{P,n}, (n\beta_4)_{P,n}\} \quad (40)$$

where MFD stands for Measured Fourier Data, and where "P" is the Polarizer Angle and constitutes one independent Variable, (and is typically varied within the range of from zero (0.0) to one-hundred-eighty (180) degrees, in ten (10) degree steps), and where "n" identifies the index of a selected Diode element, (channel), in the Photo Array, or alternatively stated, identifies a Second Independent Variable, (ie. wavelength). It is noted that a typical system configuration would make use of Diode Elements (channels) 30–250 in a 256 channel Photo Array. The term "Global" emphasizes the presence of Wavelength Dependence. Utilizing the rust described "P" range settings and Wavelength range, Eq. 41 indicates that the Global MFD Data Set would contain:

(180/10+1 polarizer settings)×(250−30+1 channels)×(4 Fourier components)=16,796 values (41)

It is further noted that an approximate error in Fourier Data can be estimated from signal to noise at each Detector Channel, and subsequently used in the Regression Analysis of the Experimentally Obtained Data get.

Continuing, use of Eqs. 3–17, 35–39 and (25–34 if Photo Array non-idealities are included), allows one to calculate, (ie. mathematically predict), values of Normalized Fourier Coefficients as in Eqs. 36–39, which will be experimentally measured by a Rotating Compensator Material System Investigation System. However, to make said mathematical prediction requires that Material System, (Sample), PSI and DELTA values be known, the Offset Angles $P_s$, ($A_s$, and $C_s$ be known, and that Compensator Retardation "δ" be known as well as any other Compensator non-idealities, and that the Photo Array non-idealities "x" and "ρ" be known if necessary. Mathematically this can be represented by Eq. 42:

$$PFD_{P,n}(P, \Psi_n, \Delta_n, (P_s)_n, (C_s)_n, (A_s)_n, \delta_n, x_n, \rho_n) \quad (42)$$

Eq. 42 states that a Predicted Fourier Data (PFD) Set at a given Polarizer Azimuth and Photo Array Channel (Wavelength), is a function of identified variables, which variables constitute Calibration Parameters which must be provided numerical values. The Regression procedure provides means for numerically evaluating the Calibration Parameters.

In all known prior art, separate Regression procedures have been carried out at each utilized Wavelength. If Two-Hundred (200) Wavelengths were utilized, then Two-Hundred (200) separate values for $P_s$, $A_s$ and $C_s$ etc. would be obtained. The Regression Procedure, however, teaches that Calibration Parameters as a function of an Independent Variable, (eg. Wavelength), can be "Parameterized". That is, a mathematical relationship requiring only a few (eg. perhaps two (2) or three (3) Parameters), can be generated to describe a functional relationship between the Calibration Parameter and the Independent Variable (eg. Wavelength), and the Regression Procedure utilized to evaluate said Two (2) or Three (3) Parameters. For example, the Polarizer Azimuthal Offset ($P_s$) might be constant for all Wavelengths. Should this be the case then said Polarizer Azimuthal Offset ($P_s$) can be evaluated and stored, rather than, for instance, Two-Hundred (200) separate values at Two-Hundred (200) separate Wavelengths. In this instance, Eq. 43 indicates that a Global Calibration Parameter can be defined:

$$(P_s)_n = gP_s \quad (43)$$

In general, any of the discretely defined Calibration Parameters identified in Eq. 42, could be replaced by a Global Parametric Function as defined in Eq. 44:

$$CP_n = gCP(n, p_1, p_2, \ldots, p_k) \quad (44)$$

where $CP_n$ stands for any Calibration Parameter which is discretely defined for each "n"'th channel, (ie. the "n"'th Wavelength), and "gCP" is a global Parametric Function (as a function of an "n"'th channel number and "k" Calibration Parameters "p1 . . . pk") which replace $CP_n$. A Parametric Function can be of any mathematical form, such as, but not limited to, polynomial, rational or trancendental (in the case of $\Psi_n$ and $\Delta_n$, a Parametric Function could be calculated from a multi-layer optical model for a Material System, (Sample), using known Material Optical Constants and Parameterized Film Thicknesses). The important characteristic of a Parametric Function being that;

1. It accurately represents the behavior of the Calibration Parameter at each Independent Variable (eg. Photo Array Channel or wavelength).

2. It accurately represents the behavior of the Calibration Parameter utilizing fewer Parameters than would be required to simply evaluate Calibration Parameters at each utilized Independent Variable (eg. Wavelength).

In terms of Eq. 44 this can be stated that "k" (the number of Calibration Parameters), is less than "n" (the number of channels).

It is to be understood that preferred Global Parameter Function form utilized depends upon the particular embodiment utilized, (eg. the Compensator type utilized). It is also within the scope of the Regression based Calibration Parameter evaluation Procedure to represent some Calibration Parameters with Global Parametric Functions, and to represent other Calibration Parameters discretely. Three examples of Global Parametric Function utilizing Models follow directly.

Global Regression Mode (GRM) 1

This (GRM) requires that five (5) Calibration Parameters be evaluated. Eqs. 45–47 provide equations for Predicted Fourier Data (PFD):

$$PFD_{P,n}(P, \Psi_n, \Delta_n, gP_s, gC_s, gA_s, g\delta(n, p_0, p_1)) \quad (45)$$

where $$g\delta(n, p_0, p_1) = [p_0 \cdot 90 \cdot (1 + p_1/[w(n)]^2)]/w(n) \quad (46)$$

and $$w(n) = C_0 + C_1 \cdot n + C_2 \cdot n^2 \quad (47)$$

where W(n) returns a wavelength of electromagnetic radiation (in nanometers), corresponding to the "n"'th channel of a Photo Array, where $C_0$, $C_1$ and $C_2$ are wavelength Calibration Parameters. In the case where a previously identified Ziess Diode Array Spectrometer Systems is utilized, said $C_0$, $C_1$ and $C_2$ Calibration Parameters are provided by the manufacturer, and Eq. 47 can be utilized to provide Wavelength given a Photo Array Channel number. The Global Retardance provided by a Compensator as a function of Wavelength is given by Eq. 46. Eq. 46 provides an Inverse Wavelength relationship, where "$p_0$" is a Wavelength, (in nanometers), at which said Compensator is a "Quarter-Wave-Plate" and demonstrates a Ninety (90) degree Retardation, and "$p_1$" accounts for the Dispersive effects in the Optical Properties of the Compensator. Higher order terms can be added to Eq. 46.

In this (GRM) Mode 1, the Azimuthal Offset Calibration Parameters are considered constant for all Wavelengths. Therefore, using (GRM) Mode 1, only Five (5) Global Calibration Parameters:

$$(gP_s, gC_s, gA_s, p_0, p_1)$$

in addition to Material System, (Sample), PSI and DELTA:

$$\Psi_n \text{ and } \Delta_n$$

need to be evaluated by a Regression Procedure.

Global Regression Mode (GRM) 2

This Mode is similar to (GRM) 1, but the $P_s$ Calibration Parameter is defined as a Global Calibration Parameter, (ie. it is a constant independent of Photo Array Channel Number "n"). Again, the Retardance of the Compensator is Parameterized by Eqs. 46 and 47. Values for $C_s$ and $A_s$ are allowed to take on discrete vales at each Photo Array Channel, however, Eq. 48 indicates the relationship:

$$PFD_{P,n}(P, \Psi_n, \Delta_n, gP_s, (C_s)_n, (A_s)_n, g\delta(n, p_0, p_1)) \quad (48)$$

Global Regression Mode (GRM) 3

In this (GRM) 3 Mode, only $P_s$ is defined as a Global Parameter, and all other system Calibration Parameters are allowed to take on discrete values at each Photo Array Channel. Eq. 49 indicates this relationship:

$$PFD_{P,n}(P, \Psi_n, \Delta_n, gP_s, (C_s)_n, (A_s)_n, \delta_n) \quad (49)$$

(SEE ALSO GLOBAL REGRESSION MODE (GRM) 4) SUPRA HEREIN.

Regression

The Methodology of U.S. Pat. No. 5,872,630 evaluates the Calibration Parameters identified infra herein utilizing standard non-linear regression analysis. First a metric is defined by Eq. 50 to quantify Error between Calculated Predicted Fourier Data (PFD) and Experimentally Measured Fourier Data (MFD).

$$z^2 = \sum_P \sum_n \left( \frac{MFD_{P,n} - PFD(P, n, p_k)}{\sigma MFD_{P,n}} \right)^2 \quad (50)$$

Eq. 50 is a simplified way of stating that overall error between measured and predicted Calibration Data Sets is given by the squared difference between each measured and corresponding calculated predicted Fourier data, normalized by the approximate error at each measured data point ($\sigma MFD_{P,n}$), and summed over all the Polarizer and Wavelength (Channel) setting values. Eq. 51 provides a more riggerous mathematical definition.

$$z^2 = \sum_P \sum_n \left[ \begin{array}{l} \left[ \frac{(m\alpha_2)_{P,n} - p\alpha_{2(P,n,p_k)}}{(\sigma\alpha_2)_{P,n}} \right]^2 + \\ \left[ \frac{(m\beta_2)_{P,n} - p\beta_{2(P,n,p_k)}}{(\sigma\beta_2)_{P,n}} \right]^2 \cdots + \\ \left[ \frac{(m\alpha_4)_{P,n} - p\alpha_{4(P,n,p_k)}}{(\sigma\alpha_4)_{P,n}} \right]^2 + \\ \left[ \frac{(m\beta_4)_{P,n} - p\beta_{4(P,n,p_k)}}{(\sigma\beta_4)_{P,n}} \right]^2 \end{array} \right] \quad (51)$$

In Eqs. 50 and 51, $p_k$ represents the "k" adjustable system Calibration Parameters required to calculate (PFD). The well known Marquardt-Levenberg non-linear Algorithm, as described in the Johs paper cited in the Background Section herein, can be used to iteratively adjust system Calibration Parameters $p_k$ to minimize error.

It is noted that good initial values are required to practice Regression which converges rapidly. The disclosed invention practice obtains good starting values for use in the Global Regressions described, by performing a number of non-global Regressions at a multiplicity of discrete Wavelengths. The resulting ranges of values for the various Calibration Parameters then allows educated selection for Global Regression starting values.

It is also noted that Global Regression can be performed utilizing only data from every "N"'th Channel, (eg. every "N"'th Wavelength), to reduce required Regression procedure time to arrive at convergence. This approach to Regression is still to be considered as Global.

Once the Spectroscopic Rotating Compensator Material System Investigation System is calibrated, it is possible to take data from unknown samples therewith and obtain PSI and DELTA plots therefore. Kleim et al., describes equations for PSI ($\Psi$) and DELTA ($\Delta$) and these equations are provided as Eq. 52 and 53 herein:

$$\tan(2 \cdot \Psi) = \frac{\sqrt{|(\alpha_2)^2 + (\beta_2)^2| \cdot \left(\frac{1 - \cos(\delta)}{\sin(\delta)}\right)^2 + 4 \cdot (\beta_4 \cdot \cos(2 \cdot P) - \alpha_4 \cdot \sin(2 \cdot P))^2}}{2 \cdot (\alpha_4 \cdot \cos(2 \cdot P) + \beta_4 \cdot \sin(2 \cdot P))} \quad (52)$$

$$\tan(\Delta) = \left( \frac{1 - \cos(\delta)}{2 \cdot \sin(\delta)} \right) \cdot \frac{\alpha_2 \cdot \sin(2 \cdot P) - \beta_2 \cdot \cos(2 \cdot P)}{\alpha_4 \cdot \sin(2 \cdot P) - \beta_4 \cdot \cos(2 \cdot P)} \quad (53)$$

In these equations the Analyzer should be set to +/−45 degrees. Also, prior to applying Eqs. 52 and 53 the measured Fourier Data should be transformed into "ideal" Fourier Data by application of Eqs. 15a, 15b, 16a, 16b, 17a and 17b as well as Eqs. 25–34. Kleim et al. also describes the advantages of performing a zone-averaged measurement in a Rotating Compensator System, (ie. averaging the PSI and DELTA extracted from measurements with the Analyzer A set to first, +45 Degrees, and second to −45 Degrees. This can be concurrently practiced with the described methodology to further improve the accuracy of data measurement.

It is also noted that an alternative approach to obtaining Material System, (Sample), PSI and DELTA characterizing data, is to perform a Calibration Procedure on a Spectroscopic Rotating Compensator Material System Investigation System in a Sample Present Mode, with said Material System, (Sample), present therein.

New Derivation of Frequency Components in General Rotating Compensator Ellipsometer/Polarimeters System as First Presented in Co-Pending application Ser. No. 09/496,011.

Since the just reviewed teachings from Parent U.S. Pat. No. 5,872,630 were originally presented, additional work in the area has resulted in derivation of more generalized Equations which account for various frequency components which present in a Rotating Compensator ellipsometer or polarimeter system. Said derivation is based in application of general Mueller Matrix representations for optical elements. Eq. 54 provides said general Meuller Matrix representation:

$$M = \begin{bmatrix} m11 & m12 & m13 & m14 \\ m21 & m22 & m23 & m24 \\ m31 & m32 & m33 & m34 \\ m41 & m42 & m43 & m44 \end{bmatrix} \quad 54$$

Additionally, Eq. 55 demonstrates application of Rotation Matrices which serve to account for differences in angular orientation, ('$\phi$') between a beam path coordinate system and an optical element coordinate system:

$$Mrot = \begin{bmatrix} 1 & 0 & 0 & 0 \\ 0 & \cos(2\phi) & -\sin(2\phi) & 0 \\ 0 & \sin(2\phi) & \cos(2\phi) & 0 \\ 0 & 0 & 0 & 1 \end{bmatrix} \begin{bmatrix} m11 & m12 & m13 & m14 \\ m21 & m22 & m23 & m24 \\ m31 & m32 & m33 & m34 \\ m41 & m42 & m43 & m44 \end{bmatrix} \begin{bmatrix} 1 & 0 & 0 & 0 \\ 0 & \cos(2\phi) & \sin(2\phi) & 0 \\ 0 & -\sin(2\phi) & \cos(2\phi) & 0 \\ 0 & 0 & 0 & 1 \end{bmatrix} \quad 55$$

Multiplying Eq. 55 through provivdes:

$$\begin{bmatrix} m11 & m12 \cdot c2\phi - m13 s2\phi & m12 s2\phi + m13 c2\phi & m14 \\ c2\phi \cdot m21 - s2\phi \cdot m31 & c2\phi^2 \cdot m22 + s2\phi^2 \cdot m33 - s2\phi c2\phi \cdot (m23 + m32) & c2\phi^2 \cdot m23 + s2\phi^2 \cdot m32 + s2\phi c2\phi(m22 - m33) & c2\phi m24 - s2\phi m34 \\ c2\phi \cdot m21 + s2\phi \cdot m31 & c2\phi^2 \cdot m32 - s2\phi^2 \cdot m23 + s2\phi c2\phi \cdot (m22 - m33) & c2\phi^2 \cdot m33 + s2\phi^2 \cdot m22 + s2\phi \cdot c2\phi(m23 + m32) & s2\phi \cdot m24 + c2\phi m34 \\ m41 & m42 \cdot c2\phi - m43 \cdot s2\phi & m42 \cdot s2\phi + m43 \cdot c2\phi & m44 \end{bmatrix} \quad 56$$

where $c2\phi = \cos(2\phi)$ and $s2\phi = \sin(2\phi)$.

Now, if a general optical element is continuously rotated, the Matrix in Eq. 56 can be broken into a sum of matrices which describe each frequency component, (ie. via Fourier Coefficients), and Eq. 57 demonstrates this:

$$Mrot = DC + A2 \cdot \cos(2\phi) + B2 \cdot \sin(2\phi) + A4 \cdot \cos(4\phi) + B4 \cdot \sin(4\phi) \quad 57$$

where:

$$DC = \begin{bmatrix} m11 & 0 & 0 & m14 \\ 0 & \frac{m22+m33}{2} & \frac{m23-m32}{2} & 0 \\ 0 & \frac{m32-m23}{2} & \frac{m22+m33}{2} & 0 \\ m41 & 0 & 0 & m44 \end{bmatrix} \quad 58$$

$$A2 = \begin{bmatrix} 0 & m12 & m13 & 0 \\ m21 & 0 & 0 & m24 \\ m31 & 0 & 0 & m34 \\ 0 & m42 & m43 & 0 \end{bmatrix}$$

$$B2 = \begin{bmatrix} 0 & m13 & m12 & 0 \\ m31 & 0 & 0 & -m34 \\ m21 & 0 & 0 & m24 \\ 0 & -m43 & m42 & 0 \end{bmatrix}$$

$$A4 = \begin{bmatrix} 0 & 0 & 0 & 0 \\ 0 & \frac{m22-m33}{2} & \frac{m32+m23}{2} & 0 \\ 0 & \frac{m32+m23}{2} & \frac{m33-m22}{2} & 0 \\ 0 & 0 & 0 & 0 \end{bmatrix}$$

$$B4 = \begin{bmatrix} 0 & 0 & 0 & 0 \\ 0 & \frac{-m32-m23}{2} & \frac{m22-m33}{2} & 0 \\ 0 & \frac{m22-m33}{2} & \frac{m32+m23}{2} & 0 \\ 0 & 0 & 0 & 0 \end{bmatrix}$$

The frequency content for an arbitrary rotating optical element placed into an optical system can thus be easily calculated by inserting the appropriate frequency content matrix into the product of the Mueller Matracies which mathematically represent the optical system. And it is noted that while rotating a general optical element produces only D.C. and even harmonics, (ie. 2nd and 4th harmonics relative to the rotation frequency), if the Mueller Matrix elements are not constant as a function of rotation angle, additional "odd", and higher order harmonics could also be generated.

Proceeding, assuming that an ellipsometer system consists of an input polarizer with azimuthal angle P, a general rotating element, an analyzer with an azimuthal angle A, and a detector, an equation for Intensity output from a General Rotating Element Ellipsometer System can be derived as follows:

$$I = (1\ 0\ 0\ 0) \cdot \begin{bmatrix} 1 & 0 & 0 & 0 \\ 0 & \cos(2A) & -\sin(2A) & 0 \\ 0 & \sin(2A) & \cos(2A) & 0 \\ 0 & 0 & 0 & 1 \end{bmatrix} \begin{bmatrix} 1 & 1 & 0 & 0 \\ 1 & 1 & 0 & 0 \\ 0 & 0 & 0 & 0 \\ 0 & 0 & 0 & 0 \end{bmatrix} \begin{bmatrix} 1 & 0 & 0 & 0 \\ 0 & \cos(2A) & \sin(2A) & 0 \\ 0 & -\sin(2A) & \cos(2A) & 0 \\ 0 & 0 & 0 & 1 \end{bmatrix} \begin{bmatrix} 1 & -N & 0 & 0 \\ -N & 1 & 0 & 0 \\ 0 & 0 & 0 & 0 \\ 0 & 0 & -S & C \end{bmatrix} \cdot$$

$$Mrot \cdot \begin{bmatrix} 1 \\ \cos(2P) \\ \sin(2P) \\ 0 \end{bmatrix}$$

and simplifying yields:

$$I = (1 - \cos(2 \cdot A) \cdot N - N + \cos(2 \cdot A)\sin(2 \cdot A) \cdot C\sin(2 \cdot A) \cdot S) \cdot \quad 60$$

$$Mrot \begin{bmatrix} 1 \\ \cos(2P) \\ \sin(2P) \\ 0 \end{bmatrix}$$

where an isotropic matrix was used to represent the material system sample.

To calculate the frequency content of the measured Intensity, the general rotating frequency component matracies are sequentially substituted for Mrot in the Eq. 60. to yield:

$$DC = (1 - \cos(2 \cdot A) \cdot N - N + \cos(2 \cdot A)\sin(2 \cdot A) \cdot C\sin(2 \cdot A) \cdot \quad 58$$

$$S) \cdot \begin{bmatrix} m11 & 0 & 0 & m14 \\ 0 & \frac{m22+m33}{2} & \frac{m23-m32}{2} & 0 \\ 0 & \frac{m32-m23}{2} & \frac{m22+m33}{2} & 0 \\ m41 & 0 & 0 & m44 \end{bmatrix} \begin{bmatrix} 1 \\ \cos(2P) \\ \sin(2P) \\ 0 \end{bmatrix}$$

$$A2 = (1 - \cos(2 \cdot A) \cdot N - N + \cos(2 \cdot A)\sin(2 \cdot A) \cdot C\sin(2 \cdot A) \cdot$$

$$S) \cdot \begin{bmatrix} 0 & m12 & m13 & 0 \\ m21 & 0 & 0 & m24 \\ m31 & 0 & 0 & m34 \\ 0 & m42 & m43 & 0 \end{bmatrix} \begin{bmatrix} 1 \\ \cos(2P) \\ \sin(2P) \\ 0 \end{bmatrix}$$

$$B2 = (1 - \cos(2 \cdot A) \cdot N - N + \cos(2 \cdot A)\sin(2 \cdot A) \cdot C\sin(2 \cdot A) \cdot$$

$$S) \cdot \begin{bmatrix} 0 & m13 & m12 & 0 \\ m31 & 0 & 0 & -m34 \\ m21 & 0 & 0 & m24 \\ 0 & -m43 & m42 & 0 \end{bmatrix} \begin{bmatrix} 1 \\ \cos(2P) \\ \sin(2P) \\ 0 \end{bmatrix}$$

$$A4 = (1 - \cos(2 \cdot A) \cdot N - N + \cos(2 \cdot A)\sin(2 \cdot A) \cdot C\sin(2 \cdot A) \cdot$$

$$S) \cdot \begin{bmatrix} 0 & 0 & 0 & 0 \\ 0 & \frac{m22-m33}{2} & \frac{m32+m23}{2} & 0 \\ 0 & \frac{m32+m23}{2} & \frac{m33-m22}{2} & 0 \\ 0 & 0 & 0 & 0 \end{bmatrix} \begin{bmatrix} 1 \\ \cos(2P) \\ \sin(2P) \\ 0 \end{bmatrix}$$

-continued $$B4 = (1 - \cos(2 \cdot A) \cdot N - N + \cos(2 \cdot A)\sin(2 \cdot A) \cdot C\sin(2 \cdot A) \cdot$$

$$S) \cdot \begin{bmatrix} 0 & 0 & 0 & 0 \\ 0 & \frac{-m32-m23}{2} & \frac{m22-m33}{2} & 0 \\ 0 & \frac{m22-m33}{2} & \frac{m32+m23}{2} & 0 \\ 0 & 0 & 0 & 0 \end{bmatrix} \begin{bmatrix} 1 \\ \cos(2P) \\ \sin(2P) \\ 0 \end{bmatrix}$$

where $N = \cos(2\Psi)$, $C = \sin(2\Psi)\cos(\Delta)$, $S = \sin(2\Psi)\sin(\Delta)$.

$C2A = \cos(2A)$, $S2A = \sin(2A)$, $C2P = \cos(2P)$, $S2P = \sin(2P)$:

Final Fourier Coefficients for a general rotating element ellipsometer system, where "φ" is the rotating azimuth of the rotating element:

Beam_Intensity=$DC+A2\cdot\cos(2\phi)+B2\cdot\sin(2\phi)+A4\cdot\cos(4\phi)+B4\cdot\sin(4\phi)$ $DC=(-m11 C2A-C2P(m22+m33)$ $+S2P\cdot(m32-m23))$ $\cdot N/2+(C2P\ S2A(m32-m23)$ $+S2P\ S2A(m22+m33))C/2\ \ldots$ $+S2A\cdot S\cdot m41+m11+1/2$ $\cdot C2P\cdot C2A(m22+m33)$ $+1/2\cdot S2P$ $\cdot C2A\cdot(m23-m32)$ $A2=(-m21-C2A$ $\cdot(m12\cdot C2P+S2P$ $\cdot m13))\cdot N+(S2A$ $\cdot(m42\cdot C2P+S2P\cdot m43))$ $\cdot S+m21\ C2A+S2A\cdot C\cdot m31+C2P\cdot$ $m12+S2P\ m$ $B2=(m31+C2A$ $\cdot(C2P\cdot m13-S2P\cdot m12))$ $\cdot N+(-S2A$ $(C2P\cdot m43-m42\ S2P))\cdot S-m31\ C2A+S2A$ $\cdot C\cdot m21-C2P$ $m13+S2P\cdot m$ $A4 = (C2P$ $\cdot (m33-m22) - S2P(m32+m23))$ $\cdot N/2 + (C2P$ $\cdot S2A \cdot (m32+m23) + S2P$ $\cdot S2A(m33-m22))C/2 \ldots$ $+1/2 \cdot S2P \cdot C2A \cdot (m32+m23) + 1/2 \cdot C2P$ $\cdot C2A \cdot (m22-m33)$ $B4 = (C2P \cdot (m32+m23) + S2P$ $\cdot (m33-m22)) \cdot N/2 + (C2P$ $\cdot S2A \cdot (m22-m33) + S2P$ $\cdot S2A(m32+m23)) \cdot C/2 -$ $+1/2 \cdot S2P \cdot C2A \cdot (m22-m33) - 1/2 \cdot C2P$ $\cdot C2A \cdot (m32+m23)$ If the general rotating element is an ideal compensator represented by the Mueller Matrix In Eq. 63, the Fourier Coefficients simplify to the expressions in Eq. 64.

$$M\_ideal\_compensator = \begin{bmatrix} 1 & 0 & 0 & 0 \\ 0 & 1 & 0 & 0 \\ 0 & 0 & \cos\delta & \sin\delta \\ 0 & 0 & -\sin\delta & \cos\delta \end{bmatrix} \quad 63$$

$DC = $  64

$(S2PS2A \cdot C + C2P \cdot (C2A - N)) \cdot \frac{(1+\cos\delta)}{2} + 1 - \frac{1}{2}NC2A$ $A2 = S2AS2P\sin\delta \cdot S$ $B2 = S2AC2P\sin\delta S$ $A4 = \frac{(1-\cos\delta)}{2}(C2P \cdot (C2A - N) - S2AS2P \cdot C)$ $B4 = \frac{(1-\cos\delta)}{2}(S2P \cdot (C2A - N) + S2AC2PC)$ In actual rotating compensator systems, finite bandwidth and imperfect collimination can induce an apparent depolarization into the Mueller Matrix of the compensator of the form shown in Eq. 65:

$$M\_actual\_compensator = \begin{bmatrix} 1 & 0 & 0 & 0 \\ 0 & 1-c & 0 & 0 \\ 0 & 0 & \cos\delta \cdot (1-b) & \sin\delta \cdot (1-b) \\ 0 & 0 & -\sin\delta \cdot (1-b) & \cos\delta \cdot (1-b) \end{bmatrix} \quad 65$$

and the Fourier Coeficients become:

$DC = (S2P \cdot S2A \cdot C + C2P \cdot (C2A - N)) \cdot$  66

$\frac{(1 + \cos\delta \cdot (1-b) - c)}{2} + 1 - \frac{1}{2} \cdot N \cdot C2A$ $A2 = S2A \cdot S2P \cdot \sin\delta \cdot S \cdot (1-b)$ $B2 = S2A \cdot C2P \cdot \sin\delta \cdot S \cdot (1-b)$ $A4 = \frac{(1-\cos\delta \cdot (1-b) - c)}{2} \cdot (C2P \cdot (C2A - N) - S2A \cdot S2P \cdot C)$ $B4 = \frac{(1-\cos\delta \cdot (1-b) - c)}{2} \cdot (S2P \cdot (C2A - N) + S2AC2P \cdot C)$ If A.C. Normalization is used there is no sensitivity to these non-idealities, and the equations can be simply transformed as shown in Eqs. 67 to fit for an effective Compensator Retardance "δ', and the effective non-idealities 'b' and 'c' will appear only in the D.C. term:

$DC = [(S2P \cdot S2A \cdot C + C2P \cdot (C2A - N)) \cdot$  67

$\frac{(1 + \cos\delta - c)}{2} + 1 - \frac{1}{2} \cdot N \cdot C2A](1+b)$ $A2 = S2A \cdot S2P \cdot \sin\delta \cdot S$ $B2 = S2A \cdot C2P \cdot \sin\delta \cdot S$ $A4 = \frac{(1-\cos\delta)}{2} \cdot (C2P \cdot (C2A - N) - S2A \cdot S2P \cdot C)$ $B4 = \frac{(1-\cos\delta)}{2} \cdot (S2P \cdot (C2A - N) + S2AC2P \cdot C)$ Inversion of Fourier Coefficients to Extract Ellipsometric Coefficients N, C and S The preceeding Equations can be inverted to extract N, C and S, given the Fourier Coefficients that are measured by an ellipsometer system:

$((rDC \cdot C2PC2A + 1)a4 + C2A \cdot$  68

$N = \frac{b4 \cdot S2P \cdot rDC - C2A \cdot cR)}{((rDC \cdot C2P + C2A) \cdot a4 +}$ $b4 \cdot rDCS2P - cR)$ $C = \left(\frac{C2A^2 - 1}{S2A}\right) \cdot \frac{b4}{((rDcC2P + C2A)a4 +}$, $b4rDC \cdot S2P - cR)$ $S = \left(\frac{C2A^2 - 1}{S2A}\right) \cdot \frac{cR}{sR} \cdot \frac{a2}{((rDC \cdot C2P + C2A) \cdot a4 +}$ $b4 \cdot rDC \cdot S2P - cR)$ where $a2 = \frac{-A2 \cdot S2P + B2 \cdot C2P}{DC} \cdot (1+b)$ $a4 = \frac{A4 \cdot C2P + B4 \cdot S2P}{DC} \cdot (1+b)$ $b4 = \frac{-A4 \cdot S2P + B4 \cdot C2P}{DC} \cdot (1+b)$ $rDC = \frac{(1 + \cos\delta - c)}{2}$ $cR = \frac{1 - \cos\delta}{2}$ $sR = \sin\delta$ The traditional Ellipsometric Parameters are given by:

$\Delta = \operatorname{atan}\left(\frac{S}{C}\right)$  69

$\Psi = \operatorname{atan}\left(\frac{\sqrt{C^2 + S^2}}{N}\right)$ $\%\_Depolarization = 100 \cdot (1 - N^2 - C^2 - S^2)$ and if the Analyzer Azimuth 'A' is set to forty-five (45) degrees, and they can be calculated without even measuring the D.C. component of the signal, although the D.C. component remains necessary to enable calculating Depolarization, (as in Eq. 70)

$$\Delta = \text{atan}\left(\frac{cR}{sR} \cdot \frac{A2 \cdot S2P - B2C2P}{A4 \cdot S2P - B4 \cdot C2P}\right) \qquad 70$$

$$\Psi = \text{atan}\left[\frac{\sqrt{\left(\frac{cR}{sR}\right)^2 \cdot (-A2 \cdot S2P + B2 \cdot C2P)^2}}{A4 \cdot C2P + B4 \cdot S2P}\right]$$

Where birefringent window(s) or lens(es) are present in the ellipsometric beam pathway and are characterized in terms of in-plane and out-of-plane retardance components, (as described in Allowed Patent application Ser. No. 09/162,217, said 217 Application being incorporated hereinto by reference), the true N, C and S Parameters can be extracted from measured Fourier Coefficients using Eqs. 71. Note that out-of-plane window retardance effects on the data are analytically removed using these expressions:

$$N = \frac{((sR \cdot cr1 + sR \cdot rDC \cdot C2P \cdot C2A \cdot cr2) \cdot a4 - cR \cdot a2 \cdot sr1 + sR \cdot b4 \cdot rDC \cdot S2P \cdot cr2 \cdot C2A - sR \cdot cr2 \cdot C2A \cdot cR)}{((sR \cdot C2P \cdot rDC + sR \cdot cr1 \cdot cr2 \cdot C2A) \cdot a4 - sR \cdot cR + S2P \cdot b4 \cdot sR \cdot rDC - cR \cdot sr1 \cdot a2 \cdot C2A \cdot cr2)} \qquad 71$$

$$C = \frac{\begin{bmatrix}(-sR2 \cdot cR \cdot C2A \cdot (cr2 \cdot C2A + rDC \cdot C2P \cdot cr1)) \cdot a2 \ldots + \\ sR \cdot (C2A \cdot cr2 \cdot cr1S2A + rDC \cdot C2P \cdot S2A + rDC \cdot S2P \cdot sr2 \cdot C2A \cdot sr1) \cdot b4 - sR \cdot cR \cdot sr2 \cdot C2A \cdot sr1\end{bmatrix} \cdot N \ldots + \\ (cR \cdot sr2 \cdot C2A^2 \cdot rDC \cdot C2P \cdot cr1 \cdot cr2 + cR \cdot sr2 \cdot C2A) \cdot a2 + \\ (-sR \cdot rDC \cdot C2P \cdot S2A \cdot C2A \cdot cr2 - sR \cdot cr1 \cdot S2A - sR \cdot rDC \cdot S2P \cdot sr2 \cdot C2A^2 \cdot sr1 \cdot cr2) \cdot b4 + \\ cR \cdot sr2 \cdot C2A^2 \cdot sR \cdot sr1 \cdot cr2}{(S2A^2 + C2A^2 \cdot sr2^2) \cdot (sR \cdot b4 \cdot rDC \cdot S2P \cdot cr1 + cR \cdot a2 \cdot rDC \cdot C2P \cdot sr1 - sR \cdot cR \cdot cr1)}$$

$$S = \frac{\begin{array}{l}(((C2A \cdot cr2 + rDC \cdot C2P \cdot cr1) \cdot a2 + sR \cdot sr1) \cdot N + ((C2A \cdot sr2 - S2P \cdot S2A) \cdot \\ a2 \cdot rDC - sR \cdot sr2 \cdot cr1 \cdot C2A) \cdot C) \ldots + ((-1 - rDC \cdot C2P \cdot cr1 \cdot cr2 \cdot C2A) \cdot a2 - sR \cdot sr1 \cdot C2A \cdot cr2)\end{array}}{(C2P \cdot sr1 \cdot S2A + sr2 \cdot C2A \cdot S2P) \cdot a2 \cdot rDC - sR \cdot cr1 \cdot S2A}$$

where:
$cr1 = \cos(r1)$, $sr1 = \sin(r1)$, $cr2 = \cos(r2)$, $sr2 = \sin(r2)$,
$r1$ = out-of-plane entrance window retardance, $r2$ = out-of-plane exit window retardance It is noted that parameterization in calibration procedures can include DELTA offset due to birefringent effects of windows and/or lenses through which a beam of electromagnetic radiation passes, as well as wavelength offsets, (eg. wherein a calculated curve is shifted along a wavelength axis while retaining its general shape by any means), Global Regression Mode (GRM) 4

In this (GRM) 4 Mode Material System, (Sample), PSI and DELTA are Parameterized as function of Reference Sample Surface Layer Thickness and Angle Of Incidence using well known optical model and optical constants for the substrate and film, and Compensator and Analyzer Characterizing Parameters are fit at each Wavelength. This serves to pick-up subtlties in Retardance, Fast Axis Position and Rotation.

(GRM) 4 provides:

$$PFD_{PN}(P, \Psi(T,\theta), \Delta(T,\theta), gAs, (C_s)_N, (P_s)_N, \delta_N) \qquad 72$$

provides that Reference Material System, (Sample), PSI and DELTA parameters can be parameterized as functions of:

Reference Material System, (Sample), and or Surface Layer thereupon Thickness;

Angle of Incidence of the Electromagnetic Beam to a Reference Material System (Sample) surface;

in addition to what is shown infra in the previously reported (GRM) 3 which is described by Eq. 49.

It is also disclosed that the disclosed invention allows calculating Reflectance by using un-normalized A.C. and/or D.C. signals. As mentioned, the Kleim et al. Article cited in the Background Section, provides:

$$I = I_0 \cdot (DC + a2 \cdot \cos(2\omega t) + b2 \cdot \sin(2\omega t) + \qquad 73$$
$$\qquad a4 \cdot \cos(4\omega t) + b4 \cdot \sin(4 \cdot \omega t))$$
$$I_0 = K \cdot R_s$$
$$R_s = \frac{r_p \cdot \overline{r_p} + r_s \cdot \overline{r_s}}{2}$$
$$M_s = R_s \begin{pmatrix} 1 & -N & 0 & 0 \\ -N & 1 & 0 & 0 \\ 0 & 0 & C & S \\ 0 & 0 & -S & C \end{pmatrix}$$
$$DC = \frac{1}{2} \cdot (1 + \cos\delta) \cdot (\cos2A \cdot \cos2P - \cos2P \cdot N +$$
$$\qquad \sin2A - \sin2P \cdot C) - \cos2A \cdot N + 1$$
$$a2 = -\sin2A \cdot \sin2P \cdot \sin\delta \cdot S$$
$$b2 = \sin2A \cdot \cos2P \cdot \sin\delta \cdot S$$
$$a4 = \frac{1}{2} \cdot (1 - \cos\delta) \cdot (\cos2A \cdot \cos2P -$$
$$\qquad \cos2P \cdot N - \sin2A \cdot \sin2P \cdot C)$$
$$b4 = \frac{1}{2} \cdot (1 - \cos\delta) \cdot (\cos2A \cdot \sin2P - \sin2P \cdot$$
$$\qquad N + \sin2A \cdot \cos2P \cdot C)$$

where: 'ω' is the rotational frequency of the rotating compensator element, "δ" is the retardance of the compensator, I0 is the average intensity of the detected signal, Ms is the Mueller Matrix representation of an isotropic sample, and Rs is the average Reflectance of the sample. Note that for most ellipsometric applications, Rs is lumped together with an arbitrary system throughput constant K, (K is a function of the light source intensity, detector sensitivity, and electronic gain). Both K and Rs cancel from the above expressions if the Fourier Coefficients (a2, b2, a4 and/or b4) are normalized, either by dividing by the D.C. term, or dividing by the magnitude of the A.C. coefficients. However, if nomalization is not performed, K and Rs information is present in the detected signal, in both the D.C. and A.C. (ie. Fourier Coefficients), signals.

While Rs information could be derived from the D.C. component of the signal, and D.C. offsets or drigts in the detector electronic would degrade the accuracy of the Rs data. Likewise, changes in ambient light collected by the detector would also couple into the measured D.C. signal, and thereby corrupt the Rs determination.

However, using the A.C. signal is a more robust way to determine Rs, as locking into the modulated signal eliminates the problems previously described with utilizing the D.C. component. Assumin an analyzer azimuth of +/−45 degrees, the magnitude of the A.C. signal 2ω and 4ω components are:

$$I_0^2 \cdot (a2^2 + b2^2) = K^2 \cdot R_s^2 \cdot \sin\delta^2 \cdot S^2$$

$$I_0^2 \cdot (a4^2 + b4^2) = K^2 \cdot R_s^2 \cdot \frac{1}{4} \cdot (C^2 + N^2) \cdot (\cos\delta - 1)^2$$

Since $N^2 + C^2 + S^2 = f$ or a non-depolarizing sample, the following expressions can be written:

$$S^2 = \frac{I_0^2 \cdot (a2^2 + b2^2)}{K^2 \cdot R_s^2 \cdot \sin\delta^2}$$

$$(C^2 + N^2) = \frac{4 \cdot I_0^2 \cdot (a4^2 + b4^2)}{K^2 \cdot R_s^2 \cdot (\cos\delta - 1)^2}$$

$$N^2 + C^2 + S^2 = 1 = \frac{I_0^2 \cdot (a2^2 + b2^2)}{K^2 \cdot R_s^2 \cdot \sin\delta^2} + \frac{4 \cdot I_0^2 \cdot (a4^2 + b4^2)}{K^2 \cdot R_s^2 \cdot (\cos\delta - 1)^2}$$

$$K \cdot R_s = \sqrt{\frac{[(I_0 \cdot a2)^2 + (I_0 \cdot b2)^2]}{\sin\delta^2} + \frac{4 \cdot [(I_0 \cdot a4)^2 + (I_0 \cdot b4)^2]}{(\cos\delta - 1)^2}}$$

74

Using the above expression, the K*Rs product can be determined using only the un-normalized A.C. components of the detected signal. To determine K, such that Rs can be calculated requires a calibration using a reference sample which has a known reflectance. The best way to do this would be to measure and fit an optical model to ellipsometric data acquired from a reference sample. The optical model derived from the ellipsometric data could then be used to calculate the average sample reflectance Rs, and then the system throughput constant K could be determined and fixed for subsequent merasurements, allowing the unique determination of Rs using only A.C. signal components. Similar expressions can be either analytically derived or numerically evaluated to determine Rs from the A.C. components when the analyzer is not exactly +/−45 degrees, or if the compensator non-idealities require more complicated expressions for the Fourier coefficients. Stated generally, Sample Reflectance is determined from the detector output signal without application of normalizion to any D.C. and/or A.C. components thereof.

It is noted that use of Reflectance as determined from un-normalized data, preferably un-normlized A.C. data, but not excluding using un-normalized D.C. and/or A.C. data, can be useful in system calibration, particularly where sample defining parameters are simultaneously determined.

Finally, as it is of primary importance to the disclosed invention, it is to be specifically understood that the practice of ellipsometry involves characterizing electromagentic beams as being comprised of two orthogonal components, each of which has a magnitude, which orthogonal components are separated by a phase angle. Compensators enter retardation between the orthogonal components and thereby increase the phase angle therebetween. A rotating Compensator causes varying retardation between the orthogonal components over time.

The invention will be better understood by reference to the Detailed Description Section of this Disclosure, in conjunction with the accompanying Drawings.

SUMMARY OF THE INVENTION

It is therefore a primary purpose and/or objective of the invention to teach a spectroscopic ellipsometer for evaluating a sample comprising:

a broadband light source generating a beam having wavelengths extending over a range of at least 200 to 800 nm;

a polarizer disposed in the path of the light beam;

a compensator disposed in the path of the light beam, said compensator for inducing phase retardations in the polarization state of the light beam, said compensator having characteristics other than substantially non-achromatic so that the amount of phase retardation varies with wavelength, over a range of wavelengths, less than is the case were a substantially non-achromatic compensator utilized, said compensator being rotated at an angular frequency of ω;

an analyzer that interacts with the light beam after the beam interacts with the sample and with the compensator;

a detector that measure the intensity of the light beam after the interaction with the analyzer at a plurality of wavelengths across the wavelength range of at least 200 to 800 nm;

said detector generating a time varying intensity output signal simultaneously comprising 2ω and 4ω components; and optionally a processor for evaluating the sample based on the intensity output signal without, after the detector determines Intensity, the requirement that a 2ω component and a 4ω component be provided other than as used simultaneously in sample characterization.

It is another primary purpose and/or objective of the invention to teach a spectroscopic ellipsometer system which comproses a broadband electromagnetic radiation source means generating a beam having a wavelength extending between over a range of at least 200 to 800 nm; polarizer means disposed in the path of said beam; compensator(s) means disposed in the path of the beam, said compensator(s) means having characteristics selected from the group consisting of:

being substantially achromatic;

being pseudo-achromatic;

being other than substantially-non-achromatic;

so that the amount of phase retardation varies with wavelength less than is the case were a substantially non-achromatic compensator utilized, said compensator(s) means being rotated at an angular frequency of ω;

analyzer means that interact with the beam after the beam interacts with the sample and the compensator(s) means;

detector means that measure the intensity of the beam after the interaction with the analyzer means at a plurality of wavelengths across the wavelength range of at least 200 to 800 nm; said detector means generating a time varying intensity output signal comprising 2ω and 4ω component signals, said 2ω and 4ω signal components being simultaneously present at all wavelengths measured unless the 2ω singal is force to 0.0 by a sample presenting with an ellipsometric DELTA of 0.0 as opposed to being to caused to be 0.0 by said compensators means; and optionally further processor means for evaluating the sample based simultaneously on both the 2ω and 4ω intensity signal components at measured wavelengths.

It is yet another primary purpose and/or objective of the invention to teach a spectroscopic ellipsometer system comprising broadband electromagnetic radiation source means generating a beam having a wavelength extending between over a range of at least 200 to 800 nm; polarizer means disposed in the path of said beam; compensator(s) means disposed in the path of the beam, said compensator(s) means being:

pseudo-achromatic;

in that the amount of phase retardation varies more with wavelength than is the case if a substantially achromatic compensator is utilized but in that the amount of phase retardation varies less than is the case if a substantially non-achromatic compensator is utilized, said compensator mean(s) means being rotated at an angular frequency of ω; analyzer means that interacts with the beam after the beam interacts with the sample and the compensator(s) means; detector means that measure the intensity of the beam after the interaction with the analyzer at a plurality of wavelengths across the wavelength range of at least 200 to 800 nm; said detector means generating a time varying intensity signal comprsing 2ω and 4ω component signals, said 2ω and 4ω signals being simultaneously present at all wavelengths measured unless the 2ω signal is forced to 0.0 by a sample presenting with an ellipsometric DELTA of 0.0 as opposed to being caused to be 0.0 by said compensator(s) means; and optionally further comprising processor means for evaluating the sample based simultaneously on both the 2ω and 4ω intensity signal components at measured wavelengths.

It is another objective and/or purpose of the invention to teach use of compensators in Spectroscopic Ellipsometers including Rotating Compensators which provide retardations in a range, (ie. max–min) of less than 90 degrees within a range of retardations bounded by at least 30 to less than 135 degrees, (thereby excluding 180 degrees), over a range of wavelengths.

It is another objective and/or purpose yet of the invention to teach a Spectroscopic Rotating Compensator Material System Investigation System, including at least one Photo Array comprised of a multiplicity of Diode Elements, for simultaneously detecting a Multiplicity of Wavelengths, which Spectroscopic Rotating Compensator Material System Investigation System can utilize both Achromatic and non-Achromatic Compensators of Berek-type with Optical Axis perpendicular to a surface thereof, and/or with Compensators with Optical Axis parallel to a surface thereof; and which Spectroscopic Rotating Compensator Material System Investigation System can be realized utilizing off-the-shelf Compensator and Spectrometer System components.

It is a further objective and/or purpose of the invention to teach that a preferred Compensator Design is comprised of a combination of a first and a second actual or effective zero-order wave plate, said first actual or effective zero-order wave plate being either a single zero-order waveplate or being comprised of two multiple order waveplates which are combined with the fast axes thereof oriented at a nominal ninety degrees to one another, and said second actual or effective zero-order wave plate being either a single zero-order waveplate or comprised of two multiple order waveplates which are combined with the fast axes thereof oriented at a nominal ninety degrees to one another; the fast axes of the multiple order waveplate(s) in said second actual or effective zero-order wave plate being oriented at other than zero or ninety degrees, nominally forty-five degrees, to the fast axes, respectively, of the multiple order waveplate(s) in said first actual or effective zero-order waveplate.

It is another objective and/or purpose of the invention to teach, in the context of a Spectroscopic Rotating Compensator Material System Investigation System, Evaluation of Calibration Parameters in a Mathematical Model thereof by a Mathematical Regression based technique involving utilization of at least one, at least-one-dimensional data set, obtained with the Spectroscopic Rotating Compensator Material System Investigation System oriented in a "Material System, (Sample), present" or in a "Straight-through" configuration.

It is yet another objective and/or purpose of the invention to teach, in the context of a Spectroscopic Rotating Compensator Material System Investigation System, Evaluation of Calibration Parameters in a Mathematical Model thereof by a Mathematical Regression based technique involving utilization of at least one multi-dimensional, data set(s) being obtained utilizing a selection from the group consiting of:

- all of said at least one multi-dimensional data set(s), being obtained utilizing a single material system (MS) placed on said stage (STG) for supporting a material system (MS);
- at least one of said at least one multi-dimensional data set(s), being obtained utilizing one material system (MS) placed on said stage (STG) for supporting a material system (MS), with another of said at least one multi-dimensional data set(s), being obtained utilizing another material system (MS) placed on said stage (STG) for supporting a material system (MS); and
- at least one of said at least one multi-dimensional data set(s) being obtained with the spectroscopic rotating compensator material system investigation system oriented in a "straight-through" configuration wherein a polychromatic beam of electromagnetic radiation (PPCLB) produced by said source (LS) of a polychromatic beam of electromagnetic radiation, is caused to pass through said polarizer (P), pass through said analyzer (A), and interact with said dispersive optics (DO) such that a multiplicity of essentially single wavelengths are caused to simultaneously enter a corresponding multiplicity of detector elements (DE's) in said at least one detector system (DET), with said polychromatic beam of electromagnetic radiation (PPCLB) also being caused to pass through at least one compensator(s) (C) (C') (C") but without being caused to interact with any material system (MS) placed on said stage (STG) for supporting a material system (MS) other than open ambient atmosphere.

It is another objective and/or purpose of the invention yet to teach, in the context of a Spectroscopic Rotating Compensator Ellipsometer/Material System Investigation Systems, Evaluation of Calibration Parameters in a Mathematical Model thereof by a Mathematical Regression based technique involving utilization of said at least two, at least one-dimensional, data set(s) being obtained utilizing a selection from the group consiting of:

all of said at least two, at least one-dimensional data set(s), being obtained utilizing a single material system (MS) placed on said stage (STG) for supporting a material system (MS);

at least one of said at least two, at least one-dimensional data set(s) being obtained utilizing one material system (MS) placed on said stage (STG) for supporting a material system (MS), and at least one of said at least two at least one-dimensional data set(s) being obtained utilizing one material system (MS) placed on said stage (STG) for supporting a material system (MS); and at least one of said at least two, at least one-dimensional data set(s) being obtained utilizing one material system (MS) placed on said stage (STG) for supporting a material system (MS), and at least one of said at least two, at least one-dimensional data set(s) being obtained with the spectroscopic rotating compensator material system investigation system oriented in a "straight-through" configuration wherein a polychromatic beam of electromagnetic radiation (PPCLB) produced by said source (LS) of a polychromatic beam of electromagnetic radiation, is caused to pass through said polarizer (P), pass through said analyzer (A), and interact with said dispersive optics (DO) such that a multiplicity of essentially single wavelengths are caused to simultaneously enter a corresponding multiplicity of detector elements (DE's) in said at least one detector system (DET), with said polychromatic beam of electromagnetic radiation (PPCLB) also being caused to pass through at least one compensator(s) (C) (C') (C") but without being caused to interact with any material system (MS) placed on said stage (STG) for supporting a material system (MS) other than open ambient atmosphere.

It is another objective and/or purpose of the invention to teach that, where beneficial and desirable, Parameterization of Calibration Parameters, (such as Azimuthal Orientation Angle of Polarizer, Compensator(s) and Analyzer, and Material System, (Sample), PSI and DELTA, and Compensator Representing Matrix Components), as a function of a Data Set variable, (such as Wavelength, or Polarizer and/or Analyzer Azimuthal Angle Rotation, or Angle-of-Incidence of an electromagnetic beam with respect to a surface of a Material System, (Sample), being investigated, or Thickness of a Material System, (Sample), or Surface Layer thereupon, or a DELTA Offset resulting from passage of the electromagnetic beam through a Birefringent Window or Lens, or a Wavelength Shift from a calculated ideal etc.), to reduce the number of Calibration Parameters which need be evaluated during a mathematical regression based Calibration Procedure, should be practiced.

It is yet another objective and/or purpose of the invention, to teach, in the context of a Spectroscopic Rotating Compensator Material System Investigation System, Evaluation of Calibration Parameters in a Mathematical Model thereof by a Mathematical Regression based technique involving utilization of data set(s) which are normalized utilizing a selection from the group consisting of:

a data set D.C. component;

a data set A.C. component;

a parameter derived from a combinations of a data set D.C. component and a data set A.C. component;

It is another purpose and/or objective of the invention to teach measurement of reflectance using un-normalized A.C. and/or D.C. components.

It is a general objective and/or purpose of the present Disclosure to provide experimentally determined documentation of the utility of the Spectroscopic Rotating Compensator Material System Investigation System, in the form of results obtained from practice of the Mathematical Regression Calibration Method, and the Material System Investigation Data Acquisition Method.

It is another purpose and/or objective of the disclosed invention to disclose use of Compensators in which a Fast Axis Azimuthal Orientation varies with wavelength.

It is a general objective and/or purpose of the present Disclosure to provide experimentally determined documentation of the utility of the Spectroscopic Rotating Compensator Material System Investigation System, in the form of results obtained from practice of the Mathematical Regression Calibration Method, and the Material System Investigation Data Acquisition Method.

Other objectives and/or purposes will become obvious by a reading of the Specification.

BRIEF DESCRIPTION OF THE DRAWINGS

FIGS. 9g1, 9h and 9i demonstrates construction of a preferred compensator system constructed from first and second effective Zero-Order Waveplates, each of which effective Zero-Order Waveplates is a constructed composite of two Multiple Order waveplates, the fast axes of which at least two composite effective Zero-Order Waveplates are oriented away from zero or ninety degrees, and at a nominal forty-five degrees, with respect to one another. Optional additional third element(s) are indicated by dashed lines.

FIG. 9g2 shows three Zero Order Plates are contacted to one another instead of having space thereinbetween. Three element Compensators configured as suggested by FIGS. 9g1, 9g2 and 9j can comprise a "Psuedo Achromatic" which can provide Retardation vs. Wavelength characteristics such as those presented in FIG. 10g2.

FIG. 9j demonstrates functional construction of another preferred compensator system constructed from first and second actual per se. Zero-Order Waveplates, each of which actual per se. Zero-Order Waveplate is an effective signle plate, the fast axes of which at least two composite actual per se. Zero-Order Waveplates are oriented away from zero or ninety degrees, and at a nominal forty-five degrees, with respect to one another.

FIG. 9k shows a diagram demonstrating use of beam splitters to direct an incident electromagnetic beam into two detectors.

FIG. 9l shows a "polka-dot" beam splitter.

Figure 1:
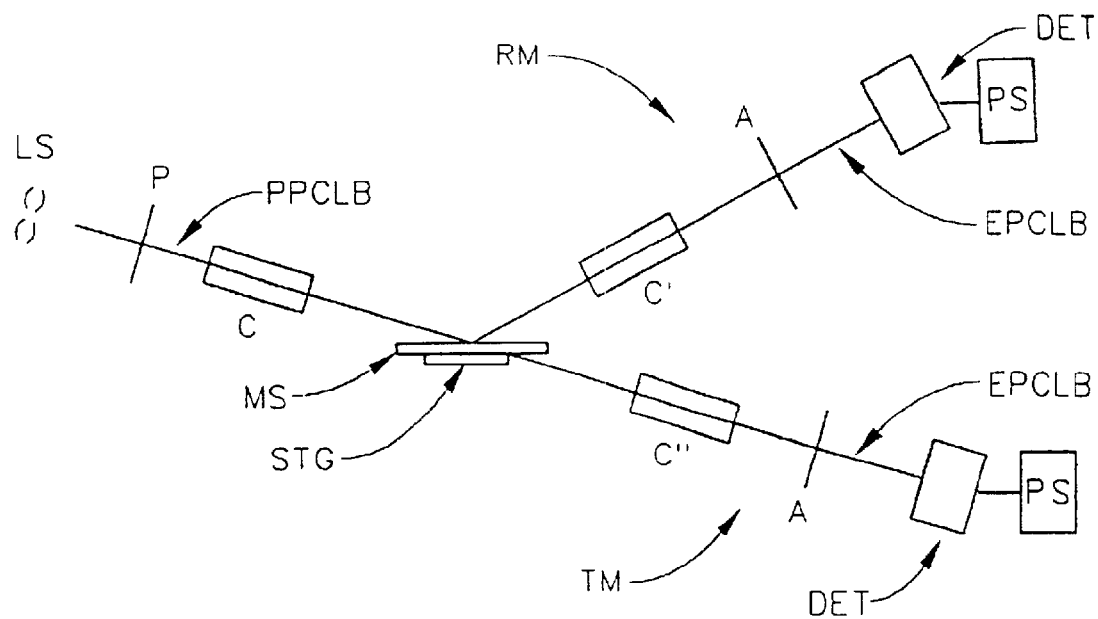
FIG. 1 shows the basic components of Reflectance and Transmission Mode Material System Investigation Systems which can be operated in Spectroscopic Rotating Compensator Material System Investigation System (eg. Ellipsometer System), Modes.

Note that FIGS. 9g1 and 9i show optional third elements present as dashed-lines. Addition of elements allows achieving a Compensator that provides better Psuedo-Achromatic charactreistics than does a single or dual element Compensator.

Figure 10A:
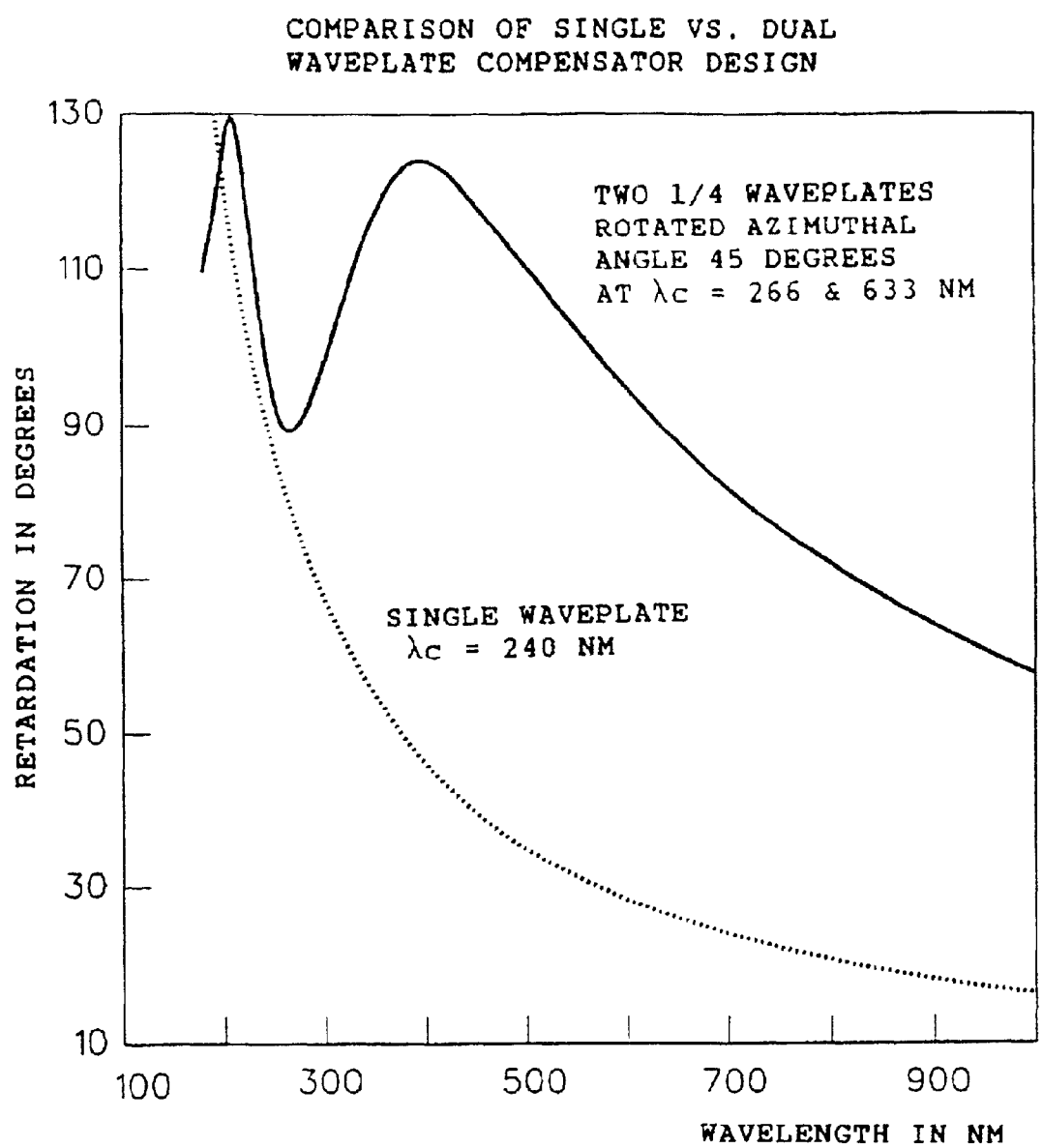
FIG. 10a shows a plot of a compensator retardation characteristic which depends as (1/wavelength), (dashed line), as well as a compensator charactristic, (solid line).
Figure 10B:
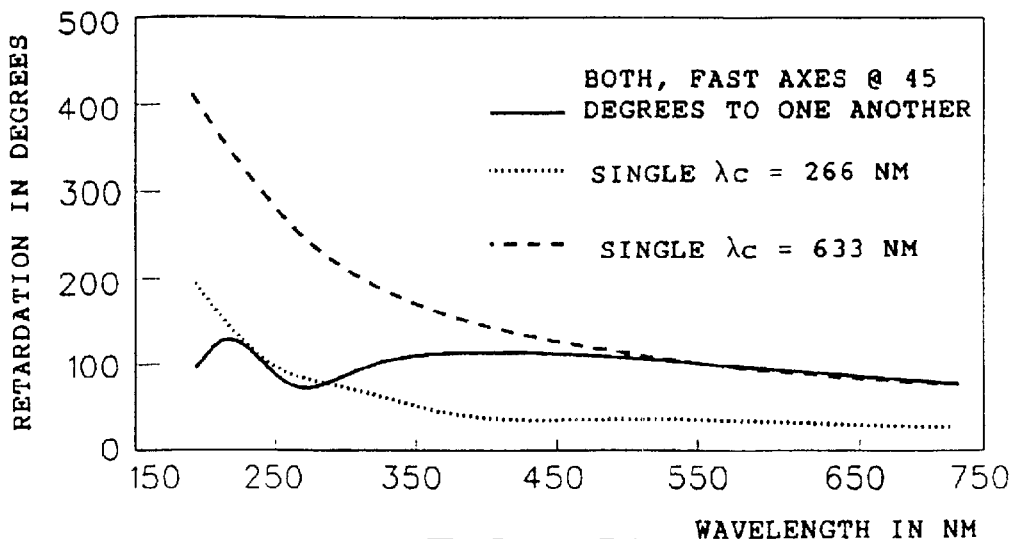
FIG. 10b shows calculated retardation vs. wavelength curves for two compensators which demonstrate (1/wavelength) retardation characterics, (long and short dashed lines), and the retardation curve, (solid line), of an assembly as demonstrated in FIG. 9g1 which is arrived at by combining said two retarders with a 45 degree angle between the fast axes thereof.
Figure 10C:
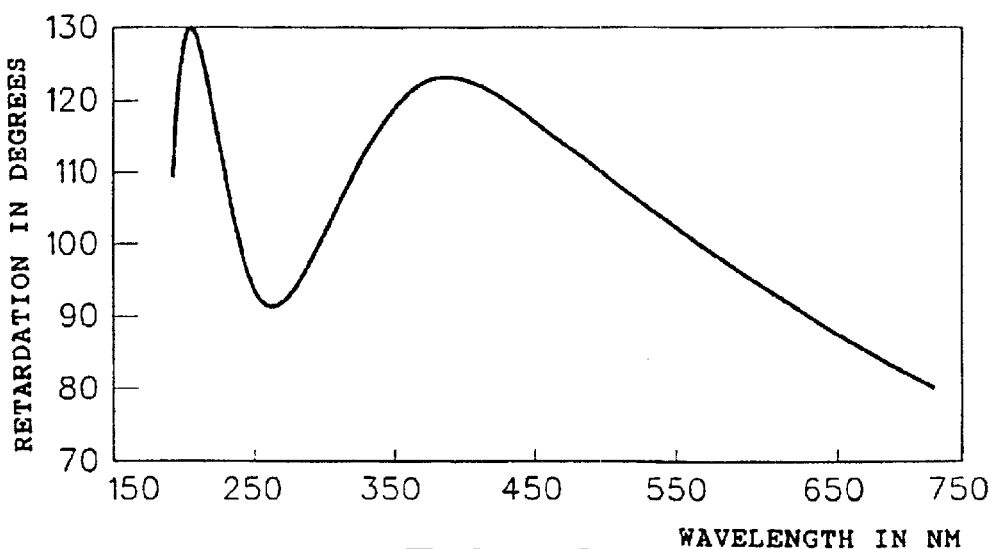

FIG. 10c shows a rescaled plot of the solid line curve shown in FIG. 10b.

Figure 9A:
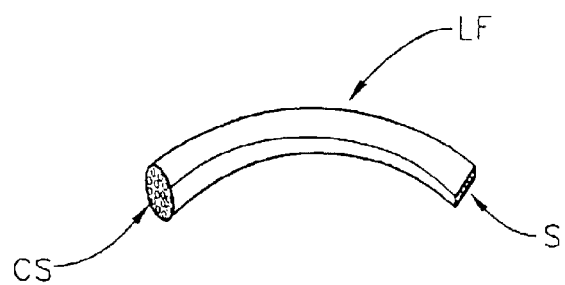
FIG. 9a shows a Fiber Optic which is essentially circular at the left side and which becomes of a "slit" shape at the right side.
Figure 10D:
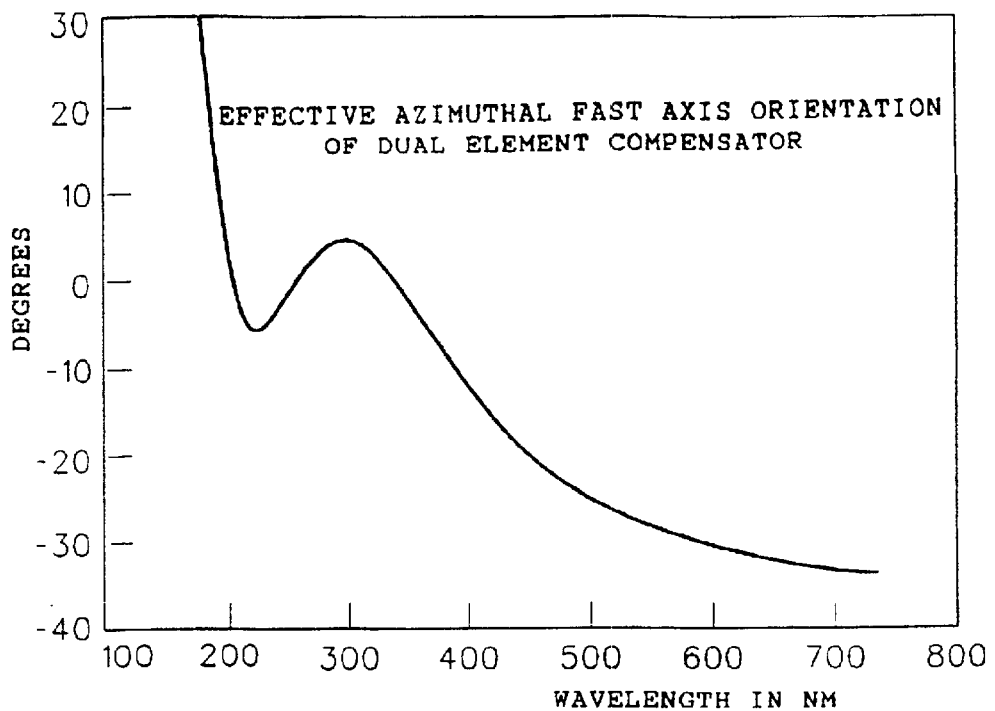
Figure 10E:
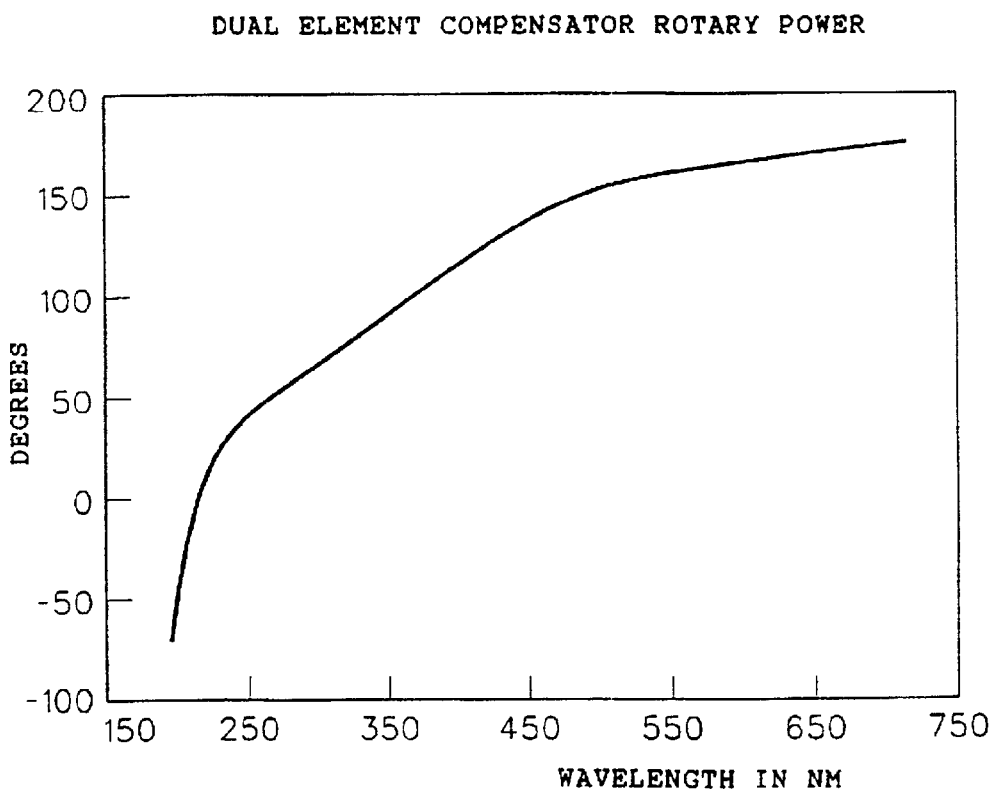

FIGS. 10d and 10e show results calculated for compensators as demonstrated in FIG. 9g1, wherein one waveplate is selected at 266 NM and the other at 633 NM., and wherein the fast axes are oriented at 45 degrees with respect to one another, over a wavelength range of from 190 to 730 NM.

FIGS. 10f and 10g1 show that changing waveplate selection for a FIG. 9g1 compensator configuration, and the angle between fast axes thereof, provides alternative retardation plots over various wavelength ranges.

Figure 2:
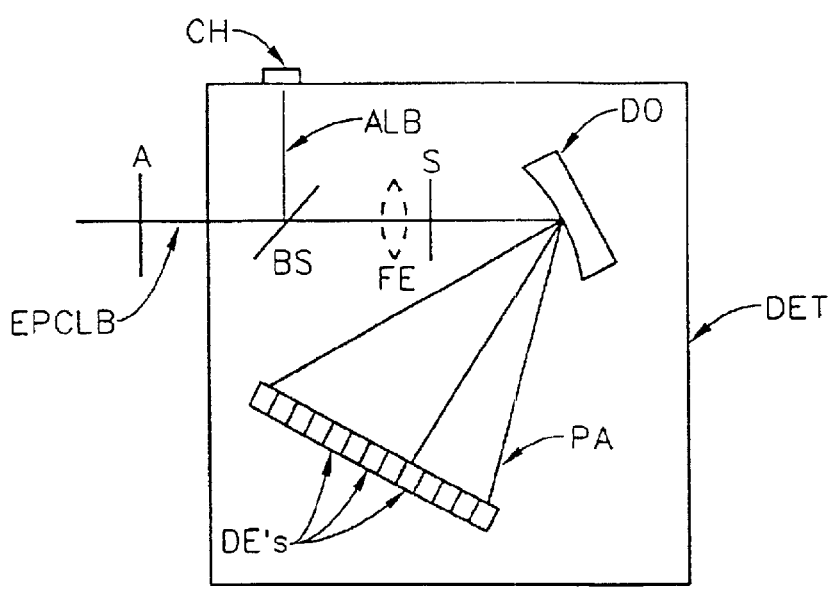
FIG. 2 shows a Spectrographic Diode Array Spectrometer System Detector.

FIG. 10g2 shows retardation vs. wavelength for a three (3) Zero Order plate compensator. The retardation varies between about 47 degrees and 130 degrees over a wavelength range of 190 to 1700 nm. Said three (3) element compensator comprises a 422 nm quartz Zero Order waveplate sandwiched by two 633 nm quartz Zero Order waveplates. FIGS. 9g1 and 9j, wherein the dashed lines represent a present third waveplate, demonstrate the physical realization.

Figure 10H:
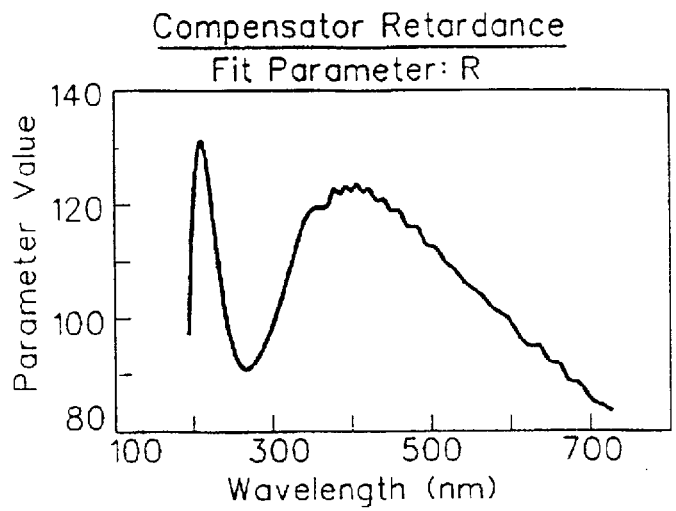

FIG. 10h shows experimentally determined Compensator Retardance as a function of Wavelength. Note that, except for the presence of harmonic "wiggles", the curve closely corresponds to the calculated curve in FIG. 10c.

Figure 10I:
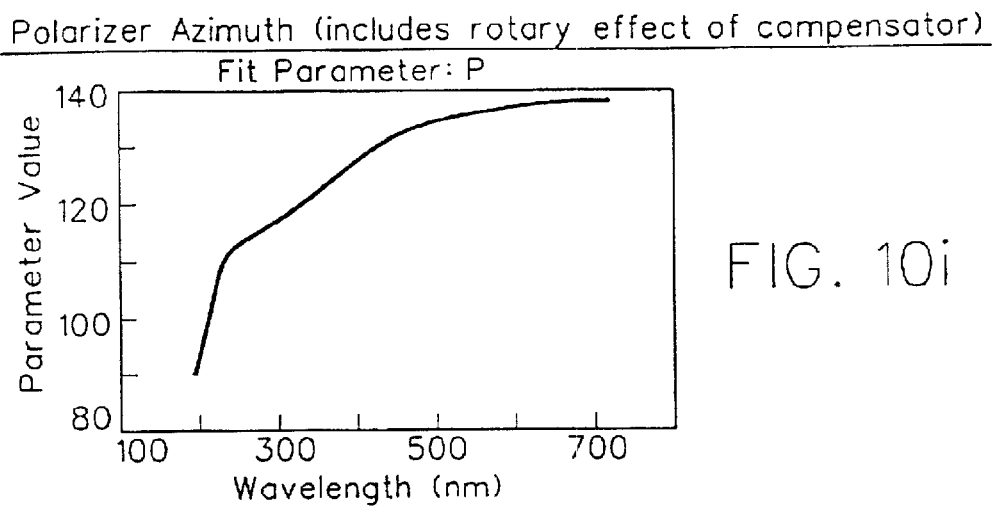

FIG. 10i shows experimentally determined Effective Input Polarizer Azimuthal Angle, (including the rotary effect of the Compensator). Note the agreement with FIG. 10e.

Figure 10J:
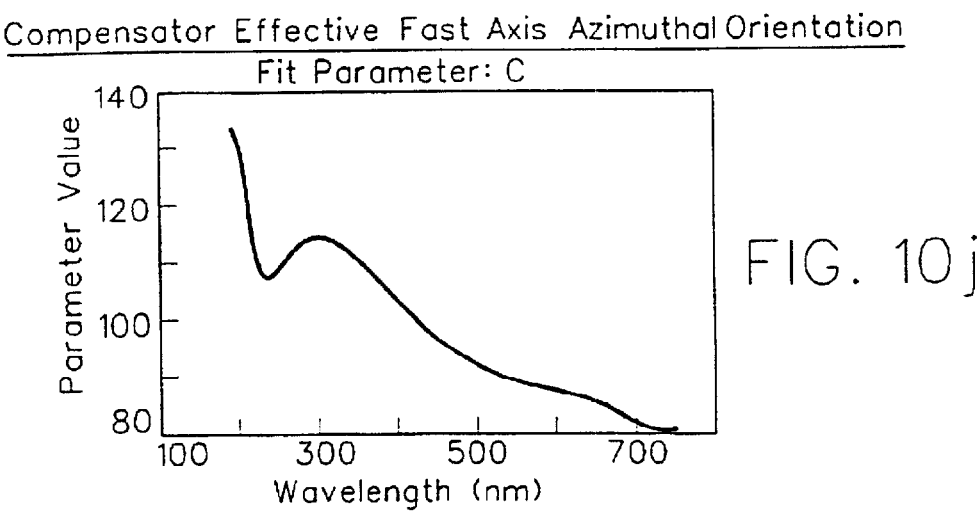
Figure 10K:
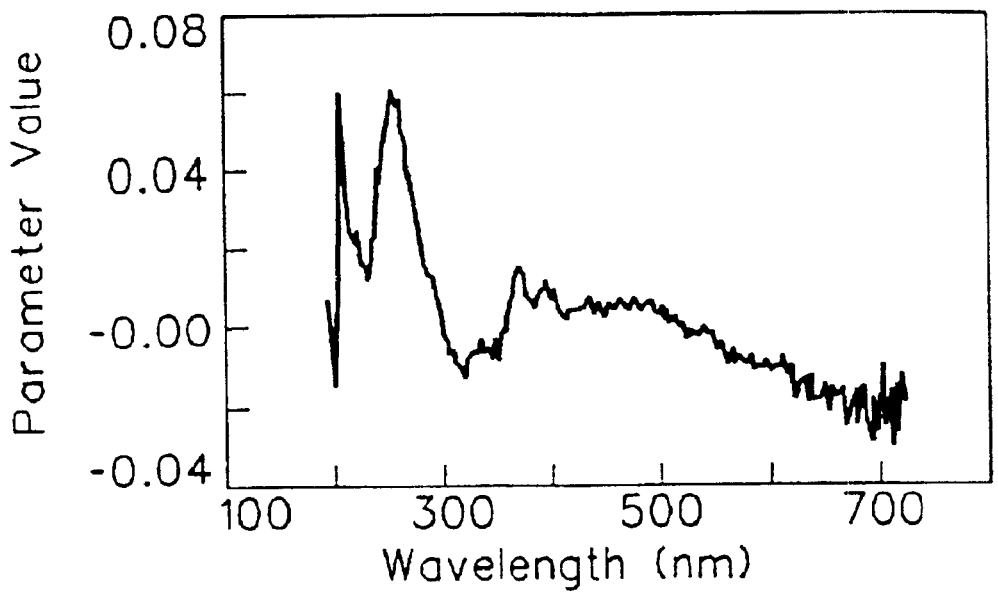
Figure 10L:
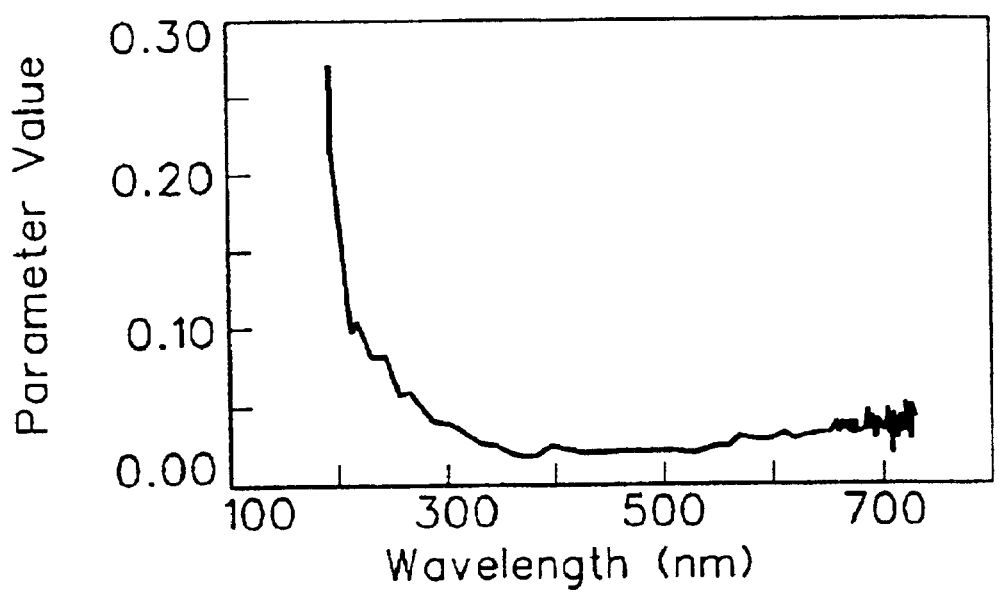

FIG. 10j shows the experimentally determined effective Fast Axis of the Compensator Azimuthal Orientation. Note the agreement with FIG. 10d FIGS. 10k and 10L show experimentally determined Depolarization factors 'c' factor 'b' as defined in Eqs. 67.

Figure 10M:
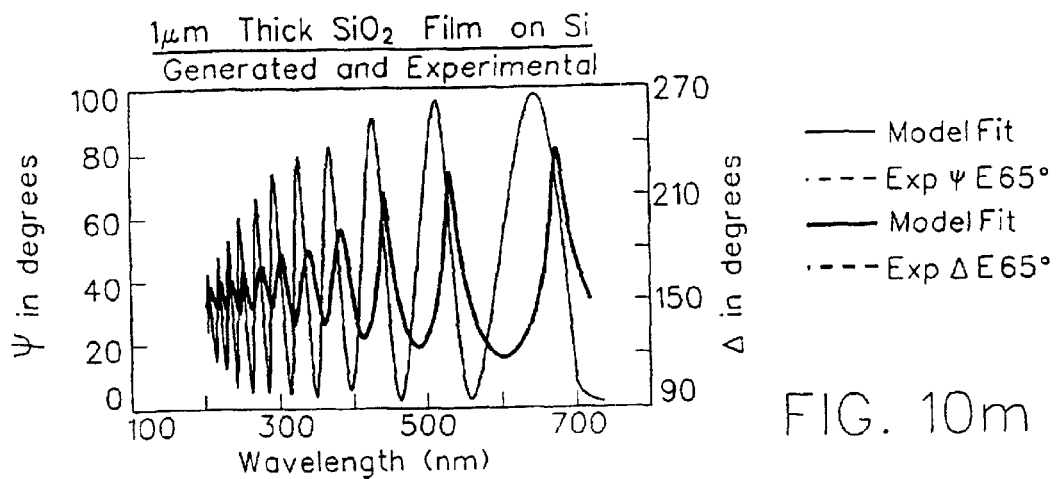
Figure 10N:
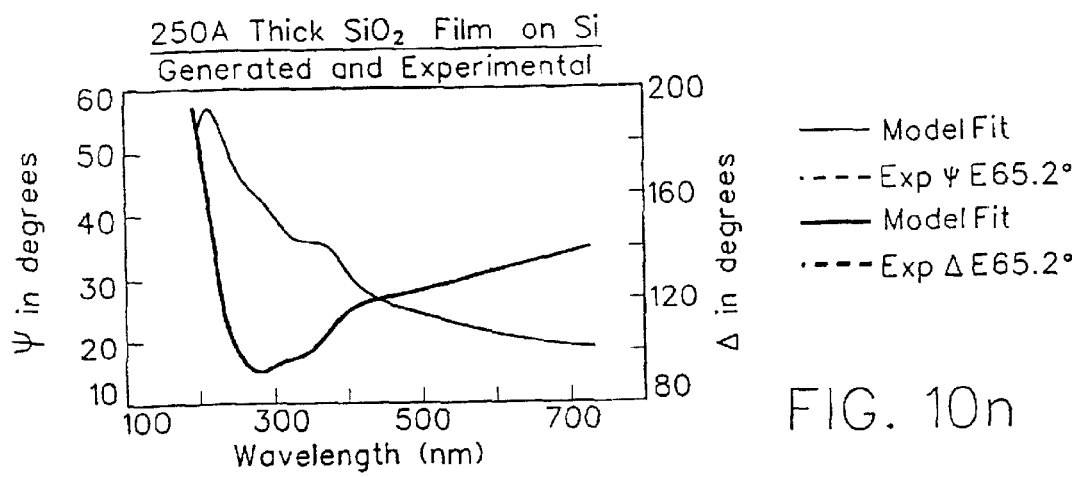
Figure 10O:
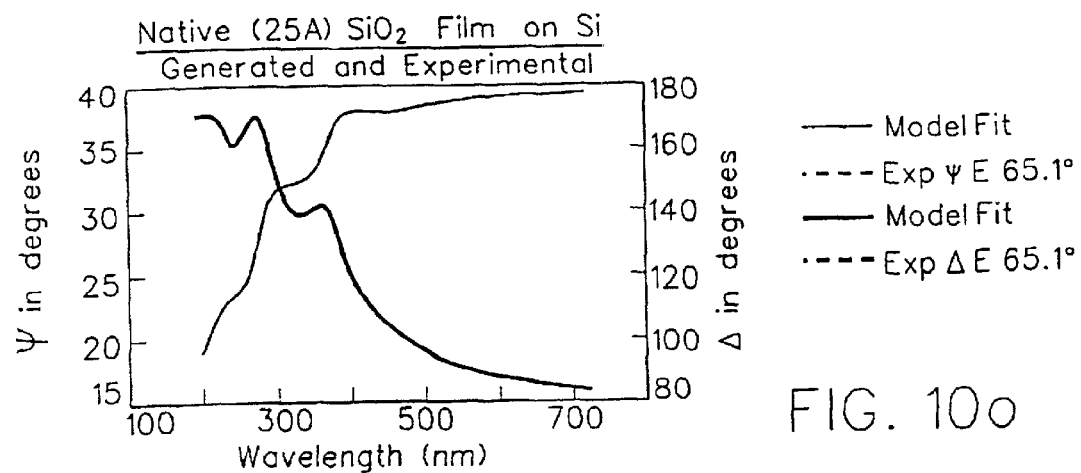

FIGS. 10m-10o show PSI and DELTA Curves experimentally determined for Silicon Substrates with, rspectively, 1 Micron, 250 Angstroms and 25 Angstroms of $SiO_2$ on the surface thereof.

The experimentally determined data is essentially exact agreement with the generated data from a mathematical model fit.

DETAILED DESCRIPTION

Invention System

Referring now to FIG. 1, there is demonstrated a Material System Investigation System, (ie. a Spectroscopic Ellipsometer System), with provision to investigate a Material System, (Sample), (MS) in either a Reflection Mode (RM) or a Transmission Mode (TM). It is to be noted that said Material System investigation System is generally comprised of a Source of a Polychromatic Beam of Electromagnetic Radiation (LS), (ie. a Broadband electromagnetic radiation source), a Polarizer Means (P), a Material System, (ie. Sample), supporting Stage (STG), an Analyzer Means (A) and a Detector Elements (DE's) containing Photo Array Detector Means System (DET). Also note, however, that FIG. 1 shows Reflection Mode System Compensator(s) Means (C) and (C') and Transmission Mode System Compensator(s) Means (C) and (C") as present. It is to be understood that a compensator Means can be placed ahead of, and/or after a Material System, (Sample), (MS) supporting Stage (STG) in either a Reflection Mode or Transmission Mode System. That is only Compensator Means (C) or (C') or both Compensator Means (C) and (C') can be present in a Reflection Mode System (RM), and only Compensator Means (C) or (C") or both Compensator Means (C) and (C") can be simultaneously present in the Transmission Mode System (TM). FIG. 1 also shows the presence of a Processor (PS) for performing calculations that evaluate a sample based on the Detector (DET) intensity output signal, without separating it into separate 2 and 4 component signals. Note that the indicated processor (PS) is not programmed with the same type of algorithm the processor in the Aspnes et al. Patents is interpreted as containing. As the U.S. Pat. No. 6,320,657 File Wrapper shows, the Aspnes et al. detector provides the processor in the Aspnes et al. invention a $2\omega$ and a $4\omega$ signal after determining an intensity. The present invention does not separately use the $2\omega$ and $4\omega$ signal components from a detector provided Intensity, but always operates simultaneously on both the $2\omega$ and $4\omega$ signals simultaneously, even if one, (ie. the $2\omega$ signal), becomes 0.0, said 0.0 simply being valid data indicating the DELTA of the Sample is 0.0. It is noted that the Aspnes et al. 2 signal being 0.0 provides no firm indication that the Sample DELTA is 0.0, as the Compensator therein can effect 180 degrees retardance at one of more wavelengths, which confuses the issue as to why the 2 signal becomes 0.0. Recall that presently disclosed invention "Psuedo-Achromatic" compensators never provide a retardation of 135 degrees or greater, (hence never impose a 180 degree retardation at any wavelength over a range of wavelengths, emphasis added).

Now, the configuration in FIG. 1 could be operated as a Rotating Polarizer or Rotating Analyzer System. The disclosed Rotating Compensator Material System Investigation System, however, in the preferred operational mode, essentially fixes the Polarizer Means (P) and Analyzer Means (A) during Data Acquisition from a Material System (Sample) (MS) which is placed upon the Material System, (Sample), supporting Stage (STG), and causes at least one present Compensator Means ((C), and/or (C') or (C) and/or (C")), to Rotate during said Data Acquisition. This serves to effectively enter a continuously varying retardance between Orthogonal Components in a Polarization Beam of Electromagnetic Radiation exiting said Compensator Means which is caused to rotate. Where two (2) Compensator Means are present, one before (C) and one after ((C') or (C")) a Material System, (Sample), placed upon said Material System, (Sample) (MS) supporting Stage (STG), only one, or both said Compensator Means can be caused to Rotate in use. If both Compensator Means are caused to rotate, both can be rotated a the same rotation speed, or different rotation speeds can be utilized. It is noted that the J.A. Woollam CO. Rotating Compensator Ellipsometer uses a "Stepper Motor" to cause Compensator rotation, and a common signal synchronizes both the Compensator and Detector. An alternative technique is to use a signal derived from the motor to synchronize the detector. It is further noted that fixing the Polarizer Means (P) and Analyzer Means (A) in use provides another benefit in that polarization state sensitivity to input and output optics during data acquisition is essentially non-existent. This allows use of Optic Fibers, Mirrors, Beam Splitters, Lenses etc. for input/output.

It is also mentioned that in the following it will be generally assumed that a Material System, (Sample), (MS) under investigation by a Spectroscopic Rotating Compensator Material System Investigation System is positioned upon the Material System, (Sample), Supporting Stage (STG). This need not be the case, as is described in U.S. Pat. No. 5,706,087. For instance, a Material System (Sample), (MS) can be positioned in a Magneto-Optic System which is physically too large to be supported by said Material System, (Sample), Supporting Stage (STG). In such a case, an Electromagnetic Beam Directing Means (eg. a Mooney Rhomb or a Mirror etc), can be placed upon said Material System, (Sample), Supporting Stage (STG) and without realigning a Source of Polychromatic Electromagnetic Beam (LS) and said Detector Element (DE) containing Photo Array Detector System (DET), a Polychromatic Electromagnetic Beam provided by said Source of Polychromatic Electromagnetic Beam (LS) can be caused to interact with said remotely positioned Material System, (Sample), (MS), and with said Electromagnetic Beam Directing Means, thereby being directed into said Detector Element (DE) containing Photo array Detector System (DET).

Continuing, the disclosed invention utilizes a Broadband source of Polychromatic Electromagnetic Radiation (LS), and FIG. 2 shows that the Detector Elements (DE's) containing Photo Array Detector System (DET) is, in the preferred embodiment, comprised of a Photo Array which consists of a number of Diode Elements (DE's). In use a Dispersive Optics (DO) receives a Polychromatic Electromagnetic Beam (EPCLB) which has interacted with a Material System, (Sample), (MS) and passed through said Analyzer Means (A), and diffracts said Polychromatic Electromagnetic Beam (EPCLB), such that each Photo Array (PA) Diode Element (DE) intercepts an Essentially Single wavelength, (eg. a small band of wavelengths centered about a central single wavelength). Note that a Focusing Element (FE) is shown in a dashed line format to indicate that its presence is optional. The Focusing Element (FE), when present, serves to provide a focused Polychromatic Beam of Electromagnetic Waves at the input to said Detector Elements (DE's) containing Photo Array Detector System (DET), and the Detector System (DET) provides 2ω and 4ω signals developed by the Diode Elements (DE's) in a sequential output or a parallel output from the Diode Elements (DE's). It is emphasized that a preferred Detector Elements (DE's) containing Photo Array Detector System (DET) is an "Off-the-Shelf-System" which includes a Focusing Element (FE), and provides a self contained Dispersive Optics (DO) and Diode Element (DE) Array. The "Off-The-Shelf-System" of said preferred embodiment of the Rotating Compensator Material System Investigation System is a Zeiss Diode Array Spectrometer System identified by manufacturer numbers in the group: (MMS1 (300–1150 nm); UV/VIS MMS (190–730 nm); UV MMS (190–400 nm); AND IR MMS (900–2400 nm)). Said identified Zeiss systems provide a very compact system comprising a multiplicity of Detector Elements (DE's), and provide focusing via a Focusing Element (FE), Slit (S), and single concave holographic grating dispersive optics (DO), as generally represented by FIG. 2. A Hamamatsu CCD Array Detector, (Series S7030/S7031), with a quantum efficiency of 40% or more has been successfully utilized.

Note that FIG. 2 also shows the presence of a Beam Splitter (BS) and a Cross Hair containing Reticule (CH) in the Detector Elements (DE's) containing Photo Array Detector System (DET). If the Beam Splitter (BS), the Dispersive Optics (DO), the Focusing Element (FE), the Detector Elements (DE's) containing Photo. Array (PA), and the Cross Hair containing Reticule (CH) are mounted so as to move as a rigid unit, then it should be appreciated that causing an Alignment Electromagnetic Radiation Beam (ALB) which reflects to said Cross Hair containing Reticule (CH) to be present near a Cross Hair crossing point can effect good alignment of the Detector Elements (DE's) containing Photo Array Detector System (DET) with respect to an entering Polarized Beam of Electromagnetic Radiation (EPCLB). In practice such an arrangement has been found to work very well. It is further noted that the element identified as (CH) could represent a Quadrature Photodetector and Automatic Alignment Means, or other functionally suitable system.

Figure 8A:
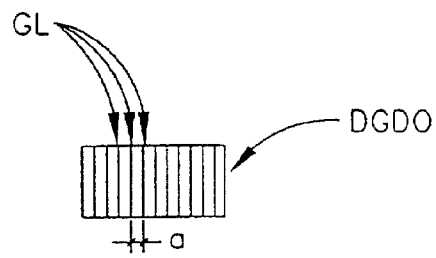
FIG. 8a shows lined diffraction grating dispersion Optics geometry.
Figure 8B:
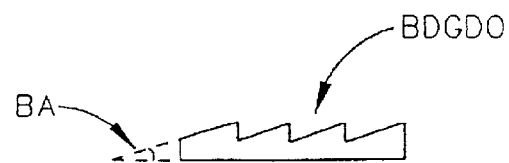
FIG. 8b shows a blazed angle lined diffraction grating dispersion optics geometry.
Figure 8C:
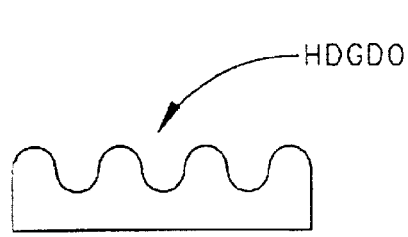
FIG. 8c shows a holographic lined diffraction grating dispersion optics geometry.
Figure 8D:
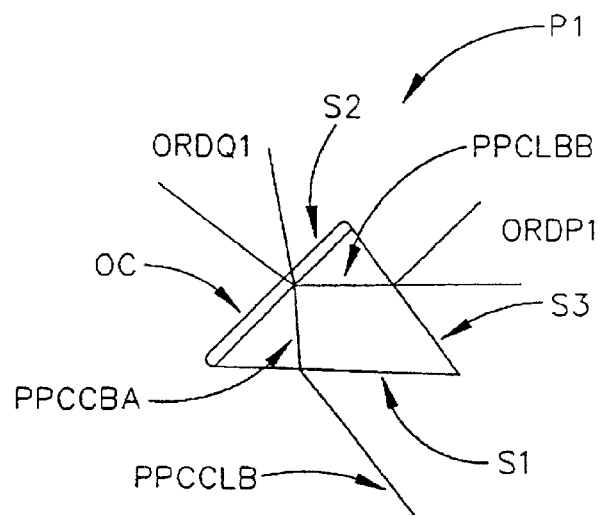
FIG. 8d shows a prism dispersion optics geometry.
Figure 9B:
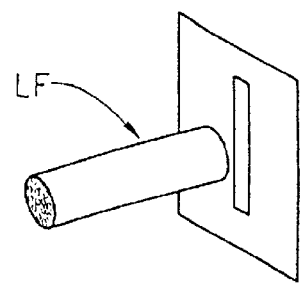
FIG. 9b shows a Fiber Optic which is essentially circular shaped along the entire length thereof, and which provides input to a "Slit" per se.
Figure 9C:
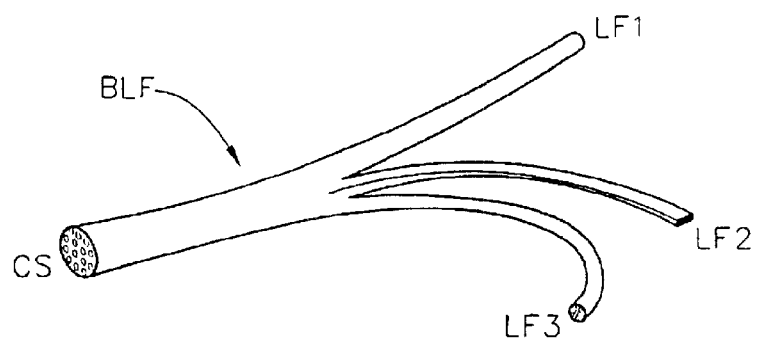
FIG. 9c shows a Trifrucated Fiber Optic which is essentially circular at the left side, which trifrucates and then is exemplified as becoming circular or of a "slit" shape at the right side.
Figure 9D:
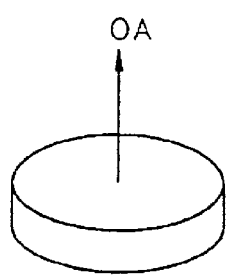
FIG. 9d shows a Berek-type Compensator with an Optical Axis perpendicular to a surface thereof.
Figure 9E:
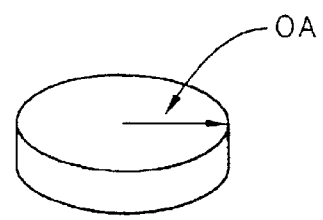
FIG. 9e shows a Compensator with an Optical Axis parallel to a surface thereof.
Figure 9F:
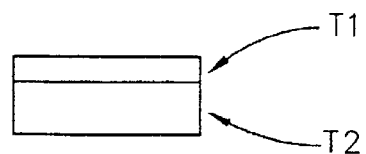
FIG. 9f demonstrates construction of a Zero-Order Quartz Waveplate from two Multiple Order waveplates.

It is also noted that a Compensator Means (C) (C'), (C") can utilize an Off-the-Shelf Quarter-Wave-Plate with its Optical Axis in the plane of a surface thereof, (see FIG. 9e), and that a Pseudo-Zero-Order Waveplate can be constructed from two (2) Multiple-Order Waveplates of different thicknesses (T1) and (T2) which have Optical Axes oriented Ninety (90) degrees to one another, such that the overall effect of retardation is in the Zero-Order, (see FIG. 9f). As discussed in more detail below, FIGS. 9g1-9j show that a particularly relevant Compensator Means involves a combination of two compensators means, each selected from the group consisting of: (actual or pseudo Quarter-Wave-Plates). Also, a Berek-type Compensator with its Optical Axis perpendicular to a surface thereof, (see FIG. 9d), can be is selected without special concern to its Achromatic Operating Characteristics, emphasis added. As well, said Compensator Means (C), (C'), (C") can be made of essentially any functional material such as Quartz or Polymer etc.

FIGS. 9g1, 9h and 9i demonstrate functional construction of a preferred compensator means system constructed from first (ZO1) and second (ZO2) effectively Zero-Order, (eg. Quartz or Bicrystaline Cadnium Sulfide or Bicrystaline Cadnium Selenide), Waveplates, each of which effective Zero-Order Waveplates (ZO1) & (ZO2) is shown to be constructed from two Multiple Order waveplates, (ie. (MOA1) & (MOB1) and (MOA2) & (MOB2), respectively). The fast axes (FAA2) & (FAB2) of said second effective Zero-Order Waveplate (ZO2) are oriented away from zero or ninety degrees, (eg. in a range around a nominal forty-five degrees such as between forty and fifty degrees), with respect to the fast axes (FAA1) & (FAB1) of said first effective Zero-Order Waveplate (ZO1). In particular FIG. 9g1 is a cross-sectional side view of a preferred compensator (PC) constructed from a first effective zero-order plate (ZO1) which is constructed from two multiple order plates (MOA1) and (MOB1), and a second effective zero-order plate (ZO2) which is constructed from two multiple order plates (MOA2) and (MOB2). An entered electromagnetic beam (EMBI) emerges as electromagnetic beam (EMBO) with a retardation entered between orthogonal components thereof with a Retardation vs. Wavelength such as demonstrated in FIGS. 15a-15e. FIGS. 9h and 9i are views looking into the left and right ends of the preferred Compensator Means (PC) as shown in FIG. 9g1, and show that the Fast Axes (FAA2) and (FAB2) of the second effective Zero-Order Waveplate (ZO2) are rotated away from zero or ninety degrees and are ideally oriented at forty-five degrees, with respect to the Fast Axes (FAA1) & (FAB1) of the first effective Zero-Order Waveplate (ZO1). (Note that the fast axis (FAA1) of the first effective Zero-Order Waveplate (ZO1) is shown as a dashed line in FIG. 9i, for reference). FIG. 9j demonstrates functional construction of another preferred compensator which is constructed from two per se. single plate Zero-Order Waveplates (MOA) and (MOB), which are typically made of materials such as mica or polymer. Note, it is to be understood that the space between retarder plates in FIGS. 9g1 and 9j can be reduced from that shown, even to the point where said retarder plates make contact with one another. Hence the presence of the spatial separation of the retarder plates shown in FIGS. 9g1 and 9j is not to be interpreted as indicating a required limitation. FIG. 9g2 shows three Zero Order Plates are contacted to one another instead of having space thereinbetween. Three element Compensators configured as suggested by FIGS. 9g1, 9g2 and 9j can comprise a "Psuedo Achromatic" which can provide Retardation vs. Wavelength characteristics such as those presented in FIG. 10g2. (See discussion of FIG. 10g2 later in this Specification).

(It is specifically to be understood that a compensator means system can be comprised of at least one Zero-Order waveplate and at least one effectively Zero-Order waveplate in combination, as well as combinations comprised of two actual Zero-Order waveplates or two effectively Zero-Order waveplates. And, a compensator can comprise more than two Zero-Order waveplate and/or effectively Zero-Order waveplates. FIGS. 9g1 and 9j, for instance, demonstrate in dashed lines the presence of additional Zero-Order waveplate and/or effectively Zero-Order waveplates. It is specifically noted that the dashed lines in FIG. 9g1 can represent a true single plate Zero-Order waveplate and the dashed lines in FIG. 9j an effectively Zero-Order waveplate. For instance, in FIG. 9j, the dashed lines can be an effective Zero-Order waveplate constructed from plates similar to (MOA1) and (MOB1). Also, the dashed lines in FIG. 9g1 can be interpreted represent a single Zero-Order waveplate similar to (MOA) in FIG. 9j, by assuming deletion of one dashed line. The Claims are to be understood in light of this disclosure).

A preferred disclosed invention embodiment comprises at least one of said at least one compensator means (C) (C') (C"), which is selected from the group consisting of:

comprised of at least two per se. zero-order waveplates (MOA) and (MOB), said per se. zero-order waveplates (MOA) and (MOB) having their respective fast axes rotated to a position offset from zero or ninety degrees with respect to one another, with a nominal value being forty-five degrees;

comprised of a combination of at least a first (ZO1) and a second (ZO2) effective zero-order wave plate, said first (ZO1) effective zero-order wave plate being comprised of two multiple order waveplates (MOA1) and (MOB1) which are combined with the fast axes thereof oriented at a nominal ninety degrees to one another, and said second (ZO2) effective zero-order wave plate being comprised of two multiple order waveplates (MOA2) and (MOB2) which are combined with the fast axes thereof oriented at a nominal ninety degrees to one another; the fast axes (FAA2) and (FAB2) of the multiple order waveplates (MOA2) and (MOB2) in said second effective zero-order wave plate (ZO2) being rotated to a position at a nominal forty-five degrees to the fast axes (FAA1) and (FAB1), respectively, of the multiple order waveplates (MOA1) and (MOB1) in said first effective zero-order waveplate (ZO1);

comprised of a combination of at least a first (ZO1) and a second (ZO2) effective zero-order wave plate, said first (ZO1) effective zero-order wave plate being comprised of two multiple order waveplates (MOA1) and (MOB1) which are combined with the fast axes thereof oriented at a nominal ninety degrees to one another, and said second (ZO2) effective zero-order wave plate being comprised of two multiple order waveplates (MOA2) and (MOB2) which are combined with the fast axes thereof oriented at a nominal ninety degrees to one another; the fast axes (FAA2) and (FAB2) of the multiple order waveplates (MOA2) and (MOB2) in said second effective zero-order wave plate (ZO2) being rotated to a position away from zero or ninety degrees with respect to the fast axes (FAA1) and (FAB1), respectively, of the multiple order waveplates (MOA1) and (MOB1) in said first effective zero-order waveplate (ZO1);

comprised of at least one zero-order waveplate, ((MOA) or (MOB)), and at least one effective zero-order waveplate, ((ZO2) or (ZO1) respectively), said effective zero-order wave plate, ((ZO2) or (ZO1)), being comprised of two multiple order waveplates which are combined with the fast axes thereof oriented at a nominal ninety degrees to one another, the fast axes of the multiple order waveplates in said effective zero-order wave plate, ((ZO2) or (ZO1)), being rotated to a position away from zero or ninety degrees with respect to the fast axis of the zero-order waveplate, ((MOA) or (MOB));

Now, and very importantly, even though the Invention disclosed in this Specification is a Rotating Compensator Material System Investigation System which is Spectroscopic, (ie. simultaneously operates on a number of Wavelengths in a Beam containing many Electromagnetic Wavelengths, over a range of, for instance, 190–1700 nanometers), a Compensator Means (C), (C'), (C") utilized therein can provide a Retardance which varies with Wavelength and still be usable. A Compensator Means (C), (C'), (C") does however, typically, have to be of a nature to allow passage of a Polychromatic Electromagnetic Beam therethrough without causing significant Attenuation, Deviation or Displacement in the Direction of Propagation thereof.

Particularly as regards Deviation and Displacment, if this is not the case, difficult to compensate complexities are caused in Detector Elements (DE's) containing Photo Array Detector System (DET) Detector Element Output Signals.

The reason a Spectroscopic Ellipsometer can operate with a Compensator Means (C), (C'), (C") that does not provide even close to a Constant Ninety (90) Degree Retardance over a range of Wavelengths, (which would constitute Ideal Characteristics), is that a Regression based Calibration Procedure utilized, (see the Disclosure of the Invention Section of this Specification), provides Wavelength dependent Compensation effecting values for Calibration Parameters as required in a developed Mathematical Model of the Rotating Compensator Material System Investigation System, (ie./eg. Rotating Compensator Spectroscopic Ellipsometer). As better described in the Disclosure of the Invention Section of this Disclosure, the Inventors develop a Calibration Parameter Containing Mathematical Model of the Rotating Compensator Material System Investigation System by, for instance, utilizing Matrix Representations for various System Components involved, then multiplies out the Matrices in an appropriate order to provide a Transfer Function. This applies for all Wavelengths monitored by a Detector Elements (DE's) containing Photo Array Detector System (DET) Detector Element (DE). Next, Data Set(s) are Experimentally obtained as a function of wavelength and typically as a function of various settings of the Polarizer Means (P) or Analyzer Means (A), (or both could be rotated to various positions), while a Compensator Means (C) rotates at, typically though not necessarily, Twenty (20) to Thirty (30) Hz. Other rotation speeds can be utilized and if two Compensator Means (C) (C') are present one or both can be caused to rotate, and if both are caused to rotate, as mentioned infra herein, they can be caused to rotate at the same, or different, speeds. (Note that Data Set(s) could also be achieved utilizing variation of Angle-Of-Incidence of a Beam of Polychromatic Radiation with respect to a Material System, (Sample), under investigation). Calibration Parameters in the Mathematical Model are then evaluated by, typically, Mean-Square-Error based Regression onto the Data Set(s). It is also possible to effectively find Calibration Parameter containing Mathematical Expressions for Coefficients of Mathematical Series, (eg. Fourier Series), which comprise the Mathematical Model Transfer Function, and calculate Numerical Values for the Coefficients from the Data Set(s), then effectively perform Regression of said Calibration Parameter containing Mathematical Expressions for Coefficients of Mathematical Series Transfer Function onto said Numerical Values for the Coefficients from the Data Set(s). It is emphsized that a single Two-Dimensional Data Set has been found sufficient to allow excellent Calibration results to be achieved. Said Two-Dimensional Data Set typically is Intensity vs. Wavelength, and Polarizer Means or Analyzer Means Azimuthal Rotation Angle i;o settings. In addition, said Two-Dimensional Data Set can be obtained from a Rotating Compensator Material System Investigation System oriented so that a Polychromatic Beam of Electromagnetic Radiation interacts with a Material System, (Sample), (ie. the "Sample Present" Mode—see FIGS. 1, 3, 4, and 5)), or such that said Polychromatic Beam of Electromagnetic Radiation passes through the Rotating Compensator Material system Investigation System without interacting with a Material System, (Sample), other than a Material System, (Sample), comprised of "Open Atmosphere", (ie. the Straight-Through" Mode—see FIG. 7).

The Rotating Compensator Material System Investigation System can also, of course, be Calibrated utilizing more than one Data Set and such a procedure is reported in U.S. Pat. No. 5,706,212, wherein a Rotating Compensator Material System Investigation System utilized in the Infra-red band of wavelengths, requires that two (2) Data Sets be present, (eg. selected with the Rotating Compensator Material System Investigation System oriented in a manner selected from the group: ("Straight-Through", "Material System, (Sample), Present", "Alternative Material System, (Sample), Present")). Both Data Sets are simultaneously utilized in a Regression Procedure to evaluate numerous Calibration Coefficients in a Mathematical Model which is described in the 212 Patent. The reason that only one (1) Data Set is can suffice to practice the described Calibration Procedure, is that the number of Calibration Parameters required by the Mathematical Model of the system, (which is not operated in the Infra-red range of wavelengths), is much fewer that the number of Calibration Parameters required by the Mathematical Model of the Rotating Compensator Material System Investigation System operated in the Infra-red range of wavelengths. The Rotating Compensator Material System Investigation System Mathematical Model typically involves as few as Five (5) Calibration Parameters, (where only one Compensator Means is present), in combination with simultaneous determination of a Material System, (Sample), PSI and DELTA. (It is noted that a straight-through mode essentially provides open atmosphere as a Material System, (Sample), and that the PSI and DELTA of open atmosphere are forty-five (45) degrees and zero (0.0) degrees, respectively). Said Five (5) Calibration Parameters are Azimuthal Orientation Angles for Polarizer Means (Ps), Analyzer Means (As), Compensator Means (Cs), and Compensator Retardance Parameters (P0) and (P1). Equations (45) and (46) serve as further demonstratration of this point. (Note that the (Ps), (Cs) and (As) Azimuthal Orientation Calibration Angles can be thought of as serving to align the Polarizer Means, Compensator Means and Analyzer Means Azimuths with a Material System, (Sample), Frame of Reference). Of course, if two Compensator Means are present then an additional Compensator Orientation Angle (Cs2) and Compensator Retardance Parameters (P0') and (P1') would also have to be evaluated. (It is noted that Retardation entered between orthogonal components of a Polarized Electromagnetic Beam, by a Compensator Means, is accounted for by a Matrix Component, and typically the r4 term of a Jones Matrix, but such is accounted for by Compensator Retardation Parameters (P0), (P1), (P0'), (P1') in the presently described Calibration Procedure).

A more complex calibration procedure provides for obtaining two (2) or three (3) data sets, and simultaneously regressing thereonto. A more complex calibration procedure can be beneficial where, for instance, a large wavelength range is being utilized and/or where multiple Angles of Incidence are to be utilized, and/or where it is desired to determine component "De-Polarization" effects and/or evaluate Mueller Matrix components. Where a multiple data set calibration procedure is practiced, a first data set is typically obtained utilizing a silicon substrate sample with two-hundred (200) to three-hundred (300) Angstroms, (eg. a nominal two-hundred-fifty (250) Angstroms), of silicon-dioxide on the surface thereof. A second data set can be obtained utilizing a sample which provides a large Ellipsometric PSI value, and an Ellipsometric DELTA value of between thirty (30) and one-hundred-fifty (150) degrees. Internal reflections from the hypotenuse of a right angle prism, either uncoated or coated with aluminum, or an optically thick metallic film, will provide such characteristics. FIGS. 1, 3, 4 and 5 demonstrate sample present data set gathering configurations of a Rotating Compensator Ellipsometer System. A third data set can be obtained with the ellipsometer system configured in a "straight-through" configuration, (see FIG. 7), wherein the effective sample PSI is forty-five (45) degrees and the effective sample DELTA is zero (0.0) degrees.

In general, the disclosed invention provides that at least one, at least one-dimensional, data set(s) be obtained utilizing a selection from the group consiting of:

all of said at least one, at least one-dimensional data set(s), are obtained utilizing a single material system (MS) placed on said stage (STG) for supporting a material system (MS), with which material system, (sample) (MS) the beam of electromagnetic radiation (PPCLB) is caused to interact;

at least one of said at least one, one-dimensional data set(s) is obtained utilizing one material system (sample) (MS) placed on said stage (STG) for supporting a material system, (sample) (MS), and at least one other of said at least one at least one-dimensional data set(s) is obtained utilizing another material system, (sample) (MS) placed on said stage (STG) for supporting a material system, (sample) (MS)), with which material system(s), (samples), (MS) the beam of electromagnetic radiation (PPCLB) is caused to interact; and at least one of said at least one-dimensional data set(s) is obtained with the spectroscopic rotating compensator material system investigation system oriented in a "straight-through" configuration wherein a polychromatic beam of electromagnetic radiation (FPCLB) produced by said source (LS) of a polychromatic beam of electromagnetic radiation, is caused to pass through said polarizer means (P), pass through said analyzer means (A), and interact with said dispersive optics (DO) such that a multiplicity of essentially single wavelengths are caused to simultaneously enter a corresponding multiplicity of detector elements (DE's) in said at least one detector system (DET), with said polychromatic beam of electromagnetic radiation (PPCLB) also being caused to pass through at least one compensator means (C) (C') (C") but without being caused to interact with any material system, (sample), (MS) placed on said stage (STG) for supporting a material system, (sample), (MS).

(Note: Prefered practrice is to obtain at least two, at least one dimensional data sets; or at least one multiple dimension data set upon which to regress).

Continuing, where a multiple data set calibration procedure is utilized to calibrate a rotating compensator material system investigating system for measuring Ellipsometric and Depolarization/Mueller Matrix values, it is also disclosed that it has been found desirable to normalize data to D.C. in some portions of the calibration, and to an A.C. derived term in other portions thereof. Equations such as those presented in EQS. 35b and 35c, (which are derived from Fourier Coefficients), serve as examples of A.C. data normalization parameters.

Preferred calibration procedure practise provides that data be normalized to A.C. where determining compensator means retardation (R), polarizer means azimuth (P) and compensator means fast axis azimuth (C) are fit, and that data be normalized to D.C where optical element Depolarization/Meuller Matrix values are fit. (For additional insight, see discussion in the Disclosure Of The Invention Section of this Specification regarding EQNS. 63–69, which define parameters 'b' and 'c').

Figure 3:
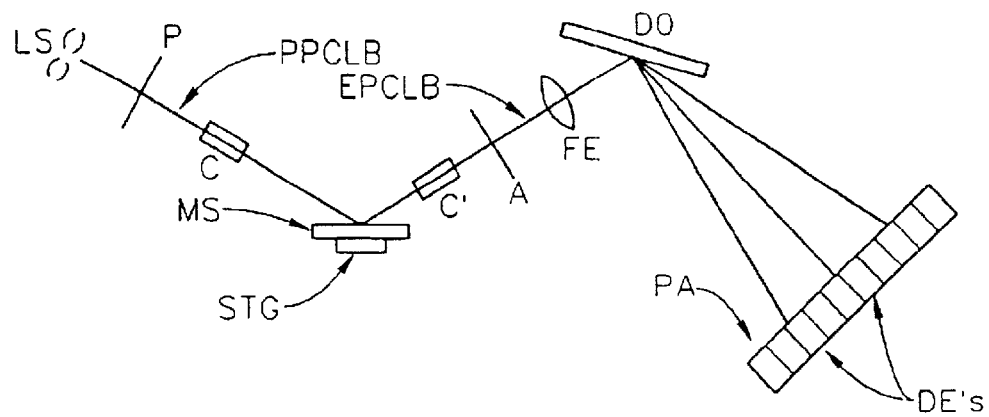
FIG. 3 shows a Reflectance Mode combination of components shown in FIGS. 1 and 2.

Now, it is to be understood that the system of the Spectroscopic Rotating Compensator Material System Investigation System is basically found in a combination of components shown in FIGS. 1 and 2, the basic result of said combination, for a Reflection Mode System, being shown in FIG. 3. That is, FIG. 3 shows a Spectroscopic Reflection Mode version of the Rotating Compensator Material System Investigation System shown in FIG. 1, with the FIG. 2 Detector Elements (DE's) containing Photo Array Detector System (DET) shown present directly after the Analyzer (A).

Figure 4:
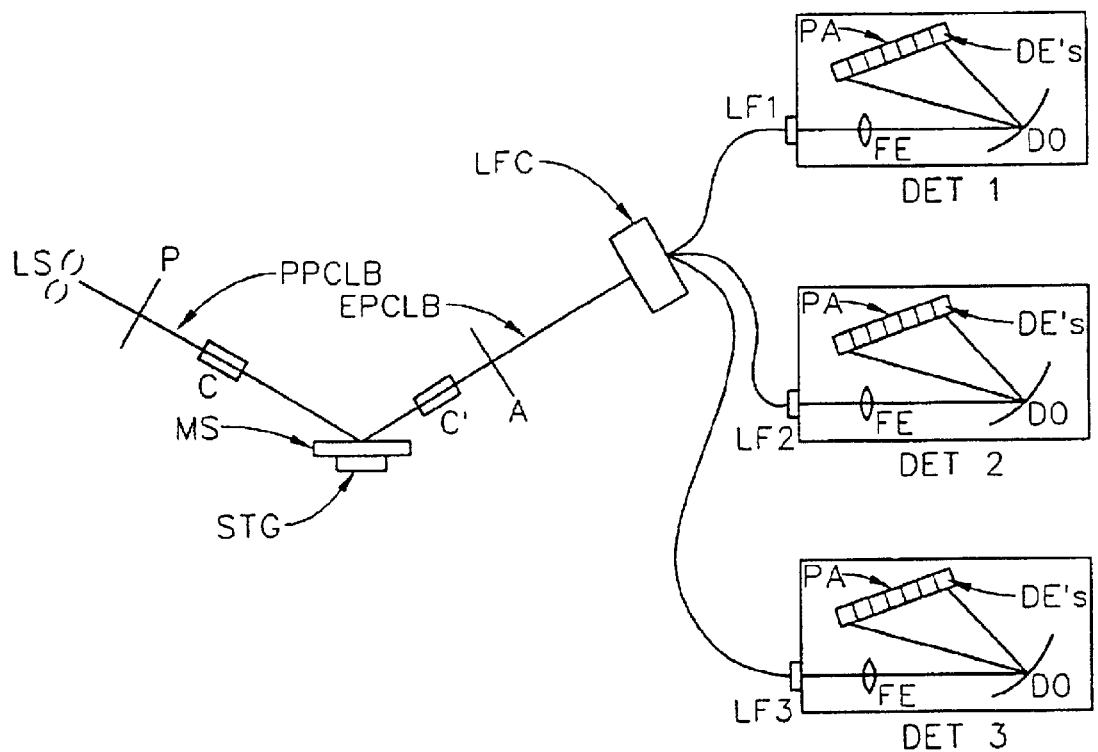
FIG. 4 shows a Reflectance Mode combination of components shown in FIGS. 1 and 2 in which three FIG. 2 Spectrographic Diode Array Spectrometer Systems are present and provided input via light fibers.

FIG. 4 shows a Reflection Mode System configuration in which three (3) Detectors (Det 1), (Det 2) and (Det 3) are fed input by Fiber Optics (LF1), (LF2) and (LF3) present in a Fiber Optic Bundle exiting Fiber Optic Connector (LFC). Said Fiber Optic Connector (LFC) receives a Polarized Electromagnetic Beam (EPCLB) exiting the Analyzer (A). (Note that a FIG. 9c at least Bifrucated Fiber Optic could be utilized). Said three (3) Detectors (Det 1), (Det 2) and (Det 3) can be previously disclosed Off-the-shelf Zeiss Diode Array Spectrometers, and can each comprise a Focusing Element (FE) in functional combination with a Dispersive Optics (DO) and a Diode Element (DE) containing Photo Array (PA).

Figure 5:
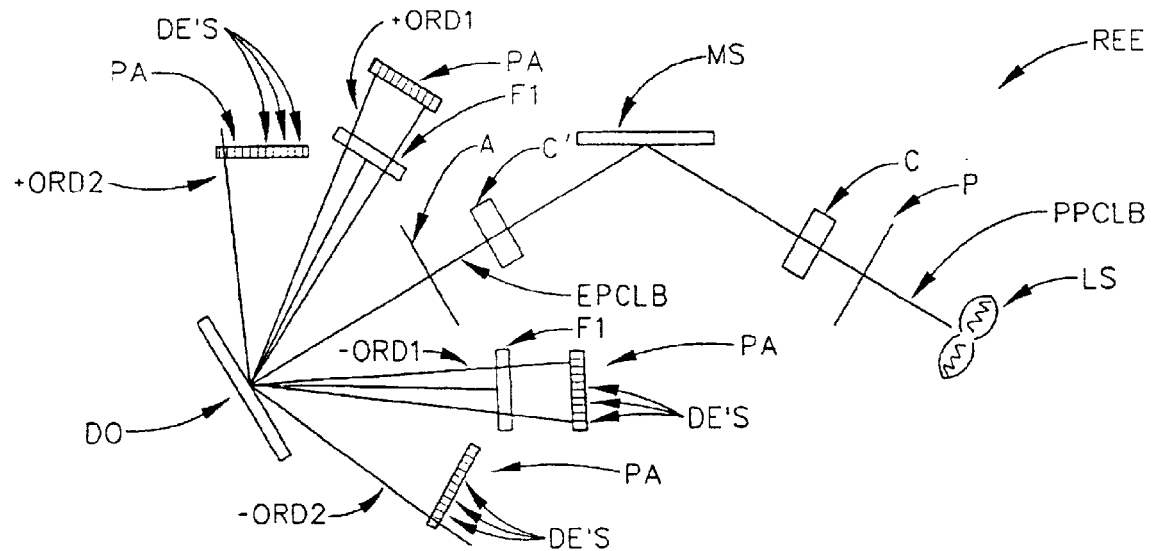
FIG. 5 shows a Reflectance Mode combination of components shown in FIGS. 1 and 2 in which Multiple Orders produced by a Dispersive Optics are intercepted by multiple Photo Arrays.

FIG. 5 shows that the described system can cause a Polychromatic Beam of Polarized Electromagnetic Radiation (PPCLB) to, after interaction with a Material System, (Sample), (MS), reflect therefrom. FIG. 5 shows that the Reflected Polarized Beam of Electromagnetic Radiation (EPCLB), is caused to impinge upon a Dispersive Optics (DO), (eg. a Diffraction Grating), such that a plurality of Orders (+ORD2, +ORD1, −ORD1 and −ORD2) are produced. Each said Order is comprised of a spectrum of Wavelengths, and FIG. 5 shows that Wavelengths in said Orders (+ORD2, +ORD1, −ORD1 and −ORD2) can be intercepted by Detector elements (DE's) in Photo Arrays (PA). Some embodiments of a Rotating Compensator Ellipsometer System utilize such a system. It is noted that the Dispersive Optics (DO) is typically rotatable so that the direction each Order of wavelengths generally proceeds from said Dispersive Optics (DO) is adjustable. Note that FIG. 5 also shows the presence of Filters (F1). It is noted that Wavelengths for adjacent Orders overlap, and said Filters (F1) allow a user to pass only desired Wavelengths, as well as reduce background radiation entry to Photo Arrays (PA's). Typically a Focusing Element is not present in a FIG. 5 embodiment.

It is also noted that Fiber Optics can be utilized to carry Polychromatic Electromagnetic Radiation from a Source thereof (LS) to the position of a Polarizer Means (P), or from the position of an Analyzer Means (A) to a Detector (DET) in FIGS. 1-5.

Analogically similar figures to those shown in FIGS. 3-5, but oriented for use in a Transmission Mode are not shown, but should be understood as within the scope of the implied by FIG. 1.

Continuing, the described invention achieves a Spectroscopic Rotating Compensator Material System Investigation System (eg. Spectroscopic Rotating Compensator Ellipsometer System), preferably utilizing an "Off-The-Shelf" compact Spectrometer Systems, and utilizing "Off-The-Shelf" Compensator Means Components which are not at all "ideal", as regards Achromaticity. To put this into perspective, it is noted that prior to about 1997, there was no known Spectroscopic Rotating Compensator Ellipsometer available in the market-place. It is believed that this is because it has previously been believed that to achieve such a System an Achromatic Rotating Compensator (RC) would be required. Such Compensators are not generally commercially available, hence, are expensive and reasonable approximations thereof typically must be individually fabricated.

(Note, as described in U.S. Pat. No. 5,706,212, a Dual-Rhomb Rotating Compensator (RC) which provides about seven (7%) percent variation in Retardation effected over a range of Wavelengths of approximately 2 to 14 microns, has been developed at the University of Nebraska. However, it is not clear that the identified University of Nebraska Dual-Rohmb Rotating Compensator (RC) would operate "Substantially Achromatically" outside the Identified range of wavelengths, but would rather, as is generally the case with all physically realizable Compensators, it would operate Psuedo-Achromatically over a larger wavelength range).

For general information, FIGS. 8a through 8d show various Dispersive Optics geometries. FIG. 8a shows a lined geometry diffraction grating (DGDO). The grating lines (GL) are essentially rectangular in cross-section with a spacing (a) therebetween. FIG. 8b shows a "Blazed" geometry Diffraction Grating Dispersive Optics (BDGDO). The Blazing Angle (BA) shifts reflected diffracted energy between "Orders" such into +ORD1 and −ORD1 from a typically useless ORD0 which projects perpendicularly back from the surface of said Dispersive Optics shown in FIG. 5. FIG. 8c shows a cross-sectional view of a Holographic Diffraction Grating Dispersion Optics (HDGDO) as is present in the Off-the-Shelf (Zeiss Diode Array Spectrometer systems identified infra herein. Said Zeiss Systems utilize a Holographic configuration in a concave shaped system). FIG. 8d shows a Prism Dispersive Optics (P1), with a Polarized Polychromatic Electromagnetic Beam (PPCCLB) entering Side (S1), and exiting Side (S2) and Side (S3) as Diffracted Beams in two "Orders" (ORDQ1) and (ORDP1) respectively. Note that a coating (OC) causes partial internal reflection of beam (PPCCBA) into beam (PPCLBB) to produce two "Orders". Any functional Diffraction effecting element can be utilized as a Dispersive Optics (DO) in the decribed invention.

As the invention can utilize Fiber Optics, certain geometries thereof are shown in FIGS. 9a through 9c. FIG. 9a shows a Fiber Optic which is essentially circular at the left side and which becomes of a "slit" shape at the right side. FIG. 9b shows a Fiber Optic which is essentially circular shaped along the entire length thereof, and which provides input to a "Slit" per se., (as is functionally utilized in the embodiment shown in FIG. 2). The effects achieved by the Fiber Optics in FIGS. 9a and 9b are similar. FIG. 9c shows a Trifrucated Fiber Optic which is essentially circular at the left side, which trifrucates and then is exemplified as becoming circular or a of a "slit" shape at the right side. Use of an effectively Trifrucated Fiber Optics is shown applied in FIG. 4. (Noted that Optical Fibers are utilized only as convenient means by which to transport electromagnetic radiation and not to modify polarization state. Also, it has been found that a beam splitter can be used instead of the bifrucated fibers. FIG. 9k, for instance, shows a diagram demonstrating use of beam splitters to direct an incident electromagnetic beam into two detectors, and FIG. 9l shows a "polka-dot" beam splitter which has been found to work well, (ie. Edmond Scientific part number 46-457 comprising a plate which is effectively half coated with a multiplicity of reflective regions such that approximately half of an incident electromagnetic beam reflects from, and half passes through). FIG. 9k also shows use of a beam splitter to provide a 10% of incident electromagnetic beam as an alignment beam directed into a four quadrant detector, and demonstrates optional use of reflective means, (eg. a simple mirror or perhaps beam folding optics as described in U.S. Pat. No. 5,969,818 to Johs et al.). The presence of focusing lenses (optional), is also demonstrated, as are the presense of, where functional, fiber optic means to guide electromagnetism to indicated detectors #1 and #2.

Method of Calibration Disclosed in U.S. Pat. No. 5,872,630

For insight, material presented in Parent U.S. Pat. No. 5,872,603 is again presented directly.

(Note, the Calibration Method is better described in the Disclosure of the Invention Section of this Specification. The following is to be considered as supplemental to the description provided in said Disclosure of the Invention Section).

In use, the Spectroscopic Rotating Compensator Material System Investigation System is modeled mathematically, with Calibration Parameters being included in said Mathematical Model. Said Calibration Parameters are evaluated by a regression based approach based upon Data Set(s) obtained at a multiplicity of Angles-of-Incidence, and/or Wavelengths and/or Polarizer or Analyzer Rotation Angle Settings etc. (Note that a relatively easily obtained Two Dimensional Data Set as a function of Wavelength, and either Polarizer or Analyzer Azimuthal Angle Setting, is greatly preferred and has been found to be sufficient). As mentioned infra herein, typically, Matrix representations of the Polarizer Means (P), Compensator Means (C), Analyzer Means (A), are utilized, with calibration parameters appearing in Matrix Components. Once evaluation of the Spectroscopic Rotating Compensator Ellipsometer System (RC) Calibration Parameters is effected, a Material System, (Sample), (MS) can be subjected to investigation thereby, with otherwise unexplained changes effected in a Beam of Polarized Electromagnetic Radiation (LB), present after interaction with a Material System, (Sample), (MS), being attributed to said Material System, (Sample), (MS). (It is also to be noted that PSI and DELTA associated with a Material System, (Sample), at a specific Angle-Of-Incidence can be simultaneously evaluated with Calibration Parameter values if a Data Set is obtained utilizing a Material System, (Sample), present mode and the Mathematical Model includes said Material System, (Sample), PSI and DELTA as functions of, for instance, Material System, (Sample), Thickness and/or Material System Surface Layer Thickness, and Angle of Incidence of the Electromagnetic Beam with respect to the Material System, (Sample), Surface, as Fit Parameters).

Figure 6:
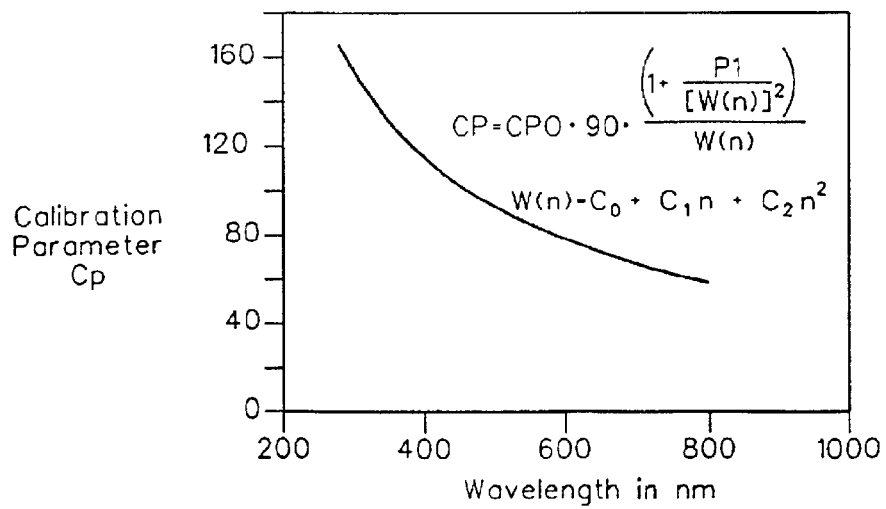
FIG. 6 demonstrates the Parameterization Approach to modeling Calibration Parameters which the disclosed invention utilizes in certain cases.
Figure 7:
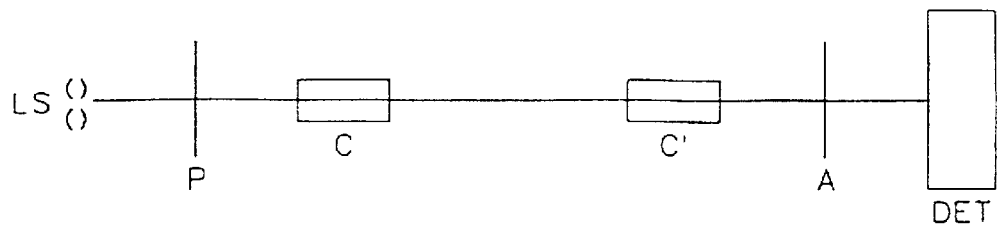
FIG. 7 demonstrates a "Straight-through" configuration of a Spectroscopic Rotating Compensator Material System Investigation System.

FIG. 6 demonstrates a Parameterization" approach to modeling Calibration Parameters in a Mathematical Model which was of more importance in the methodology of U.S. Pat. No. 5,872,630. Said example is retained herein as it is easy to understand. In that light, it must be understood that Calibration Parameters are often a function of Wavelength. For instance, the Retardation provided by a Compensator often varies inversely with wavelength. Where this is the case typical Mathematical Regression based evaluation of Calibration Parameters requires that a value for a Calibration Parameter be determined at each wavelength monitored. However, FIG. 6 shows that a plot of a Calibration Parameter vs. Wavelength can yield a locus which can be accurately modeled by a Mathematical Equation which requires only a few constants be known to allow calculation of the Calibration Parameter at a given Wavelength. For instance, FIG. 6 shows that a value for a Wavelength W(n) can be calculated knowing a Channel Number (n), (ie. Diode Element in an Array, such as shown in FIGS. 2-5), from which a signal is obtained, and values for three constants C0, C1 and C2. Knowing values for Parameters CP0 and P1 as well allows calculating a Calibration Parameter Value (CP) given a Diode Element Array Channel Number number (n). It can occur that (n) is two-hundred (200) or more and if a non-Parameterized approach to calibration is utilized, two-hundred (200) or more values for Calibration Parameter CP would have to be determined and stored. However, utilizing the Calibration Parameter Parameterization approach, it can be seen that a Regression procedure must return values for only Two (2) variables, (CP0 and P1). Also, if a Calibration Procedure were selected to include Angle-Of-Incidence (AOI) as a Data Set variable, it is known that where a Calibration Procedure utilizes a "Material System, (Sample), Present" configuration for acquiring data, that the PSI and DELTA values for the Material System, (Sample), will vary with said (AOI), and Material System, (Sample) and/or Surface Layer thereupon Thickness. (Note, said PSI and DELTA are equivalent to Calibration Parameters in a Regression procedure which serves to evaluate Calibration Parameters based upon Data obtained with a Material System present approach). A similar Parameterization approach could be applied to provide equations for calculating a PSI and a DELTA value given an (AOI) and/or, Material System, (Sample), or Surface Layer thereupon Thickness, each of said equations involving only a few variables which would have to be evaluated by a Regression procedure. (Note, the concept of "Parameterization" is often encountered in the modeling of Dielectric Functions, wherein one or more Lorentz Oscillator(s) is/are utilized. Lorentz Oscillator Structures require only a Magnitude, Energy and a Broadening Calibration Parameter be evaluated to be fully defined. Some peak regions of a Dielectric Function can be adequately modeled by said three evaluated Calibration Parameters, however, the peak and tail regions of a Lorentz Oscillator Structure are not mathematically separate and while a Lorentz Oscillator Structure might adequately define a peak region in a Dielectric Function plot, it is often inadequate in non-peak regions. This problem is the focus in U.S. Pat. No. 5,796,983 which teaches Finite Width Oscillator Structures comprised of Finite Order Polynomials and/or Finite Magnitude Essentially Zero Width Discontinuities as replacement for Lorentz Oscillator Structures). Where beneficial, Parameterization of Calibration Parameters can be utilized. That is, where a plot of a Calibration Parameter vs. a Data Set of Independent Variable demonstrates that Parameterization can be applied with benefit, the Parameterization of Calibration Parameter approach, with respect to some Data Set Independent Variable, can be applied.

The Spectroscopic Rotating Compensator Material System Investigation System then is comprised of Components as identified in FIGS. 1-5, and utility derives from the Calibration Method which utilizes Regression, including Parameterization of Calibration Parameter where desired and beneficial, to evaluate Calibration Parameters in a Mathematical Model of said Spectroscopic Rotating Compensator Material System Investigation System.

Application Results

Results of application of Global Regression Modes (GRM1), (GRM2) and (GRM3) are shown in U.S. Pat. No. 5,872,630.

The preferred approach involves practice of Global Regression Mode (GRM) 4, which, along with previously reported Global Regression Modes (GRM1), (GRM2) and (GRM3), is better described in the Disclosure Of The Invention Section of this Specification. (It is emphasized that presently preferred practice under Global Regression Mode (GRM) 4 involves parameterizing Material System, (System), PSI and DELTA values utilizing electromagnetic beam Angle Of Incidence and Material System, (Sample), and/or Surface Layer thereupon Thickness, as independent variables. See Eqn. 72 in the Disclosure of the Invention Section of this Specification for better mathematical insight).

FIG. 10a shows a plot of a compensator retardation characteristic which depends as (1/wavelength), (dashed line), as well as a compensator charactristic, (solid line). The important thing to note is that a selected range of wavelengths over which a retardation of between seventy-five (75) and one-hundred-thirty (130) degrees is developed, is much greater for said compensator means. As disclosed in the Disclosure of the Invention Section of this Specification, a spectroscopic rotating compensator material system investigation system typically comprises at least one compensator means which produces a retardance of, preferably, between seventy-five (75) and one-hundred-thirty (130) degrees over a range of wavelengths defined by a selection from the group consisting of:

a. between one-hundred-ninety (190) and seven-hundred-fifty (750) nanometers;

b. between two-hundred-forty-five (245) and nine-hundred (900) nanometers;

c. between three-hundred-eighty (380) and seventeen-hundred (1700) nanometers;

d. within a range of wavelengths defined by a maximum wavelength (MAXW) and a minimum wavelength (MINW) wherein the ratio of (MAXW)/(MINW) is at least one-and-eight-tenths (1.8).

Acceptable practice however, provides for the case wherein at least one of said at least one compensator(s) provides a retardation vs. wavelength characteristic retardation range of less than Ninety (90) degrees over a range of Thirty (30.0) and less than one-hundred-thirty-five (135) degrees, over a range of wavelengths specified from MINW to MAXW by a selection from the group consisting of:

a. MINW less than/equal to one-hundred-ninety (190) and MAXW greater than/equal to seventeen-hundred (17001) nanometers;

b. MINW less than/equal to two-hundred-twenty (220) and MAXW greater than/equal to one-thousand (1000) nanometers;

c. within a range of wavelengths defined by a maximum wavelength (MAXW) and a minimum wavelength (MINW) range where (MAXW)/(MINW) is at least four-and one-half (4.5).

(NOTE, the specified vales and ranges can not be achieved by single plates with (1/wavelength) retardation characteristics).

FIG. 10b shows calculated retardation vs. wavelength curves for two compensators which demonstrate (1/wavelength) retardation characerics, (long and short dashed lines), and the retardation curve, (solid line), of an assembly configuration as demonstrated in FIG. 9g1 which is arrived at by combining said two retarders with a 45 degree angle between the fast axes thereof.

FIG. 10c shows a re-scaled plot of the solid line curve shown in FIG. 10b.

FIGS. 10d and 10e show results calculated for a compensator means as demonstrated in FIG. 9g1, wherein one waveplate is selected at 266 NM and the other at 633 NM., and wherein the fast axes are oriented at 45 degrees with respect to one another. The wavelength range is from 190 to 730 NM, (ie. deep UV to Visable). FIG. 10d shows the calculated effective fast axis orientation of a two plate compensator means and FIG. 10e shows the calculated effective rotary power. Also, as discussed in the Jones paper identified in the Background Section of this Specification, an arbitrary sequence of retarder elements can be mathematically represented by a single compensator means with "effective" retardance, fast axis and rotary power.

FIGS. 10f and 10g1 show that changing waveplate selection for a FIG. 9g1 compensator means configuration, and the angle between fast axes of the compesator means members thereof, provides alternative retardation plots over various wavelength ranges. FIG. 10f provides results for wavelengths between 245 and 850 NM, when waveplate selection involves 266 NM and 780 NM, and that angle between the fast axes is 50 degrees. FIG. 10g1 provides reesults between 380 and 1700 NM, for selection of waveplates at 532 NM and 1550 NM, and an angle between fast axes of 50 degrees. FIGS. 10f and 10g1 are included to show that compensator means design can be easily carried out, with the end result that retardations of between 75 and 130 degrees can be achieved over various wavelength ranges.

FIG. 10g2 shows retardation vs. wavelength for a three (3) Zero-Order plate element compensator as can be realized such as suggested by FIGS. 9g1, 9g2 and 9j. Note the retardation varies between about 47 degrees and 130 degrees over a wavelength range of 190 to 1700 nm. Said three (3) element compensator comprises a 422 nm quartz Zero Order waveplate sandwiched by two 6.33. nm quartz Zero Order waveplates. The azimuth of the 422 nm Zero Order waveplate is oriented +41 degrees with respect to the azimuth of the first 633 nm Zero Order plate, and the azimuth of the second 633 nm Zero Order Waveplate is oriented −33 degrees with respect to the azimuth of the first 633 nm Zero Order Waveplate. This compensator design then provides a retardance characteristic which varies over a range less than 90 degrees over a wavelength range, which retardance does not exceed 130 degrees. Note specifically that the retardation vs. wavelength characteristic retardation range is less than Ninety (90) degrees over a range bounded by Thirty (30.0) to less than one-hundred-thirty-five (135) degrees, over a range of wavelengths specified from a MINW of one-hundred-ninety (190), and a MAXW of seventeen-hundred (1700) nanometers, hence, even though the range of its retardation is between about 47 and 130 degrees, it is covered by Claim language which recited boundaries of 30 and less than 135 degrees.

FIGS. 10h-10o show various experimentally obtained plots utilizing a J.A. Woollam CO. Inc. Rotating Compensator Ellipsometer System, (ie. the "M-2000", Registered Trademark). Curves in FIGS. 10h-10j were extracted using A.C. Normalization while curves in FIGS. 10k-10L were extracted using D.C. Normalization. In particular, FIG. 10h shows azimuthal Compensator Means Retardance as a function of Wavelength. Note that, except for the presence of harmonic "wiggles", (which are due to the imperfect alignment of the "effective" zero-order waveplate), the curve closely corresponds to the calculated curve in FIG. 10c. FIG. 10i shows Effective Input Polarizer Means Azimuthal Angle, (including the rotary effect of the Compensator). FIG. 10j shows the effective Fast Axis of the Compensator Means Azimuthal Orientation. FIG. 10k shows Depolariztion factor 'c' and FIG. 10L shows Depolarization factor 'b', as defined in the D.C. term in Eqs. 67. (Note in particular the excellent agreement between polts in FIGS. 110c-10e, and FIGS. 10h-10j).

FIGS. 10m-10o show familiar PSI and DELTA Curves obtained with a Rotating Compensator Ellipsometer System, for Silicon Substrates on, respectively, 1 Micron, 250 Angstroms and 25 Angstroms of $SiO_2$ on the surface thereof.

It is noted that the described invention easily avoids the limitation inherrent in the Patent to Aspnes, U.S. Pat. No. 5,877,589, which Patent was identified in the Background Section of this Disclosure, while providing excellent materials system investigation results. Further, the described invention also avoids utilization of "substantially-non-achromatic" compensator means with at least a ninety (90) degree range of retardance variance of an applicable wavelength range, hence avoids the limitations in the Aspnes et al. U.S. Pat. Nos. 6,320,657 B1 and 6,134,012, respectively, again while providing excellent materials system investigation results.

It is noted that the terminology Spectroscopic Rotating Compensator Material System Investigation System is to be interpreted sufficiently broadly to include Ellipsometers and Polarimeters with integrated electromagnetic radiation sources, and the like systems. In the Claims the terminology Spectroscopic Ellipsometer is utilized as being generic, with this in mind.

As well, it should be understood that a Mathematical Model developed to represent a Spectroscopic Rotating Compensator Material System Investigation System, (ie. Spectroscopic Ellipsometer), can be expressed as explicit equations for Intensity Transfer Function, or as equations for Coefficients of Terms which comprise such as a Transfer Function. However, in the context of performing Regression based evaluation of Calibration Parameters, it is to be understood that a Mathematical Model can "Effectively" provide such equations. That is, a computer program need not calculate a Transfer Function per se. to utilize mathematical relationships inherent therewithin. The terminology "Mathematical Model" and "Transfer Function, and "Coefficients of Terms" are to be interpreted sufficiently broadly so as to include the case where acutal explicit equations therefore are not per se. generated, but where mathematical relationships inherrant "Mathematical Model" and "Transfer Function, and "Coefficients of Terms" are utilized by a Regression based Calibration Parameter evaluation procedure. For instance, Numerical Equivalents to Specific Analytical Functions can be present and utilized in a Computer and be within the scope of the identified terminology, even though specific Analytical Equations are not per se., but only effectually, produced.

It is also to be appreciated that no other Spectroscopic Rotating Compensator Ellipsometer SYSTEM is known which comprises at once:

1. at least one Pseudo-Achromatic Characteristic Rotating Compensator Means (RC);
2. a Dispersive optics (DO); and
3. a Detector Elements (DE's) containing Detector System (DET) which comprises a Photo Array (PA); such that in use a Multiplicity of Material System, (Sample), (MS) Investigation Wavelengths in a Polychromatic Beam of Electromagnetic Wavelengths are simultaneously Monitored.

In particular, other than as reported in Parent U.S. Pat. No. 5,872,630, no known Spectroscopic Rotating Compensator Material System Investigation System utilizes a, (possibly Calibration Parameter Parameterization aided), Mathematical Regression based METHOD approach to Evaluation of Calibration Parameters in a Mathematical Model of such a Spectroscopic Rotating Compensator Material System Investigation System, such that application thereof allows compensating the Psuedo-Achromatic, and other non-Ideal, aspects of a substantially Achromatic or Psuedo-Achromatic Rotating Compensator Means.

It is emphasized that the described invention is considered to be particularly impressive as it is relatively easily constructed utilizing commercially available "Off-The-Shelf"

Diode Array Spectrometer Systems, and non-ideal Compensators. The described invention conveniently provides, in a commercially realizable format, that which was thought to be, prior thereto and the version thereof presented in the Parent U.S. Pat. No. 5,872,630, essentially impossibly to provide in other than a prohibitively expensive, (and perhaps difficult to calibrate and utilize), single unit format.

It is to be understood that a Photo Array can be comprised of Diode-Elements, Charge-Coupled-Devices, Bucket-Brigade-Devices and equivalents.

It is also noted that Polychromatic Electromagnetic Bean Source can be comprised of a combined plurality/multiplicity of Laser Sources, and that Polychromatic Electromagnetic Beam Source can include an effective Polarizer therewithin, thereby eliminating the need for a separate Polarizer Means. Such cases are to be considered within the scope of the Claims with the effective Polarizer Means considered as the recited Polarizer Means.

It is further to be understood that the terminology "zero-order" is typically utilized herein to mean a single plate retarder/compensator, while the terminology "effective zero-order" is typically utilized herein to mean a zero-order retarder/compensator which is constructed from more that a single plate.

It is also to be understood that while there may be technical definitions in the literature which provide different meanings therefore, the terms "waveplate", "retarder" and "compensator" are utilized substantially interchangably in this specification.

It is also to be understood that the terminology "Straight-through" configuration provides as an effective material system, ambient atmosphere.

Finally, it is again noted that Zeiss Diode Array Spectrometer Systems identified by manufacturer numbers, in the group: (MMS1 (300–1150 nm); UV/VIS MMS (190–730 nm); UV MMS (190–400 nm); AND IR MMS (900–2400 nm)); as well as Hamamatsu CCD Array Detectors, (Series S7030/S7031), with a quantum efficiency of 40% or more hav been successfully utilized in the described invention system. The Hamamatsu CCD array, combined with a diffraction means, is presently preferred.

It is specifically to be understood that the terminology "Compensator means" is to be interpreted sufficiently broadly to include one or more than one compensator(s), and that that for the purposes of this Specification and Claim interpretation, that as applied to a Compensator or Compensator Means:

"Substantially Achromatic" means that over a specified range of wavelengths the Retardation varies from just above 0.0 up to about thirty (30) degrees; and "Pseudo-Achromatic" means that over a specified range of wavelengths the Retardation varies less than Ninety (90) degrees, (ie. the maximum minus minimum retardation is less than 90 degrees), over a range of retardations with a mimimum retardation of preferably at least Thirty (30) degrees and a maximum retardation of less than One-Hundred-Thirty-Five (135) Degrees.

"Non-achromatic" is to be interpreted to mean that retardance entered to a beam of electromagnetic radiation by a retarder/compensator at one wavelength is different from that entered at a different wavelength. For instance, the Aspnes et al. 012, 787 and 657 Patents suggest that if "an effective phase retardation value is induced covering at least from 90 decrees to 180 degrees", (012 Patent), over a range of wavelengths of 200–800 nm, such is definitive of a "Substantially-Non- Achromatic" compensator means.

The compensator means of the presently disclosed invention can be termed "Substantially Achromatic", but are more properly termed "Pseudo-achromatic" in that they do not produce uniform retardation at all wavelengths, but produce retardation which is far more uniform than, for instance, waveplates that provides retardance which varies proportional to (1/wavelength).

It is also to be understood that the terminology "Spectroscopic Ellipsometer" utilized in the Claims is referring to the system described in the Detailed Description generally as a "Spectroscopic Rotating Compensator Material System Investigation System". The alternative language is utilized to provide easy Claim language comparison to the Claim language in the Aspnes et al. U.S. Pat. Nos. 6,320,657 B1, 6,134,012, 5,973,787 and 5,877,859. This is done for the purpose of avoiding confusion as to what the J.A. Woollam Co. Inc. and the Thermawave Inc. Patents respectively protect.

Having hereby disclosed the subject matter of this invention, it should be, obvious that many modifications, substitutions and variations of the present Invention are possible in light of the teachings. It is therefore to be understood that the present invention can be practiced other than as specifically described, and should be limited in breadth and scope only by the Claims.

We claim:

1. A spectroscopic ellipsometer for evaluating a sample comprising:

a broadband light source generating a beam having wavelengths extending over a range of at least 200 to 800 nm;

a polarizer disposed in the path of the light beam;

a compensator disposed in the path of the light beam, said compensator for inducing phase retardations in the polarization state of the light beam, said compensator having characteristics other than substantially-non-achromatic so that the amount of phase retardations varies with wavelength, over a range of wavelengths, less than is the case were a substantially-non-achromatic compensator utilized, said compensator being rotated at an angular frequency of $\omega$;

an analyzer that interacts with the light beam after the beam interacts with the sample and with the compensator;

a detector that measures the Intensity of the light beam after the interaction with the analyzer at a plurality of wavelengths across the wavelength range of at least 200 to 800 nm;

said detector generating a time varying intensity output signal simultaneously comprising $2\omega$ and $4\omega$ component signals; and optionally a processor for evaluating the sample based on simultaneous use of the intensity output signal $2\omega$ and $4\omega$ components.

2. A spectroscopic ellipsometer as in claim 1, in which applies at least one selection from the group consisting of:

the compensator fast axis azimuthal angle varies with wavelength;

the compensator range of retardations over the range of wavelengths does not include 180 degrees; and the compensator provides retardance which varies by less than ninety (90) degrees (max–min) over a range of wavelengths, said retardance being within a range of retardations bounded by (30.0) to less than (135) degrees.

3. A spectroscopic ellipsometer for evaluating a sample comprising:
- a broadband light source generating a beam having wavelengths extending over a range of at least 200 to 800 nm;
- a polarizer disposed in the path of the light beam;
- a compensator disposed in the path of the light beam, said compensator for inducing phase retardations in the polarization state of the light beam, said compensator having characteristics selected from the group consisting of:
  - being substantially-achromatic; and
  - being pseudo-achromatic;
- said compensator being rotated at an angular frequency of ω;
- an analyzer that interacts with the light beam after the beam interacts with the sample and with the compensator;
- a detector that measures the intensity of the light beam after the interaction with the analyzer at a plurality of wavelengths across the wavelength range of at least 200 to 800 nm;
- said detector generating a time varying intensity output signal simultaneously comprising 2ω and 4ω component signals; and
- optionally a processor for evaluating the sample based on simultaneous use of the intensity output signal 2ω and 4ω components.

4. A spectroscopic ellipsometer as in claim 3, in which applies at least one selection from the group consisting of:
- the compensator fast axis azimuthal angle varies with wavelength;
- the compensator range of retardations over the range of wavelengths does not include 180 degrees; and
- the compensator provides retardance which varies by less than ninety (90) degrees (max–min) over a range of wavelengths, said retardance being within a range of
- detector means that measure the intensity of the beam after the interaction with the analyzer means at a plurality of wavelengths across the wavelength range of at least 200 to 800 nm;
- said detector means generating a time varying intensity signal simultaneously comprising 2ω and 4ω component signals, said 2ω and 4ω signals being simultaneously present at all wavelengths measured unless the 2ω signal is forced to 0.0 by a sample presenting with an ellipsometric DELTA of 0.0 as opposed to being caused to be 0.0 by said compensator means; and
- optionally a processor for evaluating the sample based on simultaneous use of the intensity output signal 2ω and 4ω components.

5. A spectroscopic ellipsometer for evaluating a sample comprising:
- broadband electromagnetic radiation source means generating a beam having wavelengths extending over a range of at least 200 to 800 nm;
- polarizer means disposed in the path of said beam;
- compensator means disposed in the path of the beam, said compensator for inducing phase retardations in the polarization state of the light beam, said compensator means being:
  - pseudo-achromatic;
- in that the amount of phase retardation varies more with wavelength, over a range of wavelengths, than is the case if a substantially-achromatic compensator is utilized; but in that the amount of phase retardation varies less with wavelength, over said range of wavelengths, than is the case if a substantially-non-achromatic compensator is utilized, said compensator means being rotated at an angular frequency of ω;
- analyzer means that interact with the beam after the beam interacts with the sample and the compensator means;
- detector means that measure the intensity of the beam after the interaction with the analyzer means at a plurality of wavelengths across the wavelength range of at least 200 to 800 nm;
- said detector means generating a time varying intensity signal simultaneously comprising 2ω and 4ω component signals, said 2ω and 4ω signals being simultaneously present at all wavelengths measured unless the 2ω signal is forced to 0.0 by a sample presenting with an ellipsometric DELTA of 0.0 as opposed to being caused to be 0.0 by said compensator means; and
- optionally a processor for evaluating the sample based on simultaneous use of the intensity output signal 2ω and 4ω components.

6. A spectroscopic ellipsometer as in claim 5, in which applies at least one selection from the group consisting of:
- the compensator fast axis azimuthal angle varies with wavelength;
- the compensator means range of retardations over the range of wavelengths does not include 180 degrees; and
- the compensator provides retardance which varies by less than ninety (90) degrees (max–min) over a range of wavelengths, said retardance being within a range of retardations bounded by (30.0) to less than (135) degrees.

7. A spectroscopic ellispometer as in claim 5 in which a selection is made from the group consisting of:
- the compensator provides retardance which varies by less than ninety (90) degrees (max–min) over a range of wavelengths, said retardance being within a range of retardations bounded by (30.0) to less than (135) degrees over a range of wavelengths defined by a selection from the group consisting of:
  - a. minimum wavelength is less than one-hundred-ninety (190) and maximum wavelength greater than seventeen-hundred (1700) nanometers;
  - b. minimum wavelength is less than two-hundred-twenty (220) and maximum wavelength MAXW greater than one-thousand (1000) nanometers;
  - c. within a range of wavelengths defined by a maximum wavelength (MAXW) and a minimum wavelength (MINW) range where (MAXW)/(MINW) is at least four-and-one-half (4.5); and
- the compensator means provides retardance of between seventy-five (75) and one-hundred-thirty (130) degrees over a range of wavelengths defined by a selection from the group consisting of:
  - d. between one-hundred-ninety (190) and seven-hundred-fifty (750) nanometers;
  - e. between two-hundred-forty-five (245) and nine-hundred (900) nanometers;
  - f. between three-hundred-eighty (380) and seventeen-hundred (1700) nanometers;
  - g. within a range of wavelengths defined by a maximum wavelength (MAXW) and a minimum wavelength (MINW) wherein the ratio of (MAXW)/(MINW) is at least one-and-eight-tenths (1.8).

8. A spectroscopic ellipsometer as in claim 5 in which the compensator means is caused to rotate by a pulse driven stepper-motor, the position of said rotating compensator being commonly synchronized to corresponding output from said detector.

9. A spectroscopic ellipsometer as in claim 5 in which compensator means is comprised of a type selected from the group consisting of:
Berek-type with optical axis essentially perependicular to a surface thereof;
non-Berek-type with an optical axis essentially parallel to a surface thereof;
zero-order wave plate;
zero-order waveplate constructed from two multiple order waveplates;
a sequential plurality of zero-order waveplates, each constructed each from a plurality of multiple order waveplates;
rhomb;
polymer;
achromatic crystal; and
pseudo-achromatic.

10. A spectroscopic ellispometer system as in claim 5, in which said detector which measures the intensity of the beam after the interaction with the analyzer at a plurality of wavelengths across the wavelength range of at least 200 to 800 nm, receives input via a dispersive optics.

11. A spectroscopic ellipsometer system as in claim 10 in which said dispersive optice is selected from the group consisting of:
a prism; and
a diffraction grating which is selected from the group consisting of:
a "lined";
a "blazed"; and
a "holographic" geometry;
said lined geometry consisting essentially of symetrical alternating lines with depressions therebetween, and said blazed geometry consisting of alternating ramp shaped lines with depressions therebetween, and said holographic geometry consisting of continuous cosine shaped lines and depressions.

12. A spectroscopic ellipsometer system as in claim 5, wherein sample reflectance is determined from the detector output signal without application of normalizion to a component selected from the group consisting of:
D.C.; and
A.C.

13. A spectroscopic ellipsometer system as in claim 5 which further comprises a focusing element, for directing the beam onto a sample, disposed in the path of said beam.

14. A spectroscopic ellipsometer system as in claim 5 in which the compensator means comprises a plurality of compensators present at at least one location selected from the group consisting of:
before; and
after;
a sample, and a selection is made from the group consisting of:
all said compensators are caused to rotate in use; and
at least one of said compensators is not caused to rotate in use.

15. A spectroscopic ellipsometer system as in claim 5 in which a fiber optic is present at at least one location selected from the group consisting of:
between said broadband electromagnetic radiation source and the polarizer means; and
between said analyzer means, and a dispersive optics.

16. A spectroscopic in claim 15 in which an electromagnetic beam directing means is present after the analyzer, said electromagnetic beam directing means being selected from the group consisting of:
fiber optics, said fiber optics becoming at least bifrucated (LF1) (LF2) (LF3) thereby providing a plurality of fiber optic bundles, at least two of which plurality of at least two bifrucated fiber optic bundles provide input to separate detector systems (DET1) (DET2) (DET3), each of said separate detector systems comprising a dispersion optics and a multiplicity of detector elements; and
beam splitter means which passes approximately half a beam incident from said analyzer into one detector, and reflects the remainder of said incident beam into a second detector.

17. A spectroscopic ellipsometer system as in claim 5 which is characterized by a mathematical model comprising calibration parameters, at least one of which is a member of the group consisting of:
effective polarizer means azimuthal angle orientation;
present sample PSI ($\Psi$), as a function of angle of incidence and a thickness;
present sample DELTA ($\Omega$), as a function of angle of incidence and a thickness;
compensator means azimuthal angle orientation;
matrix components of said compensator means;
analyzer means azimuthal angle orientation; and
detector element image persistence ($x_n$) and read-out ($p_n$) nonidealities;
which mathematical model is effectively a transfer function which enables calculation of electromagnetic beam magnitude as a function of wavelength detected by a detector element, given magnitude as a function of wavelength provided by said broadband electromagnetic radiation source; said calibration parameter(s) selected from the group consisting of:
effective polarizer means azimuthal angle orientation;
present sample PSI ($\Psi$), as a function of angle of incidence and a thickness;
present sample DELTA ($\Delta$), as a function of angle of incidence and a thickness;
compensator means azimuthal angle orientation;
matrix components of said compensator means;
analyzer means azimuthal angle orientation; and
detector element image persistance ($x_n$) and read-out ($p_n$) nonidealities;
being, in use, evaluated by performance of a mathematical regression of said mathematical model onto at least one, multi-dimensional data set(s), said at least one multi-dimensional data set(s) being magnitude values vs. wavelength and at least one parameter selected from the group consisting of:
angle-of-incidence of said polychromatic beam of electromagnetic radiation with respect to a present sample; and
effective or actual azimuthal angle rotation of one element selected from the group consisting of:
said polarizer means; and
said analyzer means;
obtained over time, while compensator means is caused to continuously rotate;
said at least one, multi-dimensional, data set(s) each being normalized to a selection from the group consisting of:

a data set D.C. component;
a data set A.C. component;
a parameter derived from a combinations of a data set D.C. component and a data set A.C. component;
said mathematical model optionally further comprising a reflectance parameter calculated from at least one selection from the group consisting of:
un-normalized A.C.; and
un-normalized D.C.; components.

18. A spectroscopic ellipsometer as in claim 5 in which the compensator means is a selection from the group consisting of:

comprised of a combination of at least two zero-order waveplates (MOA) and (MOB), said zero-order waveplates (MOA) and (MOB) having their respective fast axes rotated to a position offset from zero or ninety degrees with respect to one another;

comprised of a combination of at least a first (ZO1) and a second (ZO2) effective zero-order wave plate, said first (ZO1) effective zero-order wave plate being comprised of two multiple order waveplates (MOA1) and (MOB1) which are combined with the fast axes thereof oriented at a nominal ninety degrees to one another, and said second (ZO2) effective zero-order wave plate being comprised of two multiple order waveplates (MOA2) and (MOB2) which are combined with the fast axes thereof oriented at a nominal ninety degrees to one another; the fast axes (FAA2) and (FAB2) of the multiple order waveplates (MOA2) and (MOB2) in said second effective zero-order wave plate (ZO2) being rotated to a position at a nominal forty-five degrees to the fast axes (FAB1) and (FAB1), respectively, of the multiple order waveplates (MOA1) and (MOB1) in said first effective zero-order waveplate (ZO1);

comprised of a combination of at least a first (ZO1) and a second (ZO2) effective zero-order wave plate, said first (ZO1) effective zero-order wave plate being comprised of two multiple order waveplates (MOA1) and (MOB1) which are combined with the fast axes thereof oriented at a nominal ninety degrees to one another, and said second (ZO2) effective zero-order wave plate being comprised of two multiple order waveplates (MOA2) and (MOB2) which are combined with the fast axes thereof oriented at a nominal ninety degrees to one another; the fast axes (FAA2) and (FAB2) of the multiple order waveplates (MOA2) and (MOB2) in said second effective zero-order wave plate (ZO2) being rotated to a position away from zero or ninety degrees with respect to the fast axes (FAA1) and (FAB1), respectively, of the multiple order waveplates (MOA1) and (MOB1) in said first effective zero-order waveplate (ZO1); and comprised of a combination of at least one zero-order waveplate, (MOA or MOB), and at least one effective zero-order waveplate, (ZO2 or ZO1 respectively), said effective zero-order wave plate being comprised of two multiple order waveplates which are combined with the fast axes thereof oriented at a nominal ninety degrees to one another, the fast axes of the multiple order waveplates in said effective zero-order wave plate being rotated to a position away from zero or ninety degrees with respect to the fast axis of the zero-order waveplate.

19. A method of calibrating a spectroscopic ellipsometer system comprising, in any functional order the steps of:
a. providing a spectroscopic ellipsometer for evaluating a sample comprising:

broadband electromagnetic radiation source means generating a beam having a wavelength extending over a range of at least 200 to 800 nm;
polarizer means disposed in the path of said beam;
compensator means disposed in the path of the beam, said compensator for inducing phase retardations in the polarization state of the light beam, said compensator means having characteristics other than substantially-non-achromatic, said compensator means being rotated at an angular frequency of $\omega$;
analyzer means that interacts with the beam after the beam interacts with the sample and the compensator means;
detector means that measure the intensity of the beam after the interaction with the analyzer means at a plurality of wavelengths across the wavelength range of at least 200 to 800 nm;
said detector means generating a time varying intensity output signal simultaneously comprising $2\omega$ and $4\omega$ component signals, said $2\omega$ and $4\omega$ component signals being simultaneously present at all wavelengths measured unless the $2\omega$ component signal is force to 0.0 by a sample presenting with an ellipsometric DELTA of 0.0 as opposed to being caused to be 0.0 by said compensator means;

b. developing a mathematical model of said spectroscopic ellipsometer which comprises as calibration parameter (s) at least one selection from the group consisting of:
effective polarizer means azimuthal angle orientation;
present sample PSI ($\Psi$), as a function of angle of incidence and a thickness;
present sample DELTA ($\Delta$) as a function of angle of incidence and a thickness;
retardations of said compensator means as a function of wavelength;
compensator means azimuthal angle orientation(s);
matrix components of said compensator means; and
analyzer means azimuthal angle orientation;
which mathematical model is effectively a transfer function which enables calculation of electromagnetic beam magnitude as a function of wavelength detected by a detector means element, given magnitude as a function of wavelength provided by said broadband electromagnetic radiation source means;

c. causing a polychromatic beam of electromagnetic radiation, produced by said broadband electromagnetic radiation source means, to pass through said polarizer means, interact with a sample caused to be in the path thereof, pass through said analyzer means, and enter detector element in said detector means, said polychromatic beam of electromagnetic radiation also being caused to pass through said compensator means;

d. obtaining at least one, multi-dimensional, data set(s) of magnitude values vs. wavelength and a parameter selected from the group consisting of:
angle-of-incidence of said polychromatic beam of electromagnetic radiation with respect to a present sample; and
effective or actual azimuthal angle rotation of one element selected from the group consisting of:
said polarizer means; and
said analyzer means;
over time, while said compensator means is caused to continuously rotate;
said at least one multi-dimensional, data set(s) being obtained utilizing a selection from the group consiting of:

all of said at least one multi-dimensional data set(s), being obtained utilizing a single sample;

at least one of said at least one multi-dimensional data set(s), being obtained utilizing one sample, with another of said at least one multi-dimensional data set(s), being obtained utilizing another sample; and at least one of said at least one multi-dimensional data set(s) being obtained with the spectroscopic ellipsometer system oriented in a "straight-through" configuration wherein a polychromatic beam of electromagnetic radiation is caused to pass through said polarizer means, pass through said analyzer means, and enter detector elements in said at least one detector system, with said polychromatic beam of electromagnetic radiation also being caused to pass through said compensator means but without being caused to interact with any sample other than open ambient atmosphere;

e1. optionally calculating reflectance from at least one selection from the group consisting of:
obtained A.C.; and
obtained D.C.;
data without peforming any normalization thereupon;

e2. normalizing data in each said at least two, at least one-dimensional, data set(s) with respect to a selection from the group consisting of:
a data set D.C. component;
a data set A.C. component;
a parameter derived from a combinations of a data set D.C. component and a data set A.C. component;

f. performing a mathematical regression of said mathematical model onto said normalized at least one, multi-dimensional, data set(s) and optionally said reflectance, thereby evaluating calibration parameters in said mathematical model;

said regression based calibration procedure serving to evaluate parameters in said said mathematical model for at least one selection from the group consisting of:
non-achromatic characteristics; and
non-idealities; and
positions of at least one selection from the group consisting of:
effective azimuthal angle of said polarizer means;
azimuthal angle(s) of said compensator means,
retardation of said compensator means as a function of wavelength;
matrix components of said compensator means; and
depolarization/Mueller Matrix components; and
azimuthal angle of said analyzer means;

g. optionally repeating steps e. and f. utilizing a different selection in step e. in normalizing data.

20. A method of calibrating a spectroscopic rotating compensator material system investigation system as in claim 19 which further comprises including calibration parameters for detector element image persistance ($n_k$) and read-out ($p_k$) nonidealities in the mathematical model, and further evaluating said calibration parameters for detector element image persistance and read-out nonidealities in said regression procedure.

21. A method of calibrating a spectroscopic rotating compensator material system investigation system as in claim 19 in which the step of developing a calibration parameter containing mathematical model of said spectroscopic rotating compensator material system investigation system includes the steps of providing a matrix representation of each of said polarizer means, present sample, said compensator means, and said analyzer means, and determining a mathematical transfer function relating electromagnetic beam magnitude out to magnitude in, as a function of wavelength, by multiplication of said matrices in a spectroscopic rotating compensator material system investigation system element presence representing order.

22. A method of calibrating a spectroscopic rotating compensator material system investigation system as in claim 19, which further comprises the step of parameterizing calibration parameter(s) by representing variation as a function of a member of the group consisting of:
wavelength;
angle-of-incidence of said polychromatic beam of electromagnetic radiation with respect to a present sample;
thickness of at least one selection from the group consisting of:
said sample; and
surface layer thereupon;
effective or actual azimuthal angle orientation of one element selected from the group consisting of:
said polarizer means; and
said analyzer means;
DELTA offset resulting from interaction of said electromagnetic beam with a birefringent element of said spectroscopic rotating compensator material system investigation system; and
wavelength shift in data curve resulting from interaction of said electromagnetic beam with an element of said spectroscopic rotating compensator material system investigation system;

by a parameter containing mathematical equation, parameter (s) in said parameter containing mathematical equation being evaluated during said mathematical regression.

23. A method of calibrating a spectroscopic rotating compensator material system investigation system as in claim 22, in which calibration parameter(s) which are parameterized are selected from the group consisting of:
effective polarizer means azimuthal angle orientation;
compensator means azimuthal angle orientation;
matrix components of said compensator means; and
analyzer means azimuthal angle orientation;
each as a function of wavelength.

24. A method of calibrating a spectroscopic rotating compensator material system investigation system as in claim 22 in which the sample is selected from the group consisiting of:
open atmosphere with the spectroscopic ellipsometer being oriented in a "straight-through" configuration; and
other than open atmosphere with the spectroscopic ellipsometer being oriented in a "sample-present" configuration.

25. A method of calibrating a spectroscopic rotating compensator material system investigation system comprising, in any functional order, the steps of:
a. providing a spectroscopic ellipsometer for evaluating a sample comprising:
broadband electromagnetic radiation source means generating a beam having a wavelength extending between over a range of at least 200 to 800 nm;
polarizer means disposed in the path of said beam;
compensator means disposed in the path of the beam, said compensator for inducing phase retardations in the polarization state of the light beam, said compensator means having characteristics other than substantially-non-achromatic, said compensator means being rotated at an angular frequency of ω;

analyzer means that interacts with the beam after the beam interacts with the sample and the compensator means;

detector means that measure the intensity of the beam after the interaction with the analyzer means at a plurality of wavelengths across the wavelength range of at least 200 to 800 nm;

said detector means generating a time varying intensity output signal simultaneously comprising 2ω and 4ω component signals, said 2ω and 4ω component signals being simultaneously present at all wavelengths measured unless the 2 component signal is force to 0.0 by a sample presenting with an ellipsometric DELTA of 0.0 as opposed to being caused to be 0.0 by said compensator means;

b. developing a mathematical model of said spectroscopic ellipsometer which comprises as calibration parameter variables effective polarizer means azimuthal angle orientation, present sample PSI (Ψ), present sample DELTA (Δ), compensator means azimuthal angle orientation, matrix components of said at least one compensator means and analyzer means azimuthal angle orientation, which mathematical model is effectively a transfer function which enables calculation of electromagnetic beam magnitude as a function of wavelength detected by a detector element, given magnitude as a function of wavelength provided by said broadband electromagnetic radiation source means, said mathematical model providing equations for coefficients of terms in said transfer function, said coefficients of terms each being a function of identified calibration parameters;

c. causing a polychromatic beam of electromagnetic radiation produced broadband electromagnetic radiation source to pass through said polarizer means, interact with a sample caused to be in the path thereof, pass through said analyzer means, and enter detector elements in said at least one detector system, with said polychromatic beam of electromagnetic radiation also being caused to pass through said compensator means;

d. obtaining at least two, at least one-dimensional, data set(s) of magnitude values vs. at least one parameter selected from the group consisting of:
  wavelength;
  angle-of-incidence of said polychromatic beam of electromagnetic radiation with respect to a present sample; and
  effective or actual azimuthal angle rotation of one element selected from the group consisting of:
    said polarizer means; and
    said analyzer means;
  over time, while at least one of said compensator means is caused to continuously rotate;

said at least at least two, at least one-dimensional, data set(s) being obtained utilizing a selection from the group consiting of:
  all of said at least two at least one-dimensional data set(s), being obtained utilizing a single sample;
  at least one of said at least two one-dimensional data set(s), being obtained utilizing one sample, with another of said at least two at least one-dimensional data set(s), being obtained utilizing another sample; and
  at least one of said at least two at least one-dimensional data set(s) being obtained with the spectroscopic rotating compensator material system investigation system oriented in a "straight-through" configuration wherein a polychromatic beam of electromagnetic radiation is caused to pass through said polarizer means, pass through said analyzer means, and enter detector elements in said at least one detector system, with said polychromatic beam of electromagnetic radiation also being caused to pass through compensator means but without being caused to interact with any sample other than open ambient atmosphere;

e1. optionally calculating reflectance from at least one selection from the group consisting of:
  obtained A.C.; and
  obtained D.C.;
data without peforming any normalization thereupon;

e2. normalizing data in each said at least two, at least one-dimensional, data set(s) with respect to a selection from the group consisting of:
  a data set D.C. component;
  a data set A.C. component;
  a parameter derived from a combinations of a data set D.C. component and a data set A.C. component;

f. performing a mathematical regression of said mathematical model equations for coefficients of terms in said transfer function, onto said at least two at least one-dimensional data sets thereby evaluating calibration parameters in said mathematical model;

said regression based calibration procedure serving to evaluate parameters in said said mathematical model for at least one selection from the group consisting of:
  non-achromatic characteristics: and
  non-idealities; and
  positions of at least one selection from the group consisting of:
    effective azimuthal angle of said polarizer means;
    azimuthal angle of said compensator means,
    retardation of said compensator means as a function of wavelength;
    matrix components of said compensator means; and
    depolarization/Mueller Matrix components; and
    azimuthal angle of said analyzer means;

g. optionally repeating steps e2. and f. utilizing a different selection in step e2. in normalizing data.

26. A method of calibrating a spectroscopic rotating compensator material system investigation system as in claim 25 in which a Hadamard analysis approach is utilized in evaluating numerical values for coefficients of terms in the transfer function for said spectroscopic rotating compensator material system investigation system.

27. A method of calibrating a spectroscopic rotating compensator material system investigation system as in claim 26 which further comprises including calibration parameters for detector element image persistance ($n_k$) and read-out ($p_k$) nonidealities in the mathematical model, and further evaluating said calibration parameters for detector element image persistance and read-out nonidealities in said regression procedure.

28. A method of calibrating a spectroscopic rotating compensator material system investigation system as in claim 25, in which the step of developing a calibration parameter containing mathematical model of said spectroscopic ellipsometer includes the steps of providing a matrix representation of each of said polarizer means, sample, compensator means and said analyzer means, and determining a transfer function relating electromagnetic beam magnitude out to magnitude in, as a function of wavelength, by multiplication of said matrices in a spectroscopic ellipsometer system element presence representing order.

29. A method of calibrating a spectroscopic rotating compensator material system investigation system as in claim 25 in which the step of evaluating values of coefficients of terms in a transfer function from said at least one, multi-dimensional, data set(s) involves calculating values of coefficients of a Fourier Series.

30. A method of calibrating a spectroscopic ellipsometer system as in claim 25 which further comprises the step of parameterizing calibration parameters by representing variation as a function of a member of the group consisting of:
   wavelength; and
   angle-of-incidence;
of said polychromatic beam of electromagnetic radiation with respect to the sample, and effective or actual azimuthal angle orientation of one element selected from the group consisting of:
   said polarizer means; and
   said analyzer means;
by a parameter containing mathematical equation, said parameters being evaluated during said mathematical regression.

31. A method of calibrating a spectroscopic rotating compensator material system investigation system as in claim 30, in which calibration parameters which are parameterized are selected from the group consisiting of:
   effective polarizer means azimuthal angle orientation;
   compensator means azimuthal angle orientation;
   matrix components of said compensator means; and
   analyzer means azimuthal angle orientation;
each as a function of wavelength.

32. A method of calibrating a spectroscopic rotating compensator material system investigation system as in claim 25 in which the sample is selected from the group consisiting of:
   open atmosphere with the spectroscopic ellipsometer being oriented in a "straight-through" configuration; and
   other than open atmosphere with the spectroscopic ellipsometer being oriented in a "sample-present" configuration.

33. A method of calibrating a spectroscopic ellipsometer system, comprising the steps of:
   a. providing a spectroscopic ellipsometer for evaluating a sample comprising:
   broadband electromagnetic radiation source means generating a beam having wavelengths extending over a range of at least 200 to 800 nm;
   polarizer means disposed in the path of said beam;
   compensator means disposed in the path of the beam, said compensator for inducing phase retardations in the polarization state of the light beam, said compensator means having characteristics other than substantially-non-achromatic, said compensator means being rotated it an angular frequency of $\omega$;
   analyzer means that interact with the beam after the beam interacts with the sample and the compensator means;
   detector means that measure the intensity of the beam after the interaction with the analyzer means at a plurality of wavelengths across the wavelength range of at least 200 to 800 nm;
   said detector means generating a time varying intensity output signal simultaneously comprising $2\omega$ and $4\omega$ component signals, said $2\omega$ and $4\omega$ component signals being simultaneously present at all wavelengths measured unless the $2\omega$ component signal is force to 0.0 by a sample presenting with an ellipsometric DELTA of 0.0 as opposed to being caused to be 0.0 by said compensator means;
   b. developing a mathematical model of said spectroscopic ellipsometer system which comprises as calibration parameter(s) at least one selection from the group consisting of:
   effective polarizer means azimuthal angle orientation;
   present sample PSI ($\Psi$), as a function of angle of incidence and a thickness;
   present sample DELTA ($\Delta$), as a function of angle of incidence and a thickness;
   retardations of said compensator means as a function of wavelength;
   compensator means azimuthal angle orientation;
   matrix components of said compensator means; and
   analyzer means azimuthal angle orientation;
   which mathematical model is effectively a transfer function which enables calculation of electromagnetic beam magnitude detected by a detector element, given magnitude provided by said broadband electromagnetic radiation source means generating a beam having wavelengths extending over a range of at least 200 to 800 nm;
   c. causing a polychromatic beam of electromagnetic radiation produced by said broadband electromagnetic radiation source means, to pass through said polarizer means, interact with a sample caused to be In the path thereof, pass through said analyzer means, and enter detector elements in said detector means, with said polychromatic beam of electromagnetic radiation also being caused to pass through said compensator means;
   d. obtaining at least one, multi-dimensional data set(s) of magnitude values vs. parameters selected from the group consisting of:
   wavelength;
   angle-of-incidence of said polychromatic beam of electromagnetic radiation with respect to a present sample;
   effective or actual azimuthal angle orientation of one element selected from the group consisting of:
   said polarizer means; and
   said analyzer means;
   over time, while at least one of said at least one compensator means is caused to continuously rotate;
   said at least at least one, multi-dimensional data set(s) being obtained utilizing a selection from the group consiting of:
   all of said at least one multi-dimensional data set(s), being obtained utilizing a single sample;
   at least one of said at least one multi-dimensional data sets being obtained utilizing one sample, with another of said at least one multi-dimensional data sets being obtained utilizing another sample; and
   at least one of said at least one multi-dimensional data set(s) being obtained with the spectroscopic ellipsometer oriented in a "straight-through" configuration wherein a polychromatic beam of electromagnetic radiation produced by said broadband electromagnetic radiation source means, generating a beam having wavelengths extending over a range of at least 200 to 800 nm, is caused to pass through said polarizer means, pass through said analyzer means and enter detector elements in said at least one detector system, with said polychromatic beam of electromagnetic radiation also being caused to pass through said compensator means but without being caused to interact with any sample other than open ambient atmosphere;

e1. optionally calculating reflectance from at least one selection from the group consisting of:
   obtained A.C.; and
   obtained D.C.;
data without peforming any normalization thereupon;

e2. normalizing data in each said at least two, at least one-dimensional, data set(s) with respect to a selection from the group consisting of:
   a data set D.C. component;
   a data set A.C. component;
   a parameter derived from a combinations of a data set D.C. component and a data set A.C. component;

f. performing a mathematical regression of said mathematical model onto said normalized at least one, multi-dimensional, data set(s) and optionally said reflectance, thereby evaluating calibration parameters in said mathematical model;

said regression based calibration procedure serving to evaluate parameters in said said mathematical model for at least one selection from the group consisting of:
   non-achromatic characteristics; and
   non-idealities; and
   positions of at least one selection from the group consisting of:
      effective azimuthal angle of said polarizer means;
      azimuthal angle of said compensator means,
      retardation of said compensator means;
      matrix components of said compensator means;
      depolarization/Mueller Matrix components; and
      azimuthal angle of said analyzer means;

g. optionally repeating steps e2. and f. utilizing a different selection in step e2. in normalizing data.

34. A method of calibrating a spectroscopic ellipsometer system as in claim 33, in which step d. involves obtaining at least two, multi-dimensional, data set(s) of magnitude values vs. parameters selected from the group consisting of:
   wavelength;
   angle-of-incidence of said polychromatic beam of electromagnetic radiation with respect to a present sample;
   effective or actual azimuthal angle orientation of one element selected from the group consisting of:
      said polarizer means; and
      said analyzer means;
over time, while at least one of said at least one compensator means is caused to continuously rotate.

35. A method of calibrating a spectroscopic ellipsometer system as in claim 33, in which step d. involves obtaining at least two, multi-dimensional, data set(s) of magnitude values vs. parameters selected from the group consisting of:
   wavelength;
   angle-of-incidence of said polychromatic beam of electromagnetic radiation with respect to a present sample;
   effective or actual azimuthal angle orientation of one element selected from the group consisting of:
      said polarizer means; and
      said analyzer means;
over time, while at least one of said at least one compensator means is caused to continuously rotate.

36. A method of calibrating a spectroscopic ellipsometer system as in claim 33, in which is made a selection from the group consisting of:
   the compensator means is selected to provide retardance which varies by less than ninety (90) degrees (max–min) over a range of wavelengths, within a range of retardations bounded by thirty (30.0) to less than one-hundred-thirty-five (135) degrees, over a range of wavelengths defined by a selection from the group consisting of:
      a. minimum wavelength is less than one-hundred-ninety (190) and maximum wavelength greater than seventeen-hundred (1700) nanometers;
      b. minimum wavelength is less than two-hundred-tventy (220) and maximum wavelength MAXW greater than one-thousand (1000) nanometers;
      c. within a range of wavelengths defined by a maximum wavelength (MAXW) and a minimum wavelength (MINW) range where (MAXW)/(MINW) is at least four-and-one-half (4.5); and
   the compensator means is selected to provide retardance of between seventy-five (75) and one-hundred-thirty (130) degrees over a range of wavelengths defined by a selection from the group consisting of:
      d. between one-hundred-ninety (190) and seven-hundred-fifty (750) nanometers;
      e. between two-hundred-forty-five (245) and nine-hundred (900) nanometers;
      f. between three-hundred-eighty (380) and seventeen-hundred (1700) nanometers;
      g. within a range of wavelengths defined by a maximum wavelength (MAXW) and a minimum wavelength (MINW) wherein the ratio of (MAXW)/(MINW) is at least one-and-eight-tenths (1.8).

37. A method of calibrating a spectroscopic ellipsometer system as in claim 36, in which the compensator is of a construction selected from the group consisting of:
   comprised of a combination of at least two zero-order waveplates, said zero-order waveplates having their respective fast axes rotated to a position offset from zero or ninety degrees with respect to one another;
   comprised of a combination of at least a first and a second effective zero-order wave plate, said first effective zero-order wave plate being comprised of two multiple order waveplates which are combined with the fast axes thereof oriented at a nominal ninety degrees to one another, and said second effective zero-order wave plate being comprised of two multiple order waveplates which are combined with the fast axes thereof oriented at a nominal ninety degrees to one another; the fast axes of the multiple order waveplates in said second effective zero-order wave plate being rotated to a position at a nominal forty-five degrees to the fast axes of the multiple order waveplates in said first effective zero-order waveplate;
   comprised of a combination of at least a first and a second effective zero-order wave plate, said first effective zero-order wave plate being comprised of two multiple order waveplates which are combined with the fast axes thereof oriented at a nominal ninety degrees to one another, and said second effective zero-order wave plate being comprised of two multiple order waveplates which are combined with the fast axes thereof oriented at a nominal ninety degrees to one another; the fast axes of the multiple order waveplates in said second effective zero-order wave plate being rotated to a position away from zero or ninety degrees with respect to the fast axes of the multiple order waveplates in said first effective zero-order waveplate; and comprised of a combination of at least one zero-order waveplate and at least one effective zero-order waveplate, said effective zero-order wave plate being comprised of two multiple order waveplates which are combined with the fast axes thereof oriented at a nominal ninety degrees to one another, the fast axes of the multiple order waveplates in said effective zero-order wave plate being rotated to a position away from zero or ninety degrees with respect to the fast axis of the zero-order waveplate.

38. A method of calibrating a spectroscopic ellipsometer system, comprising the steps of:

a. providing a spectroscopic ellipsometer for evaluating a sample comprising:

broadband electromagnetic radiation source means generating a beam having wavelengths extending over a range of at least 200 to 800 nm;

polarizer means disposed in the path of said beam;

compensator means disposed in the path of the beam, said compensator for inducing phase retardations in the polarization state of the light beam, said compensator means having characteristics other than substantially-non-achromatic, said compensator means being rotated at an angular frequency of $\omega$;

analyzer means that interact with the beam after the beam interacts with the sample and the compensator means;

detector means that measure the intensity of the beam after the interaction with the analyzer means at a plurality of wavelengths across the wavelength range of at least 200 to 800 nm;

said detector means generating a time varying intensity output signal simultaneously comprising $2\omega$ and $4\omega$ component signals, said $2\omega$ and $4\omega$ component signals being simultaneously present at all wavelengths measured unless the $2\omega$ component signal is force to 0.0 by a sample presenting with an ellipsometric DELTA of 0.0 as opposed to being caused to be 0.0 by said compensator means;

b. developing a mathematical model of said spectroscopic ellipsometer system which comprises as calibration parameter(s) at least one selection from the group consisting of:

effective polarizer means azimuthal angle orientation;
present sample PSI ($\Psi$), as a function of angle of incidence and a thickness;
present sample DELTA ($\Delta$), as a function of angle of incidence and a thickness;
retardations of said compensator means as a function of wavelength;
compensator means azimuthal angle orientation;
matrix components of said compensator means; and
analyzer means azimuthal angle orientation;

which mathematical model is effectively a transfer function which enables calculation of electromagnetic beam magnitude detected by a detector element, given magnitude provided by said broadband electromagnetic radiation source means generating a beam having wavelengths extending over a range of at least 200 to 800 nm;

c. causing a polychromatic beam of electromagnetic radiation produced by said broadband electromagnetic radiation source means, to pass through said polarizer means, interact with a sample caused to be in the path thereof, pass through said analyzer means, and enter detector elements in said detector means, with said polychromatic beam of electromagnetic radiation also being caused to pass through said compensator means;

d. obtaining data as described by a selection from the group consisting of:
at least one multi-dimensional data set(s); and
least two, at least one-dimensional data sets;

said data set(s) being magnitude values vs. parameter(s) selected from the group consisting of:
wavelength;
angle-of-incidence of said polychromatic beam of electromagnetic radiation with respect to a present material system;
effective or actual azimuthal angle orientation of one element selected from the group consisting of:
said polarizer; and
said analyzer;

obtained over time, while at least one of said at least one compensator is caused to continuously rotate;

said at least at least one, multi-dimensional data set(s) being obtained utilizing a selection from the group consiting of:
all of said at least one multi-dimensional data set(s), being obtained utilizing a single sample;
at least one of said at least one multi-dimensional data sets being obtained utilizing one sample, with another of said at least one multi-dimensional data sets being obtained utilizing another sample; and
at least one of said at least one multi-dimensional data set(s) being obtained with the spectroscopic ellipsometer oriented in a "straight-through" configuration wherein a polychromatic beam of electromagnetic radiation produced by said broadband electromagnetic radiation source means, generating a beam having wavelengths extending over a range of at least 200 to 800 nm, is caused to pass through said polarizer means, pass through said analyzer means and enter detector elements in said at least one detector system, with said polychromatic beam of electromagnetic radiation also being caused to pass through said compensator means but without being caused to interact with any sample other than open ambient atmosphere;

e1. optionally calculating reflectance from at least one selection from the group consisting of:
obtained A.C. and;
obtained D.C.;
data without peforming any normalization thereupon;

e2. normalizing data in each said at least two, at least one-dimensional, data set(s) with respect to a selection from the group consisting of:
a data set D.C. component;
a data set A.C. component;
a parameter derived from a combinations of a data set D.C. component and a data set A.C. component;

f. performing a mathematical regression of said mathematical model onto said normalized at least one, multi-dimensional, data set(s) and optionally said reflectance, thereby evaluating calibration parameters in said mathematical model;

said regression based calibration procedure serving to evaluate parameters in said said mathematical model for at least one selection from the group consisting of:
non-achromatic characteristics; and non-idealities; and positions of at least one selection from the group consisting of:
  effective azimuthal angle of said polarizer means;
  azimuthal angle of said compensator means,
  retardation of said compensator means;
  matrix components of said compensator means;
  depolarization/Mueller Matrix components; and
  azimuthal angle of said analyzer means;

g. optionally repeating steps e2. and f. utilizing a different selection in step e2. in normalizing data.

39. A method of calibrating a spectroscopic ellipsometer system as in claim 38, in which a selection is made from the group consisting of:

the compensator provides retardance which varies by less than ninety (90) degrees (max–min) over a range of wavelengths, said retardance being within a range of retardations bounded by (30.0) to less than (135) degrees over a range of wavelengths defined by a selection from the group consisting of:
  a. minimum wavelength is less than one-hundred-ninety (190) and maximum wavelength greater than seventeen-hundred (1700) nanometers;
  b. minimum wavelength is less than two-hundred-twenty (220) and maximum wavelength MAXW greater than one-thousand (1000) nanometers;
  c. within a range of wavelengths defined by a maximum wavelength (MAXW) and a minimum wavelength (MINW) range where (MAXW)/(MINW) is at least four-and-one-half (4.5); and the compensator means is selected to provide retardance of between seventy-five (75) and one-hundred-thirty (130) degrees over a range of wavelengths defined by a selection from the group consisting of:
  d. between one-hundred-ninety (190) and seven-hundred-fifty (750) nanometers;
  e. between two-hundred-forty-five (245) and nine-hundred (900) nanometers;
  f. between three-hundred-eighty (380) and seventeen-hundred (1700) nanometers;
  g. within a range of wavelengths defined by a maximum wavelength (MAXW) and a minimum wavelength (MINW) wherein the ratio of (MAXW)/(MINW) is at least one-and-eight-tenths (1.8).

40. A method of calibrating a spectroscopic ellipsometer system as in claim 38, in which the compensator is selected to be of a construction selected from the group consisting of:

comprised of a combination of at least two zero-order waveplates, said zero-order waveplates having their respective fast axes rotated to a position offset from zero or ninety degrees with respect to one another;

comprised of a combination of at least a first and a second effective zero-order wave plate, said first effective zero-order wave plate being comprised of two multiple order waveplates which are combined with the fast axes thereof oriented at a nominal ninety degrees to one another, and said second effective zero-order wave plate being comprised of two multiple order waveplates which are combined with the fast axes thereof oriented at a nominal ninety degrees to one another; the fast axes of the multiple order waveplates in said second effective zero-order wave plate being rotated to a position at a nominal forty-five degrees to the fast axes of the multiple order waveplates in said first effective zero-order waveplate;

comprised of a combination of at least a first and a second effective zero-order wave plate, said first effective zero-order wave plate being comprised of two multiple order waveplates which are combined with the fast axes thereof oriented at a nominal ninety degrees to one another, and said second effective zero-order wave plate being comprised of two multiple order waveplates which are combined with the fast axes thereof oriented at a nominal ninety degrees to one another; the fast axes of the multiple order waveplates in said second effective zero-order wave plate being rotated to a position away from zero or ninety degrees with respect to the fast axes of the multiple order waveplates in said first effective zero-order waveplate; and comprised of a combination of at least one zero-order waveplate and at least one effective zero-order waveplate, said effective zero-order wave plate being comprised of two multiple order waveplates which are combined with the fast axes thereof oriented at a nominal ninety degrees to one another, the fast axes of the multiple order waveplates in said effective zero-order wave plate being rotated to a position away from zero or ninety degrees with respect to the fast axis of the zero-order waveplate.

41. A spectroscopic ellipsometer for evaluating a sample comprising:

broadband electromagnetic radiation source means generating a beam having wavelengths extending over a range of at least 200 to 800 nm;

polarizer means disposed in the path of said beam;

compensator means disposed in the path of the beam, said compensator for inducing phase retardations in the polarization state of the light beam, said compensator means being:
  pseudo-achromatic;

in that the amount of phase retardation varies more with vavelenght, over a range of wavelengths, than is the case if a substantially-achromatic compensator is utilized; but in that the amount of phase retardation varies less with wavelength, over said range of wavelengths, than is the case if a substantially-non-achromatic compensator is utilized, said compensator means being rotated at an angular frequency of $\omega$;

analyzer means that interact with the beam after the beam interacts with the sample and the compensator means;

detector means that measure the intensity of the beam after the interaction with the analyzer means at a plurality of wavelengths across the wavelength range of at least 200 to 800 nm;

said detector means generating a time varying intensity output signal simultaneously comprising $2\omega$ and $4\omega$ component signals, said $2\omega$ and $4\omega$ component signals being simultaneously present at all wavelengths measured unless the $2\omega$ component signal is force to 0.0 by a sample presenting with an ellipsometric DELTA of 0.0 as opposed to being caused to be 0.0 by said compensator means;

optionally further comprising processor means for evaluating the sample based on the intensity output signal;

said compensator means being a selection from the group consisting of:
  comprised of a combination of at least two zero-order waveplates, said zero-order waveplates having their respective fast axes rotated to a position offset from zero or ninety degrees with respect to one another;
  comprised of a combination of at least a first and a second effective zero-order wave plate, said first effective zero-order wave plate being comprised of two multiple order waveplates which are combined with the fast axes thereof oriented at a nominal ninety degrees to one another, and said second effective zero-order wave plate being comprised of two multiple order waveplates which are combined with the fast axes thereof oriented at a nominal ninety degrees to one another; the fast axes of the multiple order waveplates in said second effective zero-order wave plate being rotated to a position at a nominal forty-five degrees to the fast axes of the multiple order waveplates in said first effective zero-order waveplate;

comprised of a combination of at least a first and a second effective zero-order wave plate, said first effective zero-order wave plate being comprised of two multiple order waveplates which are combined with the fast axes thereof oriented at a nominal ninety degrees to one another, and said second effective zero-order wave plate being comprised of two multiple order waveplates which are combined with the fast axes thereof oriented at a nominal ninety degrees to one another; the fast axes of the multiple order waveplates in said second effective zero-order wave plate being rotated to a position away from zero or ninety degrees with respect to the fast axes of the multiple order waveplates in said first effective zero-order waveplate; and comprised of a combination of at least one zero-order waveplate and at least one effective zero-order waveplate, said effective zero-order wave plate being comprised of two multiple order waveplates which are combined with the fast axes thereof oriented at a nominal ninety degrees to one another, the fast axes of the multiple order waveplates in said effective zero-order wave plate being rotated to a position away from zero or ninety degrees with respect to the fast axis of the zero-order waveplate.

42. A spectroscopic ellipsometer system as in claim 41, in which a selection is made from the group consisting of:

the compensator provides retardance which varies by less than ninety (90) degrees (max–min) over a range of wavelengths, said retardance being within a range of retardations bounded by (30.0) to less than (135) degrees over a range of wavelengths defined by a selection from the group consisting of:
  a. minimum wavelength is less than one-hundred-ninety (190) and maximum wavelength greater than seventeen-hundred (1700) nanometers;
  b. minimum wavelength is less than two-hundred-twenty (220) and maximum wavelength MAXW greater than one-thousand (1000) nanometers;
  c. within a range of wavelengths defined by a maximum wavelength (MAXW) and a minimum wavelength (MINW) range where (MAXW)/(MINW) is at least four-and-one-half (4.5); and the compensator means is selected to provide retardance of between seventy-five (75) and one-hundred-thirty (130) degrees over a range of wavelengths defined by a selection from the group consisting of:
  d. between one-hundred-ninety (190) and seven-hundred-fifty (750) nanometers;
  e. between two-hundred-forty-five (245) and nine-hundred (900) nanometers;
  f. between three-hundred-eighty (380) and seventeen-hundred (1700) nanometers;
  g. within a range of wavelengths defined by a maximum wavelength (MAXW) and a minimum wavelength (MINW) wherein the ratio of (MAXW)/(MINW) is at least one-and-eight-tenths (1.8).

43. A spectroscopic ellipsometer for evaluating a sample comprising:

a broadband light source generating a beam having wavelengths extending over a range of at least 200 to 800 nm;

a polarizer disposed in the path of the light beam;

a compensator disposed in the path of the light beam, said compensator for inducing phase retardations in the polarization state of the light beam, said compensator providing retardance which varies by less than ninety (90) degrees (max–min) over a range of wavelengths, said retardance being within a range of retardations bounded by (30.0) to less than (135) degrees over a range of wavelengths, said compensator being rotated at a an angular frequence of $\omega$;

an analyzer that interacts with the light beam after the beam interacts with the sample and with the compensator;

a detector that measures the intensity of the light beam after the interaction with the analyzer at a plurality of wavelengths across the wavelength range of at least 200 to 800 nm;

said detector generating a time varying intensity output signal simultaneously comprising $2\omega$ and $4\omega$ component signals, said $2\omega$ and $4\omega$ component signals being simultaneously present at all wavelengths measured unless the $2\omega$ component signal is force to 0.0 by a sample presenting with an ellipsometric DELTA of 0.0 as opposed to being caused to be 0.0 by said compensator means.

44. A spectroscopic ellipsometer for evaluating a sample comprising:

a broadband light source generating abeam having wavelengths extending over a spectroscopic range;

a polarizer disposed in the path of the light beam;

a compensator disposed in the path of the light beam, said compensator for inducing phase retardations in the polarization state of the light beam, said compensator being characterized by a fast axis azimuthal angle which varies with wavelength, said compensator being rotated at an angular frequency of $\omega$;

an analyzer that interacts with the light beam after the beam interacts with the sample and with the compensator;

a detector that measures the intensity of the light beam after the interaction with the analyzer at a plurality of wavelengths across the spectroscopic wavelength range;

said detector generating a time varying intensity output signal simultaneously comprising $2\omega$ and $4\omega$ component signals, said $2\omega$ and $4\omega$ component signals being simultaneously present at all wavelengths measured unless the $2\omega$ component signal is force to 0.0 by a sample presenting with an ellipsometric DELTA of 0.0 as opposed to being caused to be 0.0 by said compensator means.

* * * * *